US012790406B2

(12) United States Patent
Qin et al.

(10) Patent No.: US 12,790,406 B2
(45) Date of Patent: Nov. 10, 2026

(54) PSMA ANTIBODIES AND USES THEREOF

(71) Applicant: Wuxi Biologics Ireland Limited, Dundalk (IE)

(72) Inventors: Yi Qin, Shanghai (CN); Yunying Chen, Louth (IE); Xia Wang, Shanghai (CN); Jijie Gu, Shanghai (CN)

(73) Assignee: Wuxi Biologics Ireland Limited, Mullagharlin (IE)

( * ) Notice: Subject to any disclaimer, the term of this patent is extended or adjusted under 35 U.S.C. 154(b) by 0 days.

(21) Appl. No.: 19/210,620

(22) Filed: May 16, 2025

(65) Prior Publication Data

US 2025/0277054 A1 Sep. 4, 2025

Related U.S. Application Data

(63) Continuation of application No. PCT/CN2023/133153, filed on Nov. 22, 2023.

(30) Foreign Application Priority Data

Nov. 24, 2022 (WO) ................ PCT/CN2022/134047
Nov. 24, 2022 (WO) ................ PCT/CN2022/134163

(51) Int. Cl.
*A61P 35/00* (2006.01)
*C07K 16/28* (2006.01)
*C07K 16/30* (2006.01)
*A61K 39/00* (2006.01)

(52) U.S. Cl.
CPC .......... *C07K 16/3069* (2013.01); *A61P 35/00* (2018.01); *C07K 16/2809* (2013.01); *A61K 2039/505* (2013.01); *C07K 2317/31* (2013.01); *C07K 2317/524* (2013.01); *C07K 2317/526* (2013.01); *C07K 2317/53* (2013.01); *C07K 2317/565* (2013.01); *C07K 2317/73* (2013.01); *C07K 2317/92* (2013.01)

(58) Field of Classification Search
CPC ............ C07K 16/3069; C07K 16/2809; C07K 2317/31; C07K 2317/524; C07K 2317/526; C07K 2317/53; C07K 2317/565; C07K 2317/73; C07K 2317/92; C07K 2317/21; C07K 2317/33; C07K 2317/94; A61P 35/00; A61K 2039/505
See application file for complete search history.

(56) References Cited

U.S. PATENT DOCUMENTS

| | | | | |
|---|---|---|---|---|
| 9,631,191 | B2 * | 4/2017 | Zdanovsky | G01N 33/6845 |
| 2017/0210799 | A1 * | 7/2017 | Anderson | A61P 35/00 |
| 2017/0218079 | A1 | 8/2017 | Raum et al. | |
| 2023/0002489 | A1 | 1/2023 | Wu et al. | |
| 2023/0121775 | A1 | 4/2023 | Schellenberger et al. | |

FOREIGN PATENT DOCUMENTS

| | | | | |
|---|---|---|---|---|
| CN | 114106171 | B * | 5/2023 | C07K 16/18 |
| WO | 2002098897 | A2 | 12/2002 | |
| WO | 2019057124 | A1 | 3/2019 | |
| WO | WO-2019057122 | A1 * | 3/2019 | C07K 16/2803 |
| WO | 2020156405 | A1 | 8/2020 | |
| WO | 2021/104430 | A1 | 6/2021 | |
| WO | 2021222578 | A1 | 11/2021 | |
| WO | 2022022464 | A1 | 2/2022 | |
| WO | WO-2022026475 | A2 * | 2/2022 | C07K 16/1003 |
| WO | 2022263507 | A1 | 12/2022 | |
| WO | 2023002392 | A1 | 1/2023 | |
| WO | 2023015170 | A2 | 2/2023 | |
| WO | 2023036326 | A1 | 3/2023 | |
| WO | 2023078450 | A1 | 5/2023 | |
| WO | 2023147331 | A1 | 8/2023 | |

OTHER PUBLICATIONS

International Search Report and Written Opinion for International Application No. PCT/CN2023/133153, mailed Apr. 12, 2024, 10 Pages.

Zorko Nicholas A et al: "Novel immune engagers and cellular therapies for metastatic castration-resistant prostate cancer: do we take a BiTe, TriKEs, and CARs?", Prostate Cancer and Prostatic Disease, Stockon Press, Basingstoke, GB, vol. 24, No. 4, May 25, 2021 (May 25, 2021), pp. 986-996, XP037628207, ISSN: 1365-7852, DOI: 10.1038/S41391-021-00381-W, [retrieved on May 25, 2021] e.g. p. 988, left-hand column, paragraph 2-right-hand column, paragraph 2; table 2, rows 2 and 5;the whole document.

* cited by examiner

*Primary Examiner* — Misook Yu
*Assistant Examiner* — Dennis Cherian George
(74) *Attorney, Agent, or Firm* — Cynthia Lan Martin

(57) ABSTRACT

The present application provides prostate-specific membrane antigen (PSMA) antibodies such as human monoclonal antibodies against PSMA, nucleic acid molecules encoding the antibodies, expression vectors and host cells used for expression of the antibodies, methods for preparing the same, and their uses such as the treatment of PSMA-related diseases including cancer.

18 Claims, 22 Drawing Sheets

Specification includes a Sequence Listing.

GEL INFO: NuPAGE, NOVEX 4-12% BIS-TRIS GEL

| LANE | PROTEIN NAME | MW(kDa) |
|---|---|---|
| 1 | W305042 (NON-REDUCED) | 143.8 |
| 2 | W305042 (REDUCED) | 49+23 |
| M | PAGERULER™ UNSTAINED PROTEIN LADDER | |

GEL INFO: NuPAGE, NOVEX 4-12% BIS-TRIS GEL

SEQUENCE LISTING

```
Sequence total quantity: 38
SEQ ID NO: 1            moltype = AA  length = 10
FEATURE                 Location/Qualifiers
source                  1..10
                        mol_type = protein
                        organism = synthetic construct
SEQUENCE: 1
GYSFTTYWIG                                                          10

SEQ ID NO: 2            moltype = AA  length = 17
FEATURE                 Location/Qualifiers
source                  1..17
                        mol_type = protein
                        organism = synthetic construct
SEQUENCE: 2
IIYPYDSDTR YSPSFQG                                                  17

SEQ ID NO: 3            moltype = AA  length = 9
FEATURE                 Location/Qualifiers
source                  1..9
                        mol_type = protein
                        organism = synthetic construct
SEQUENCE: 3
ITGGYLFDY                                                           9

SEQ ID NO: 4            moltype = AA  length = 14
FEATURE                 Location/Qualifiers
source                  1..14
                        mol_type = protein
                        organism = synthetic construct
SEQUENCE: 4
TGTSSDVGGY NYVS                                                     14

SEQ ID NO: 5            moltype = AA  length = 7
FEATURE                 Location/Qualifiers
source                  1..7
                        mol_type = protein
                        organism = synthetic construct
SEQUENCE: 5
EVTKRPS                                                             7

SEQ ID NO: 6            moltype = AA  length = 10
FEATURE                 Location/Qualifiers
source                  1..10
                        mol_type = protein
                        organism = synthetic construct
SEQUENCE: 6
TSYAGSNKYV                                                          10

SEQ ID NO: 7            moltype = AA  length = 10
FEATURE                 Location/Qualifiers
source                  1..10
                        mol_type = protein
                        organism = synthetic construct
SEQUENCE: 7
GFAFTDYYIH                                                          10

SEQ ID NO: 8            moltype = AA  length = 17
FEATURE                 Location/Qualifiers
source                  1..17
                        mol_type = protein
                        organism = synthetic construct
SEQUENCE: 8
WISPGNVNTK YNENFKG                                                  17

SEQ ID NO: 9            moltype = AA  length = 10
FEATURE                 Location/Qualifiers
source                  1..10
```

```
                         mol_type = protein
                         organism = synthetic construct
SEQUENCE: 9
DGYSLYYFDY                                                10

SEQ ID NO: 10            moltype = AA  length = 17
FEATURE                  Location/Qualifiers
source                   1..17
                         mol_type = protein
                         organism = synthetic construct
SEQUENCE: 10
KSSQSLLNSR TRKNYLA                                        17

SEQ ID NO: 11            moltype = AA  length = 7
FEATURE                  Location/Qualifiers
source                   1..7
                         mol_type = protein
                         organism = synthetic construct
SEQUENCE: 11
WASTRQS                                                   7

SEQ ID NO: 12            moltype = AA  length = 8
FEATURE                  Location/Qualifiers
source                   1..8
                         mol_type = protein
                         organism = synthetic construct
SEQUENCE: 12
TQSHTLRT                                                  8

SEQ ID NO: 13            moltype = AA  length = 119
FEATURE                  Location/Qualifiers
source                   1..119
                         mol_type = protein
                         organism = synthetic construct
SEQUENCE: 13
QVQLVQSGAE VKKPGSSVKV SCKASGFAFT DYYIHWVRQA PGQGLEWMGW ISPGNVNTKY  60
NENFKGRVTI TADKSTSTAY MELSSLRSED TAVYYCARDG YSLYYFDYWG QGTLVTVLE   119

SEQ ID NO: 14            moltype = AA  length = 112
FEATURE                  Location/Qualifiers
source                   1..112
                         mol_type = protein
                         organism = synthetic construct
SEQUENCE: 14
DIVMTQSPDS LAVSLGERAT INCKSSQSLL NSRTRKNYLA WYQQKPGQPP KLLIYWASTR  60
QSGVPDRFSG SGSGTDFTLT ISSLQAEDVA VYYCTQSHTL RTFGGGTKVE IK          112

SEQ ID NO: 15            moltype = AA  length = 118
FEATURE                  Location/Qualifiers
source                   1..118
                         mol_type = protein
                         organism = synthetic construct
SEQUENCE: 15
EVQLVQSGAE VKKPGESLKI SCKASGYSFT TYWIGWVRQM PGKGLELMGI IYPYDSDTRY  60
SPSFQGQVTI SADKSINTAY LQWSSLKASD TAMYYCARIT GGYLFDYWGQ GILVTVSS    118

SEQ ID NO: 16            moltype = AA  length = 110
FEATURE                  Location/Qualifiers
source                   1..110
                         mol_type = protein
                         organism = synthetic construct
SEQUENCE: 16
QSALTQPPSA SGSPGQSVTI SCTGTSSDVG GYNYVSWYQQ HPGKAPKLMI YEVTKRPSGV  60
PDRFSGSKSG NTASLTVSGL QAEDEADYYC TSYAGSNKYV FGTGTKVTVL            110

SEQ ID NO: 17            moltype = AA  length = 471
FEATURE                  Location/Qualifiers
source                   1..471
                         mol_type = protein
                         organism = synthetic construct
SEQUENCE: 17
QVQLVQSGAE VKKPGSSVKV SCKASGFAFT DYYIHWVRQA PGQGLEWMGW ISPGNVNTKY  60
NENFKGRVTI TADKSTSTAY MELSSLRSED TAVYYCARDG YSLYYFDYWG QGTLVTVLED  120
LKNVFPPEVA VFEPSECEIS HTQKATLVCL ATGFYPDHVE LSWWVNGKEV HSGVCTDPQP  180
LKEQPALQDS RYALSSRLRV SATFWQNPRN HFRCQVQFYG LSENDEWTQD RAKPVTQIVS  240
AEAWGRYGPP CPPCPAPEAA GGPSVFLFPP KPKDTLMISR TPEVTCVVVD VSQEDPEVQF  300
NWYVDGVEVH NAKTKPREEQ FNSTYRVVSV LTVLHQDWLN GKEYKCKVSN KGLPSSIEKT  360
ISKAKGQPRE PQVYTLPPCQ EEMTKNQVSL WCLVKGFYPS DIAVEWESNG QPENNYKTTP  420
PVLDSDGSFF LYSRLTVDKS RWQEGNVFSC SVMHEALHNH YTQKSLSLSL G          471
```

```
SEQ ID NO: 18          moltype = AA  length = 203
FEATURE                Location/Qualifiers
source                 1..203
                       mol_type = protein
                       organism = synthetic construct
SEQUENCE: 18
DIVMTQSPDS LAVSLGERAT INCKSSQSLL NSRTRKNYLA WYQQKPGQPP KLLIYWASTR  60
QSGVPDRFSG SGSGTDFTLT ISSLQAEDVA VYYCTQSHTL RTFGGGTKVE IKPDIQNPDP  120
AVYQLRDSKS SDKSVCLFTD FDSQTQVSQS KDSDVYITDK CVLDMRSMDF KSNSAVAWSQ  180
KSDFACANAF QNSIIPEDTF FCS                                          203

SEQ ID NO: 19          moltype = AA  length = 444
FEATURE                Location/Qualifiers
source                 1..444
                       mol_type = protein
                       organism = synthetic construct
SEQUENCE: 19
EVQLVQSGAE VKKPGESLKI SCKASGYSFT TYWIGWVRQM PGKGLELMGI IYPYDSDTRY  60
SPSFQGQVTI SADKSINTAY LQWSSLKASD TAMYYCARIT GGYLFDYWGQ GILVTVSSAS  120
TKGPSVFPLA PCSRSTSEST AALGCLVKDY FPEPVTVSWN SGALTSGVHT FPAVLQSSGL  180
YSLSSVVTVP SSSLGTKTYT CNVDHKPSNT KVDKRVESKY GPPCPPCPAP EAAGGPSVFL  240
FPPKPKDTLM ISRTPEVTCV VVDVSQEDPE VQFNWYVDGV EVHNAKTKPR EEQFNSTYRV  300
VSVLTVLHQD WLNGKEYKCK VSNKGLPSSI EKTISKAKGQ PREPQVCTLP PSQEEMTKNQ  360
VSLSCAVKGF YPSDIAVEWE SNGQPENNYK TTPPVLDSDG SFFLVSRLTV DKSRWQEGNV  420
FSCSVMHEAL HNHYTQKSLS LSLG                                         444

SEQ ID NO: 20          moltype = AA  length = 216
FEATURE                Location/Qualifiers
source                 1..216
                       mol_type = protein
                       organism = synthetic construct
SEQUENCE: 20
QSALTQPPSA SGSPGQSVTI SCTGTSSDVG GYNYVSWYQQ HPGKAPKLMI YEVTKRPSGV  60
PDRFSGSKSG NTASLTVSGL QAEDEADYYC TSYAGSNKYV FGTGTKVTVL GQPKAAPSVT  120
LFPPSSEELQ ANKATLVCLI SDFYPGAVTV AWKADSSPVK AGVETTTPSK QSNNKYAASS  180
YLSLTPEQWK SHKSYSCQVT HEGSTVEKTV APTECS                             216

SEQ ID NO: 21          moltype = DNA  length = 357
FEATURE                Location/Qualifiers
source                 1..357
                       mol_type = other DNA
                       organism = synthetic construct
SEQUENCE: 21
caggtgcagc ttgtgcagtc tggggcagaa gtgaagaagc ctgggtctag tgtcaaggtg  60
tcatgcaagg ctagcgggtt cgcctttact gactactaca tccactgggt gcggcaggct  120
cccggacaag ggttggagtg gatgggatgg atctccccag gcaatgtcaa cacaaagtac  180
aacgagaact tcaaaggccg cgtcaccatt accgccgaca agagcacctc cacagcctac  240
atggagctgt ccagcctcag aagcgaggac actgccgtct actactgtgc cagggatggg  300
tactccctgt attactttga ttactggggc cagggcacac tggtgacagt gctggag     357

SEQ ID NO: 22          moltype = DNA  length = 336
FEATURE                Location/Qualifiers
source                 1..336
                       mol_type = other DNA
                       organism = synthetic construct
SEQUENCE: 22
gatatcgtga tgacccagag cccagactcc cttgctgtct ccctcggcga aagagcaacc  60
atcaactgca agagctccca aagcctgctg aactccagga ccaggaagaa ttacctggcc  120
tggtatcagc agaagcccgg ccagcctcct aagctgctca tctactgggc ctccacccgg  180
cagtctgggg tgcccgatcg gtttagtgga tctgggagcg ggacagactt cacattgaca  240
attagctcac tgcaggccga ggacgtggcc gtctactact gtactcagag ccacactctc  300
cgcacattcg gcggagggac taaagtggag attaag                            336

SEQ ID NO: 23          moltype = DNA  length = 354
FEATURE                Location/Qualifiers
source                 1..354
                       mol_type = other DNA
                       organism = synthetic construct
SEQUENCE: 23
gaggtgcagc tggtgcagtc tggagcagag gtgaaaaagc ccggggagtc tctgaagatc  60
tcctgtaagg cttctggata cagctttacc acctactgga tcggctgggt gcgccagatg  120
cccgggaaag gcctggagtt aatggggatc atctatcctt atgactctga taccagatac  180
agcccgtcct tccaaggcca ggtcaccatc tcagccgaca agtccatcaa caccgcctac  240
ctgcagtgga gcagcctgaa ggcctcggac accgccatgt attactgtgc gagaattacg  300
ggtggctacc tctttgacta ctggggccag ggaatcctgg tcaccgtctc ctca        354

SEQ ID NO: 24          moltype = DNA  length = 330
FEATURE                Location/Qualifiers
```

```
source                  1..330
                        mol_type = other DNA
                        organism = synthetic construct
SEQUENCE: 24
cagtctgccc tgactcagcc tccctccgcg tccgggtctc ctggacagtc agtcaccatc  60
tcctgcactg gaaccagcag tgacgttggt ggttataact atgtctcctg gtaccaacag  120
cacccaggca aagcccccaa actcatgatt tatgaggtca ctaagcggcc ctcaggggtc  180
cctgatcgct tctctggctc caagtctggc aacacggcct ccctgaccgt ctctgggctc  240
caggctgagg atgaggctga ttattactgc acctcatatg caggcagcaa caaatatgtc  300
ttcggaactg ggaccaaggt caccgtccta                                   330

SEQ ID NO: 25           moltype = DNA  length = 1413
FEATURE                 Location/Qualifiers
source                  1..1413
                        mol_type = other DNA
                        organism = synthetic construct
SEQUENCE: 25
caggtgcagc ttgtgcagtc tggggcagaa gtgaagaagc ctgggtctag tgtcaaggtg  60
tcatgcaagg ctagcgggtt cgcctttact gactactaca tccactgggt gcggcaggct  120
cccggacaag ggttggagtg gatgggatgg atctccccag gcaatgtcaa cacaaagtac  180
aacgagaact tcaaaggccg cgtcaccatt accgccgaca agagcacctc cacagcctac  240
atggagctgt ccagcctcag aagcgaggac actgccgtct actactgtgc cagggatggg  300
tactccctgt attactttga ttactggggc cagggcacac tggtgacagt gctggaggac  360
ctgaagaacg tgttccctcc cgaggtggcc gtgttcgaac ccagcgagtg cgagatcagc  420
cacacccaga aggccaccct ggtgtgtctg gccaccggct tctaccccga ccacgtggag  480
ctgagctggt gggtgaacgg caaggaggtg cacagcggcg tgtgtaccga ccctcagccc  540
ctgaaggagc agcccgccct gcaggacagc aggtacgccc tgagcagcag gctgagagtg  600
agcgccacct tctggcagaa ccccaggaac cacttcaggt gccaggtgca gttctacggc  660
ctgagcgaga acgacgagtg gacccaggac agggccaagc ccgtgaccca gatcgtgagc  720
gctgaggcct ggggcagata tggtccccca tgcccaccat gcccagcacc tgaggccgct  780
gggggaccat cagtcttcct gttcccccca aaacccaagg acactctcat gatctcccgg  840
acccctgagg tcacgtgcgt ggtggtggac gtgagccagg aagaccccga ggtccagttc  900
aactggtacg tggatggcgt ggaggtgcat aatgccaaga caaagccgcg ggaggagcag  960
ttcaacagca cgtaccgtgt ggtcagcgtc ctcaccgtcc tgcaccagga ctggctgaac  1020
ggcaaggagt acaagtgcaa ggtctccaac aaaggcctcc cgtcctccat cgagaaaacc  1080
atctccaaag ccaaagggca gccccgagag ccacaggtgt acaccctgcc cccatgccag  1140
gaggagatga ccaagaacca ggtcagcctg tggtgcctgg tcaaaggctt ctaccccagc  1200
gacatcgccg tggagtggga gagcaatggg cagccggaga acaactacaa gaccacgcct  1260
cccgtgctgg actccgacgg ctccttcttc ctctacagca ggctaaccgt ggacaagagc  1320
aggtggcagg aggggaatgt cttctcatgc tccgtgatgc atgaggctct gcacaaccac  1380
tacacacaga agagcctctc cctgtctctg ggt                              1413

SEQ ID NO: 26           moltype = DNA  length = 609
FEATURE                 Location/Qualifiers
source                  1..609
                        mol_type = other DNA
                        organism = synthetic construct
SEQUENCE: 26
gatatcgtga tgacccagag cccagactcc cttgctgtct ccctcggcga aagagcaacc  60
atcaactgca agagctccca aagcctgctg aactccagga ccaggaagaa ttacctggcc  120
tggtatcagc agaagcccgg ccagcctcct aagctgctca tctactgggc ctccacccgg  180
cagtctgggg tgcccgatcg gtttagtgga tctgggagcg ggacagactt cacattgaca  240
attagctcac tgcaggccga ggacgtggcc gtctactact gtactcagag ccacactctc  300
cgcacattcg gcggagggac taaagtggag attaagcccg acatccagaa ccccgacccc  360
gccgtgtacc agctgagaga cagcaagagc agcgacaaga gcgtgtgcct gttcaccgac  420
ttcgacagcc agacccaggt gagccagagc aaggactccg acgtgtatat caccgacaag  480
tgcgtgctgg acatgaggag catggacttc aagagcaaca gcgccgtggc ctggagccag  540
aagagcgact tcgcctgcgc caacgccttc cagaacagca tcatccccga ggacaccttc  600
ttctgcagc                                                          609

SEQ ID NO: 27           moltype = DNA  length = 1332
FEATURE                 Location/Qualifiers
source                  1..1332
                        mol_type = other DNA
                        organism = synthetic construct
SEQUENCE: 27
gaggtgcagc tggtgcagtc tggagcagag gtgaaaaagc ccggggagtc tctgaagatc  60
tcctgtaagg cttctggata cagctttacc acctactgga tcggctgggt gcgccagatg  120
cccgggaaag gcctggagtt aatggggatc atctatcctt atgactctga taccagatac  180
agcccgtcct tccaaggcca ggtcaccatc tcagccgaca agtccatcaa caccgcctac  240
ctgcagtgga gcagcctgaa ggcctcggac accgccatgt attactgtgc gagaattacg  300
ggtggctacc tctttgacta ctggggccag ggaatcctgg tcaccgtctc ctcagcgtcg  360
accaagggcc catccgtctt ccccctggcg ccctgctcca ggagcacctc cgagagcaca  420
gccgccctgg gctgcctggt caaggactac ttccccgaac cggtgacggt gtcgtggaac  480
tcaggcgccc tgaccagcgg cgtgcacacc ttcccggctg tcctacagtc ctcaggactc  540
tactccctca gcagcgtggt gaccgtgccc tccagcagct tgggcacgaa gacctacacc  600
tgcaacgtag atcacaagcc cagcaacacc aaggtggaca agagagttga gtccaaatat  660
ggtcccccat gcccaccatg cccagcacct gaggcagcag ggggaccatc agtcttcctg  720
ttccccccaa aacccaagga cactctcatg atctcccgga cccctgaggt cacgtgcgtg  780
```

```
gtggtggacg tgagccagga agaccccgag gtccagttca actggtacgt ggatggcgtg  840
gaggtgcata atgccaagac aaagccgcgg gaggagcagt tcaacagcac gtaccgtgtg  900
gtcagcgtcc tcaccgtcct gcaccaggac tggctgaacg gcaaggagta caagtgcaag  960
gtctccaaca aaggcctccc gtcctccatc gagaaaacca tctccaaagc caaagggcag  1020
ccccgagagc cacaggtgtg caccctgccc ccatcccagg aggagatgac caagaaccag  1080
gtcagcctga gctgcgcggt caaaggcttc taccccagcg acatcgccgt ggagtgggag  1140
agcaatgggc agccggagaa caactacaag accacgcctc ccgtgctgga ctccgacggc  1200
tccttcttcc tcgttagcag gctaaccgtg gacaagagca ggtggcagga ggggaatgtc  1260
ttctcatgct ccgtgatgca tgaggctctg cacaaccact acacacagaa gagcctctcc  1320
ctgtctctgg gt                                                     1332

SEQ ID NO: 28           moltype = DNA  length = 648
FEATURE                 Location/Qualifiers
source                  1..648
                        mol_type = other DNA
                        organism = synthetic construct
SEQUENCE: 28
cagtctgccc tgactcagcc tccctccgcg tccgggtctc ctggacagtc agtcaccatc  60
tcctgcactg gaaccagcag tgacgttggt ggttataact atgtctcctg gtaccaacag  120
cacccaggca aagcccccaa actcatgatt tatgaggtca ctaagcggcc ctcaggggtc  180
cctgatcgct tctctggctc caagtctggc aacacggcct ccctgaccgt ctctgggctc  240
caggctgagg atgaggctga ttattactgc acctcatatg caggcagcaa caaatatgtc  300
ttcggaactg ggaccaaggt caccgtccta ggtcagccca aggctgcccc ctcggtcact  360
ctgttcccgc cctcctctga ggagcttcaa gccaacaagg ccacactggt gtgtctcata  420
agtgacttct acccgggagc cgtgacagtg gcctggaagg cagatagcag ccccgtcaag  480
gcgggagtgg agaccaccac accctccaaa caaagcaaca acaagtacgc ggccagcagc  540
tacctgagcc tgacgcctga gcagtggaag tcccacaaaa gctacagttg ccaggtcacg  600
catgaaggga gcaccgtgga gaagacagtg gcccctacag aatgttca               648

SEQ ID NO: 29           moltype = AA  length = 127
FEATURE                 Location/Qualifiers
source                  1..127
                        mol_type = protein
                        organism = synthetic construct
SEQUENCE: 29
DLKNVFPPEV AVFEPSECEI SHTQKATLVC LATGFYPDHV ELSWWVNGKE VHSGVCTDPQ  60
PLKEQPALQD SRYALSSRLR VSATFWQNPR NHFRCQVQFY GLSENDEWTQ DRAKPVTQIV  120
SAEAWGR                                                           127

SEQ ID NO: 30           moltype = AA  length = 91
FEATURE                 Location/Qualifiers
source                  1..91
                        mol_type = protein
                        organism = synthetic construct
SEQUENCE: 30
PDIQNPDPAV YQLRDSKSSD KSVCLFTDFD SQTQVSQSKD SDVYITDKCV LDMRSMDFKS  60
NSAVAWSQKS DFACANAFQN SIIPEDTFFC S                                91

SEQ ID NO: 31           moltype = AA  length = 447
FEATURE                 Location/Qualifiers
source                  1..447
                        mol_type = protein
                        organism = synthetic construct
SEQUENCE: 31
EVQLVQSGAE VKKPGESLKI SCKASGYSFT TYWIGWVRQM PGKGLELMGI IYPYDSDTRY  60
SPSFQGQVTI SADKSINTAY LQWSSLKASD TAMYYCARIT GGYLFDYWGQ GILVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 32           moltype = AA  length = 216
FEATURE                 Location/Qualifiers
source                  1..216
                        mol_type = protein
                        organism = synthetic construct
SEQUENCE: 32
QSALTQPPSA SGSPGQSVTI SCTGTSSDVG GYNYVSWYQQ HPGKAPKLMI YEVTKRPSGV  60
PDRFSGSKSG NTASLTVSGL QAEDEADYYC TSYAGSNKYV FGTGTKVTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                           216

SEQ ID NO: 33           moltype = DNA  length = 1344
FEATURE                 Location/Qualifiers
source                  1..1344
                        mol_type = other DNA
                        organism = synthetic construct
```

```
SEQUENCE: 33
gaggtgcagc tggtgcagtc tggagcagag gtgaaaaagc ccggggagtc tctgaagatc  60
tcctgtaagg cttctggata cagctttacc acctactgga tcggctgggt gcgccagatg  120
cccgggaaag gcctggagtt aatggggatc atctatcctt atgactctga taccagatac  180
agcccgtcct tccaaggcca ggtcaccatc tcagccgaca agtccatcaa caccgcctac  240
ctgcagtgga gcagcctgaa ggcctcggac accgccatgt attactgtgc gagaattacg  300
ggtggctacc tctttgacta ctggggccag ggaatcctgg tcaccgtctc ctcagcgtcg  360
accaagggcc catccgtctt cccccctggca ccctcctcca agagcacctc tgggggcaca  420
gcggccctgg gctgcctggt caaggactac ttccccgaac cggtgacggt gtcctggaac  480
tcaggcgctc tgaccagcgg cgtgcacacc ttcccggctg tcctacagtc ctcaggactc  540
tactccctca gcagcgtggt gaccgtgccc tccagcagct tgggcaccca gacctacatc  600
tgcaacgtga atcacaagcc cagcaacacc aaggtggaca agagagttga gcccaaatct  660
tgtgacaaaa ctcacacatg cccaccgtgc ccagcacctg aactcctggg gggaccgtca  720
gtcttcctct tcccccaaa acccaaggac accctcatga tctcccggac ccctgaggtc  780
acatgcgtgg tggtggacgt gagccacgaa gaccctgagg tcaagttcaa ctggtacgtg  840
gacggcgtgg aggtgcataa tgccaagaca aagccgcggg aggagcagta caacagcacg  900
taccgtgtgg tcagcgtcct caccgtcctg caccaggact ggctgaatgg caaggagtac  960
aagtgcaagg tctccaacaa agccctccca gcccccatcg agaaaaccat ctccaaagcc  1020
aaagggcagc cccgagaacc acaggtctac accctgcccc catcccggga ggagatgacc  1080
aagaaccagg tcagcctgac ctgcctggtc aaaggcttct atcccagcga catcgccgtg  1140
gagtgggaga gcaatgggca gccggagaac aactacaaga ccacgcctcc cgtgctggac  1200
tccgacggct ccttcttcct ctatagcaag ctcaccgtgg acaagagcag gtggcagcag  1260
gggaacgtct tctcatgctc cgtgatgcat gaggctctgc acaaccacta cacgcagaag  1320
agcttaagcc tgtctccggg ttga                                      1344

SEQ ID NO: 34          moltype = DNA  length = 651
FEATURE                Location/Qualifiers
source                 1..651
                       mol_type = other DNA
                       organism = synthetic construct
SEQUENCE: 34
cagtctgccc tgactcagcc tccctccgcg tccgggtctc ctggacagtc agtcaccatc  60
tcctgcactg gaaccagcag tgacgttggt ggttataact atgtctcctg gtaccaacag  120
cacccaggca aagcccccaa actcatgatt tatgaggtca ctaagcggcc ctcaggggtc  180
cctgatcgct tctctggctc caagtctggc aacacggcct ccctgaccgt ctctgggctc  240
caggctgagg atgaggctga ttattactgc acctcatatg caggcagcaa caaatatgtc  300
ttcggaactg ggaccaaggt caccgtccta ggtcagccca aggctgcccc ctcggtcact  360
ctgttcccgc cctcctctga ggagcttcaa gccaacaagg ccacactggt gtgtctcata  420
agtgacttct acccgggagc cgtgacagtg gcctggaagg cagatagcag ccccgtcaag  480
gcgggagtgg agaccaccac accctccaaa caaagcaaca acaagtacgc ggccagcagc  540
tacctgagcc tgacgcctga gcagtggaag tcccacagaa gctacagctg ccaggtcacg  600
catgaaggga gcaccgtgga gaagacagtg gcccctacag aatgttcata g         651

SEQ ID NO: 35          moltype = DNA  length = 1413
FEATURE                Location/Qualifiers
source                 1..1413
                       mol_type = other DNA
                       organism = synthetic construct
SEQUENCE: 35
caggtgcagt tggtgcaatc aggggctgaa gtcaaaaagc cagggtcttc cgttaaggtt  60
agctgcaaag catccggatt tgcctttacc gattactaca ttcactgggt caggcaagcg  120
ccaggtcagg gcctggaatg gatgggctgg attagtcccg gaaacgtgaa cactaagtat  180
aatgagaatt ttaaaggacg agtgactatc accgccgaca agtccacatc caccgcctat  240
atggagctgt cttcattgcg ctcggaggac acagctgttt actactgtgc ccgagatggc  300
tatagcctgt attactttga ctactggggc cagggtaccc ttgtcaccgt gctcgaggac  360
ctcaaaaatg tgtttccacc tgaggtggcc gtgtttgagc caagcgaatg tgaaatctct  420
cacacccaaa aagctacact tgtttgctta gcgaccggct tttatcctga tcatgtggag  480
ctctcatggt gggtcaacgg gaaggaggtc cattccggag tttgcaccga cccgcaaccc  540
ctcaaggagc agcctgccct ccaagatagc agatacgcac tttcatcacg gctgcgggtg  600
tctgctactt tttggcaaaa tcctcggaat cacttccgtt gccaagtaca gttctacggg  660
ctgtctgaga acgatgagtg gacccaggac agggccaagc ccgtgactca gattgtgtcg  720
gccgaagcat ggggtaggta tggtccccca tgcccaccat gcccagcacc tgaggccgcc  780
gggggaccat cagtcttcct gttcccccca aaacccaagg acactctcat gatctcccgg  840
acccctgagg tcacgtgcgt ggtggtggac gtgagccagg aagaccccga ggtccagttc  900
aactggtacg tggatggcgt ggaggtgcat aatgccaaga caaagccgcg ggaggagcag  960
ttcaacagca cgtaccgtgt ggtcagcgtc ctcaccgtcc tgcaccagga ctggctgaac  1020
ggcaaggagt acaagtgcaa ggtctccaac aaaggcctcc cgtcctccat cgagaaaacc  1080
atctccaaag ccaaagggca gccccgagag ccacaggtgt acaccctgcc cccatgccag  1140
gaggagatga ccaagaacca ggtcagcctg tggtgcctgg tcaaaggctt ctaccccagc  1200
gacatcgccg tggagtggga gagcaatggg cagccggaga acaactacaa gaccacgcct  1260
cccgtgctgg actccgacgg ctccttcttc ctctacagca ggctaaccgt ggacaagagc  1320
aggtggcagg aggggaatgt cttctcatgc tccgtgatgc atgaggctct gcacaaccac  1380
tacacacaga agagcctctc cctgtctctg ggc                            1413

SEQ ID NO: 36          moltype = DNA  length = 609
FEATURE                Location/Qualifiers
source                 1..609
                       mol_type = other DNA
                       organism = synthetic construct
```

-continued

```
SEQUENCE: 36
gacattgtga tgacacagag tcctgattct ctggctgtta gcctggggga acgagccaca  60
atcaactgca aatcgtcaca atcactcctc aatagcagaa cgcgcaagaa ttatttggcc  120
tggtatcaac aaaagccggg ccagccccca aagctcctga tctactgggc ttccacgcgg  180
cagtcgggcg tgccggatag gttcagtggc agtggctctg gaaccgattt caccctgaca  240
attagcagcc tgcaagccga ggacgtggct gtgtactact gcacacaaag ccacacactg  300
cggaccttcg gtggtggaac caaggtcgag atcaaacccg atattcaaaa ccccgaccct  360
gctgtatatc aactacggga cagcaagtct agtgataagt ctgtctgcct gttcactgac  420
ttcgatagtc agacccaggt atctcaaagc aaggactctg atgtgtacat aactgataaa  480
tgcgtgctgg acatgcggag catggatttt aaaagtaaca gtgccgtggc ctggtcgcaa  540
aagtcagact tcgcttgtgc caatgccttt caaaattcca tcattcctga ggataccttc  600
ttctgctct                                                          609

SEQ ID NO: 37          moltype = DNA  length = 1332
FEATURE                Location/Qualifiers
source                 1..1332
                       mol_type = other DNA
                       organism = synthetic construct
SEQUENCE: 37
gaggtgcagc tggtgcaaag tggagctgaa gtgaagaagc caggcgagtc cctcaagatt  60
tcctgcaagg ctagcggata ttcgttcaca acttattgga tcggatgggt taggcagatg  120
cctggcaagg gtcttgagct gatgggcatt atttatcctt atgactcgga cactaggtac  180
tccccaagct tccaaggcca ggttactatt agtgccgaca agagcattaa cactgcctat  240
ttgcaatgga gttctcttaa agccagtgat accgcaatgt attactgtgc tcgaatcacc  300
ggaggctacc tgtttgatta ctggggccaa ggcattctgg tgaccgtttc aagcgcaagc  360
accaaagggc caagcgtgtt cccacttgca ccttgttccc ggagcacctc cgagagcacg  420
gccgcgctgg gctgcttagt gaaagactac tttcctgagc cggtgacagt tagctggaat  480
tctggcgccc tgacatcagg agtccacacg ttcccggctg tactccaaag ctcaggcttg  540
tattctttgt cttctgtggt gaccgtgcct agtagctctc tcggaaccaa aacctatact  600
tgtaatgtag accataagcc aagcaatact aaagtggata aacgcgtcga gtccaaatac  660
ggaccaccat gtccccettg tcctgctcct gaggccgccg gtggacctag cgtatttctc  720
tttcctccta agcctaagga tactctgatg atatcgcgga ccccagaagt gacctgcgtg  780
gtggtagatg tcagtcagga agatcccgaa gtgcaattca attggtacgt ggatggagtt  840
gaggtgcaca acgccaagac taaaccccgt gaagagcaat tcaactctac ttaccgggtg  900
gtgtccgtgc ttaccgtgct acatcaagat tggctgaatg gaaaggagta caaatgtaaa  960
gtgtcaaata aggggctgcc ctctagcata gagaagacaa tctccaaggc taaggggcag  1020
ccaagggagc cccaagtctg cactcttcct cctagccaag aagagatgac caagaaccag  1080
gtgtctctga gctgtgctgt gaagggcttc tatcctagcg atattgcggt cgaatgggaa  1140
tccaacgggc agccagagaa caactacaag accacacccc ctgtgctcga ttccgacgga  1200
agctttttct tggtttcgag gctgactgtg gacaaatcaa ggtggcagga ggggaacgta  1260
ttttcgtgct ctgtgatgca tgaagctctg cacaaccact atactcaaaa atccctgtct  1320
ctgagcttgg gc                                                      1332

SEQ ID NO: 38          moltype = DNA  length = 648
FEATURE                Location/Qualifiers
source                 1..648
                       mol_type = other DNA
                       organism = synthetic construct
SEQUENCE: 38
caaagcgccc tcacgcaacc ccctagcgcg tctggctccc ctggacaaag cgtaacgata  60
tcttgtactg gtacctcttc tgacgttggc ggctataact atgtgtcttg gtatcaacaa  120
cacccaggca aagctcccaa gctgatgatt tacgaagtca ccaagcggcc cagcggagtg  180
cctgaccggt tctctggatc caaatctggg aacacagcat ccctcaccgt ttctggacta  240
caggcagagg atgaggccga ctattactgc acatcttacg ctggtagcaa taaatacgtt  300
tttgggacag gcaccaaagt gactgtgctt ggtcagccca aggctgcccc ctcggtcact  360
ctgttcccgc cctcctctga ggagcttcaa gccaacaagg ccacactggt gtgtctcata  420
agtgacttct acccgggagc cgtgacagtg gcctggaagg cagatagcag ccccgtcaag  480
gcgggagtgg agaccaccac accctccaaa caaagcaaca acaagtacgc ggccagcagc  540
tacctgagcc tgacgcctga gcagtggaag tcccacaaga gctacagctg ccaggtcacg  600
catgaaggga gcaccgtgga gaagacagtg gcccctacag aatgttca               648
```

PSMA ANTIBODIES AND USES THEREOF

CROSS-REFERENCE TO RELATED APPLICATIONS

This application is a continuation of International Patent Application No. PCT/CN2023/133153, filed Nov. 22, 2023, which claims the benefit of priority Patent Application No. PCT/CN2022/134047, filed Nov. 24, 2022, and priority Patent Application No. PCT/CN2022/134163, filed Nov. 24, 2022. The applications are incorporated by reference herein in their entirety.

REFERENCE TO SEQUENCE LISTING

The instant application contains a sequence listing which has been submitted electronically in XML format and is hereby incorporated by reference in its entirety. Said XML copy, created on Mar. 27, 2025, is named "CIE23B0133PCT-Sequence listing.xml" and is 47,840 bytes in size.

BRIEF SUMMARY

In one aspect, the present disclosure provides an isolated antibody or the antigen-binding portion thereof, comprising a prostate-specific membrane antigen (PSMA) binding moiety capable of binding to PSMA, wherein the PSMA binding moiety comprises: a heavy chain CDR1 comprising the sequence of SEQ ID NO: 1; a heavy chain CDR2 comprising the sequence of SEQ ID NO: 2; a heavy chain CDR3 comprising the sequence of SEQ ID NO: 3; a light chain CDR1 comprising the sequence of SEQ ID NO: 4; a light chain CDR2 comprising the sequence of SEQ ID NO: 5; and a light chain CDR3 comprising the sequence of SEQ ID NO: 6.

BRIEF DESCRIPTION OF THE DRAWINGS

In FIG. 10A, the lanes from left to right, show protein marker, non-reduced antibody, reduced antibody, and the protein marker, respectively.

(FIG. 22A) Tumor growth curve; and (FIG. 22B) Body weight of tumor bearing mice.

DETAILED DESCRIPTION

Figure 1:
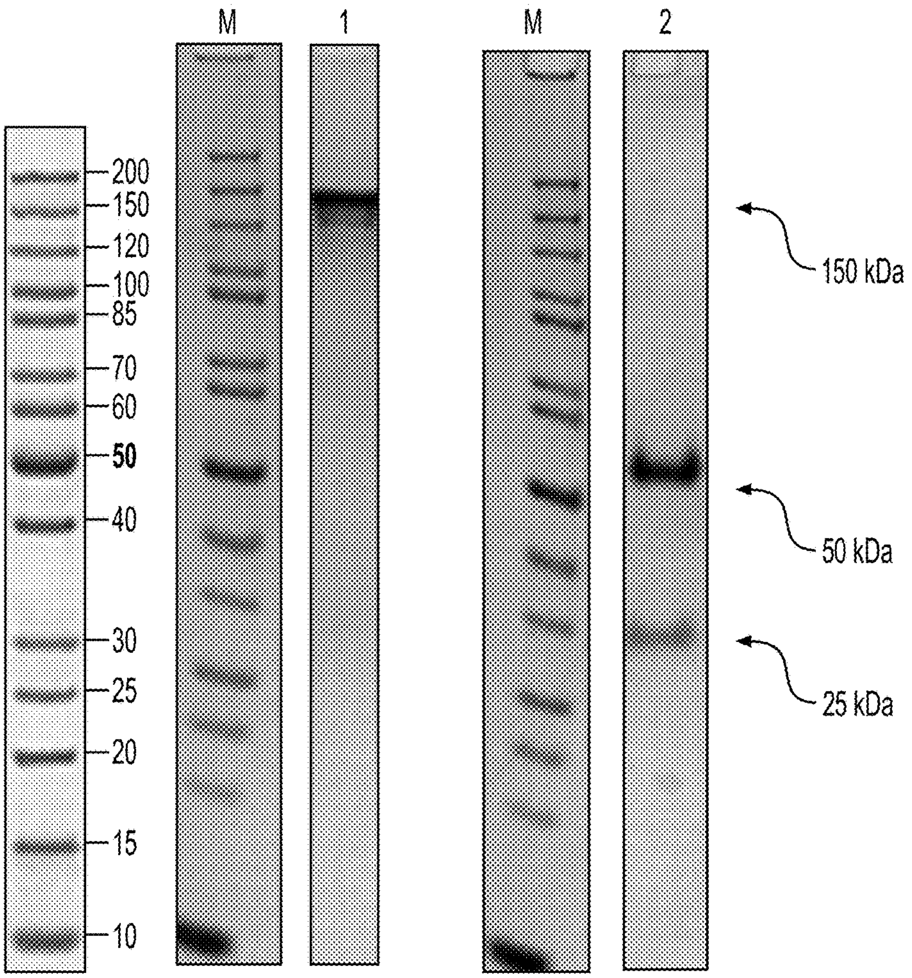
FIG. 1 shows SDS-PAGE and SEC-HPLC analysis of an exemplary PSMA antibody W305042.
Figure 1:
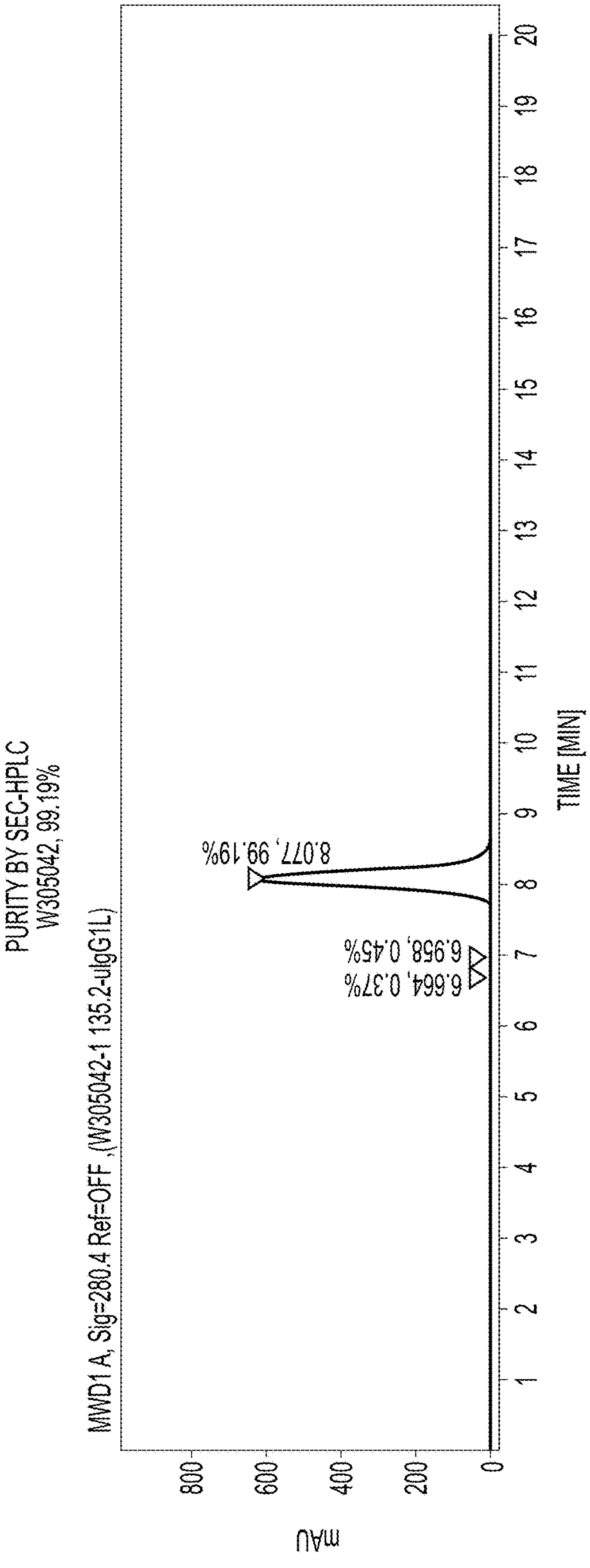

Unless otherwise defined herein, scientific and technical terms used in connection with the present disclosure shall have the meanings that are commonly understood by those of ordinary skill in the art. The singular forms "a," "an" and "the" can include plural referents unless the context clearly dictates otherwise. For example, reference to "a protein" includes a plurality of proteins; reference to "a cell" includes mixtures of cells, and the like. In this application, the use of "or" means "and/or" unless stated otherwise. Furthermore, the use of the term "comprising," as well as other forms, such as "comprises" and "comprised," is not limiting. In addition, ranges provided in the specification and appended claims include both end points and all points between the end points.

The terms "polypeptide," "peptide," and "protein" are used interchangeably herein to refer to a polymer of amino acid residues, or an assembly of multiple polymers of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refer to compounds that have the same basic chemical structure as a naturally occurring amino acid, i.e., an alpha-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. An alpha-carbon refers to the first carbon atom that attaches to a functional group, such as a carbonyl. A beta-carbon refers to the second carbon atom linked to the alpha-carbon, and the system continues naming the carbons in alphabetical order with Greek letters. Amino acid mimetics refers to chemical compounds that have a structure that is different from the general chemical structure of an amino acid, but that functions in a manner similar to a naturally occurring amino acid. The term "protein" typically refers to large polypeptides. The term "peptide" typically refers to short polypeptides. Polypeptide sequences are usually described as the left-hand end of a polypeptide sequence is the amino-terminus (N-terminus); the right-hand end of a polypeptide sequence is the carboxyl-terminus (C-terminus). "Polypeptide complex" as used herein refers to a complex comprising one or more polypeptides that are associated to perform certain functions. In some instances, the polypeptides are immune-related.

The term "antibody" or "Ab," herein is used in the broadest sense, which encompasses various antibody structures, including polyclonal antibodies, monospecific and multispecific antibodies (e.g., bispecific antibodies). A native intact antibody generally is a Y-shaped tetrameric protein comprising two heavy (H) and two light (L) polypeptide chains held together by covalent disulfide bonds and non-covalent interactions. Light chains of an antibody may be classified into κ and λ light chain. Heavy chains may be classified into μ, δ, γ, α and ε, which define isotypes of an antibody as IgM, IgD, IgG, IgA and IgE, respectively. In a light chain and a heavy chain, a variable region is linked to a constant region via a "J" region of about 12 or more amino acids, and a heavy chain further comprises a "D" region of about 3 or more amino acids. Each heavy chain consists of a heavy chain variable region/domain ($V_H$) and a heavy chain constant region/domain ($C_H$). A heavy chain constant region consists of 3 domains ($C_H1$, $C_H2$ and $C_H3$). Each light chain consists of a light chain variable region/domain ($V_L$) and a light chain constant region/domain ($C_L$). $V_H$ and $V_L$ region can further be divided into hypervariable regions (called complementary determining regions (CDR)), which are interspaced by relatively conservative regions (called framework region (FR)). Each $V_H$ and $V_L$ consists of 3 CDRs and 4 FRs in the following order: FR1, CDR1, FR2, CDR2, FR3, CDR3, FR4 from N-terminal to C-terminal. The variable region ($V_H$ and $V_L$) of each heavy/light chain pair forms antigen binding sites, respectively. Antibodies may be of different antibody isotypes, for example, IgG (e.g., IgG1, IgG2, IgG3 or IgG4 subtype), IgA1, IgA2, IgD, IgE or IgM antibody.

The term "antigen-binding portion" or "antigen-binding fragment" of an antibody, which can be interchangeably used in the context of the application, refers to polypeptides comprising fragments of a full-length antibody, which retain the ability of specifically binding to an antigen that the full-length antibody specifically binds to, and/or compete with the full-length antibody for binding to the same antigen. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein. In some instances, an antigen-binding fragment of an antibody may contain at least one variable domain covalently linked to at least one constant domain. The variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule.

The term "variable domain" with respect to an antibody as used herein refers to an antibody variable region or a fragment thereof comprising one or more CDRs. Although a variable domain may comprise an intact variable region (such as HCVR or LCVR), it is also possible to comprise less than an intact variable region yet still retains the capability of binding to an antigen or forming an antigen-binding site.

The term "antigen-binding moiety" as used herein refers to an antibody fragment formed from a portion of an antibody comprising one or more CDRs, or any other antibody fragment that binds to an antigen but does not comprise an intact native antibody structure. Examples of antigen-binding moiety include, without limitation, a variable domain, a variable region, a diabody, a Fab, a Fab', a $F(ab')_2$, an Fv fragment, a disulfide stabilized Fv fragment (dsFv), a $(dsFv)_2$, a bispecific dsFv (dsFv-dsFv'), a disulfide stabilized diabody (ds diabody), a multispecific antibody (e.g., a bispecific antibody such as Het-mAb), a camelized single domain antibody, a nanobody, a domain antibody, and a bivalent domain antibody. An antigen-binding moiety is capable of binding to the same antigen to which the parent antibody binds. In some instances, an antigen-binding moiety may comprise one or more CDRs from a particular human antibody grafted to a framework region from one or more different human antibodies.

"Fab" with regard to an antibody refers to that portion of the antibody consisting of a single light chain (both variable and constant regions) associating to the variable region and first constant region of a single heavy chain by a disulfide bond. In some instances, the constant regions of both the light chain and heavy chain are replaced with TCR constant regions.

"F(ab')$_2$" refers to a dimer of Fab'.

A "fragment difficult (Fd)" with regard to an antibody refers to the amino-terminal half of the heavy chain fragment that can be combined with the light chain to form Fab.

"Fc" with regard to an antibody refers to that portion of the antibody consisting of the second (CH2) and third (CH3) constant regions of a first heavy chain bound to the second and third constant regions of a second heavy chain via disulfide bonding. The Fc portion of the antibody is responsible for various effector functions such as ADCC, and CDC, but does not function in antigen binding.

"Hinge region" in terms of an antibody includes the portion of a heavy chain molecule that joins the CH1 domain to the CH2 domain. This hinge region comprises approximately 25 amino acid residues and is flexible, thus allowing the two N-terminus antigen binding regions to move independently.

"CH2 domain" as used herein refers to includes the portion of a heavy chain molecule that extends, e.g., from about amino acid 244 to amino acid 360 of an IgG antibody using conventional numbering schemes (amino acids 244 to 360, Kabat numbering system; and amino acids 231-340, EU numbering system).

The "CH3 domain" extends from the CH2 domain to the C-terminus of the IgG molecule and comprises approximately 108 amino acids. Certain immunoglobulin classes, e.g., IgM, further include a CH4 region.

"Fv" with regard to an antibody refers to the smallest fragment of the antibody to bear the complete antigen binding site. An Fv fragment consists of the variable domain of a single light chain bound to the variable domain of a single heavy chain. A number of Fv designs have been provided, including dsFvs, in which the association between the two domains is enhanced by an introduced disulphide bond; and scFvs can be formed using a peptide linker to bind the two domains together as a single polypeptide. Fvs constructs containing a variable domain of a heavy or light immunoglobulin chain associated to the variable and constant domain of the corresponding immunoglobulin heavy or light chain have also been produced. Fvs have also been multimerised to form diabodies and triabodies.

"Single-chain Fv antibody" or "scFv" refers to an engineered antibody consisting of a light chain variable region and a heavy chain variable region connected to one another directly or via a peptide linker sequence.

In some instances, an "scFv dimer" is a bivalent diabody or bivalent ScFv (BsFv) comprising $V_H$-$V_L$ (linked by a peptide linker) dimerized with another $V_H$-$V_L$ moiety such that $V_H$'s of one moiety coordinate with the $V_L$'s of the other moiety and form two binding sites which can target the same antigens (or epitopes) or different antigens (or epitopes).

In some instances, an "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

"ScFab" refers to a fusion polypeptide with a Fd linked to a light chain via a polypeptide linker, resulting in the formation of a single chain Fab fragment (scFab).

A "dsFv" refers to a disulfide-stabilized Fv fragment that the linkage between the variable region of a single light chain and the variable region of a single heavy chain is a disulfide bond. In some instances, a "(dsFv)$_2$" or "(dsFv-dsFv')" comprises three peptide chains: two $V_H$ moieties linked by a peptide linker (e.g., a long flexible linker) and bound to two $V_L$ moieties, respectively, via disulfide bridges. In some instances, dsFv-dsFv' is bispecific in which each disulfide paired heavy and light chain has a different antigen specificity.

"Appended IgG" refers to a fusion protein with a Fab arm fused to an IgG to form the format of bispecific (Fab)$_2$-Fc. It can form a "IgG-Fab" or a "Fab-IgG", with a Fab fused to the C-terminus or N-terminus of an IgG molecule with or without a connector. In some instances, the appended IgG can be further modified to a format of IgG-Fab$_4$.

The term "anti-CD3 antibody" or "CD3 antibody, as used herein, refers to an antibody, as defined herein, capable of binding to a CD3, for example a human CD3, for example for eliciting a potential therapeutic effect.

The terms "CD3" and "CD3 protein" are used interchangeably herein. The CD3 protein is present in virtually all T cells. The CD3-TCR complex modulates T cell functions in both innate and adoptive immune response, as well as cellular and humoral immune functions. These include eliminating pathogenic organisms and controlling tumor growth by broad range of cytotoxic effects. The CD3 T-cell co-receptor is a protein complex composed of four distinct chains, a CD3gamma chain, a CD3delta chain, and two CD3epsilon chains. The four chains associate with a molecule known as T-cell receptor (TCR) and the zeta-chain to generate activation signal in T lymphocytes. The TCR, zetachain, and CD3 molecules compose the TCR complex, in which TCR as a subunit recognizes and binds to antigen, and CD3 as a subunit transfers and conveys the antigen stimulation to signaling pathway, and ultimately regulates T-cell activity. The term "CD3" may include human CD3, as well as variants, isoforms, and species homologs thereof. Accordingly, an antibody or antigen-binding portion thereof, as defined and disclosed herein, may also bind CD3 from species other than human, for example cynomolgus CD3.

The term "human CD3," as used herein, refers to CD3 of human origin, such as the complete amino acid sequence of human CD3.

The term "cynomolgus CD3," as used herein, refers to CD3 derived from cynomolgus monkey, such as the complete amino acid sequence of Rhesus macaque CD3.

The term "anti-PSMA antibody," as used herein, refers to an antibody that specifically binds PSMA. An "anti-PSMA antibody" may include monovalent antibodies with a single specificity. Exemplary anti-PSMA antibodies are described elsewhere herein.

The term "Prostate-specific membrane antigen (PSMA)" is a type II membrane glycoprotein consisting of 750 amino acids with folate hydrolase and NAALADase enzymatic activities.

The term "bivalent," as used herein refers to an antibody or an antigen-binding fragment having two antigen-binding sites; the term "monovalent" refers to an antibody or an antigen-binding fragment having only one single antigen-binding site; and the term "multivalent" refers to an antibody or an antigen-binding fragment having multiple antigen-binding sites. In some instances, the antibody or antigen-binding portion thereof is bivalent.

As used herein, a "bispecific" antibody refers to an artificial antibody which is capable of binding to or targets two different epitopes, e.g., which has fragments derived from two different monoclonal antibodies. The binding of the bispecific antibody to the two different epitopes can elicit a potential therapeutic effect. The two different epitopes may present on the same antigen, or they may present on two different antigens. In some instances, the bispecific antibody is a Het-mAb.

As used herein, a "Het-mAb" is an IgG-like molecule that can target two different epitopes, either on the same or different targets, with 4 distinct chains; 2 heavy and 2 light. These chains contain a set of mutations in the Fc portion of the molecule to drive heavy chain dimerization and a set of mutations on the Fab portion to drive correct heavy/light pairing that form kappa/kappa or lambda/kappa subtype bispecific mAbs.

The term "bispecific antigen-binding molecule" means a protein, polypeptide or molecular complex comprising at least a first antigen-binding moiety (also referred to as a first antigen-binding site herein) and a second antigen-binding moiety (also referred to as a second antigen-binding site herein). In some instances, the "bispecific antigen-binding molecule" is a "bispecific antibody". Each antigen-binding moiety within the bispecific antibody comprises at least one CDR that alone, or in combination with one or more additional CDRs and/or FRs, specifically binds to a particular antigen. In some instances, the first antigen-binding site specifically binds to a first antigen (e.g., PSMA or CD3), and the second antigen-binding site specifically binds to a second, distinct antigen (e.g., CD3 or PSMA).

The terms "anti-PSMA/anti-CD3 antibody", "anti-PSMA/anti-CD3 bispecific antibody", "antibody against PSMA and CD3", "anti-PSMA×CD3 bispecific antibody", "PSMA×CD3 antibody", "anti-CD3/anti-PSMA antibody", "anti-CD3/anti-PSMA bispecific antibody", "antibody against CD3 and PSMA", "anti-CD3×PSMA bispecific antibody", "CD3×PSMA antibody", as used herein interchangeably, refer to a bispecific antibody that specifically binds to CD3 and PSMA, regardless of the order which target is mentioned first.

The term "monoclonal antibody" or "mAb", as used herein, refer to a preparation of antibody molecules of single molecular composition. A monoclonal antibody displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody," as used herein, refers to an antibody in which the variable region sequences are derived from one species and the constant region sequences are derived from another species, such as an antibody in which the variable region sequences are derived from a mouse antibody and the constant region sequences are derived from a human antibody.

The term "recombinant antibody," as used herein, refers to an antibody that is prepared, expressed, created or isolated by recombinant means, such as antibodies isolated from an animal that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

The term "spacer" as used herein refers to an artificial amino acid sequence having 1, 2, 3, 4 or 5 amino acid residues, or a length of between 5 and 15, 20, 30, 50 or more amino acid residues, joined by peptide bonds and are used to link one or more polypeptides. A spacer may or may not have a secondary structure. For example, a useful spacer in the present disclosure may be rich in glycine and proline residues. Examples include spacers having a single or repeated sequence(s) composed of threonine/serine and glycine, such as TGGGG, GGGGS or SGGGG or its tandem repeats (e.g., 2, 3, 4, or more repeats).

The term "operably link" or "operably linked" refers to a juxtaposition, with or without a spacer or linker, of two or more biological sequences of interest in such a way that they are in a relationship permitting them to function in an intended manner. When used with respect to polypeptides, it is intended to mean that the polypeptide sequences are linked in such a way that permits the linked product to have the intended biological function. For example, an antibody variable region may be operably linked to a constant region so as to provide for a stable product with antigen-binding activity. The term may also be used with respect to polynucleotides. For one instance, when a polynucleotide encoding a polypeptide is operably linked to a regulatory sequence (e.g., promoter, enhancer, silencer sequence, etc.), it is intended to mean that the polynucleotide sequences are linked in such a way that permits regulated expression of the polypeptide from the polynucleotide.

The term "epitope," as used herein, refers to a portion on antigen that an immunoglobulin or antibody specifically binds to. "Epitope" is also known as "antigenic determinant". Epitope or antigenic determinant generally consists of chemically active surface groups of a molecule such as amino acids, carbohydrates or sugar side chains, and generally has a specific three-dimensional structure and a specific charge characteristic. For example, an epitope generally comprises at least 3, 4, 5, 6, 7, 8, 9, 10, 11, 12, 13, 14 or 15 consecutive or non-consecutive amino acids in a unique steric conformation, which may be "linear" or "conformational". In a linear epitope, all the interaction sites between a protein and an interaction molecule (e.g., an antibody) are present linearly along the primary amino acid sequence of the protein. In a conformational epitope, the interaction sites span over amino acid residues that are separate from each other in a protein. For example, study on competition or cross-competition may be conducted to obtain antibodies that compete or cross-compete with each other for binding to antigens (e.g., RSV fusion protein). High-throughput methods for obtaining antibodies binding to the same epitope, which are based on their cross-competition.

The term "specific binding" or "specifically bind(s)" as used herein refers to a non-random binding reaction between two molecules, such as for example between an antibody and an antigen.

$K_D$ is used to refer to the ratio of the dissociation rate to the association rate ($k_{off}/k_{on}$), which may be determined by surface plasmon resonance method, microscale thermophoresis method, HPLC-MS method and flow cytometry (such as FACS) method. In some instances, the $K_D$ value can be appropriately determined by using flow cytometry.

The term "fusion" or "fused" when used with respect to amino acid sequences (e.g., peptide, polypeptide, or protein) refers to combination of two or more amino acid sequences, for example by chemical bonding or recombinant means, into a single amino acid sequence that does not exist naturally. A fusion amino acid sequence may be produced by genetic recombination of two encoding polynucleotide sequences and can be expressed by a method of introducing a construct containing the recombinant polynucleotides into a host cell.

The term "antigenic specificity" refers to a particular antigen or an epitope thereof that is selectively recognized by an antigen-binding molecule.

The term "identity," as used herein, refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) can be addressed by a particular mathematical model or computer program (i.e., an "algorithm").

The term "immunogenicity," as used herein, refers to ability of stimulating the formation of specific antibodies or sensitized lymphocytes in organisms. It not only refers to the property of an antigen to stimulate a specific immunocyte to activate, proliferate and differentiate so as to finally generate immunologic effector substance such as antibody and sensitized lymphocyte, but also refers to the specific immune response that antibody or sensitized T lymphocyte can be formed in immune system of an organism after stimulating the organism with an antigen. Immunogenicity is the most important property of an antigen. Whether an antigen can successfully induce the generation of an immune response in a host depends on three factors, properties of an antigen, reactivity of a host, and immunization means.

The term "substitution" with regard to amino acid residue as used herein refers to naturally occurring or induced replacement of one or more amino acids with another in a peptide, polypeptide, or protein. Substitution in a polypeptide may result in diminishment, enhancement, or elimination of the polypeptide's function.

The term "mutation" or "mutated" with regard to an amino acid residue as used herein refers to substitution, insertion, or addition of an amino acid residue.

A native "T cell receptor" or a native "TCR" is a heterodimeric T cell surface protein which is associated with invariant CD3 chains to form a complex capable of mediating signal transduction. TCR belongs to the immunoglobulin superfamily and is similar to a half antibody with a single heavy chain and a single light chain. a native TCR has an extracellular portion, a transmembrane portion, and an intracellular portion. The extracellular domain of a TCR has a membrane-proximal constant region and a membrane-distal variable region. In some instances, the bispecific antibodies comprise a soluble chimeric protein with the variable domains of an antibody and the constant domains of a TCR, wherein the subunits (such as alpha and beta domains) of the TCR constant domains are linked by an engineered disulfide bond.

The term "Ka," as used herein, is intended to refer to the association rate of a particular antibody-antigen interaction, whereas the term "Kd" as used herein, is intended to refer to the dissociation rate of a particular antibody-antigen interaction. Kd values for antibodies can be determined using methods well established in the art. The term "$K_D$" as used herein, is intended to refer to the dissociation constant of a particular antibody-antigen interaction, which is obtained from the ratio of Kd to Ka (i.e., Kd/Ka) and is expressed as a molar concentration (M). An exemplary method for determining the Kd of an antibody is by using surface plasmon resonance, such as using a biosensor system such as a BIACORE system.

The term "high affinity" for an IgG antibody, as used herein, refers to an antibody having a $K_D$ of $1\times10^{-7}$ M or less, for example $5\times10^{-8}$ M or less, $1\times10^{-8}$ M or less, $5\times10^{-9}$ M or less, or $1\times10^{-9}$ M or less for a target antigen.

The term "$EC_{50}$," as used herein, which is also termed as "half maximal effective concentration" refers to the concentration of a drug, antibody or toxicant which induces a response halfway between the baseline and maximum after a specified exposure time. In the context of the application, $EC_{50}$ is expressed in the unit of "nM".

The term "compete for binding," as used herein, refers to the interaction of two antibodies in their binding to a binding target. A first antibody competes for binding with a second antibody if binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not, be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope, whether to the same, greater, or lesser extent, the antibodies are said to "cross-compete" with each other for binding of their respective epitope(s).

The ability of "inhibit binding," as used herein, refers to the ability of an antibody or antigen-binding portion thereof to inhibit the binding of two molecules (e.g., human CD3/PSMA and human anti-CD3/anti-PSMA antibody) to any detectable level. In some instances, the binding of the two molecules can be inhibited at least 50% by the antibody or antigen-binding portion thereof. In some instances, such an inhibitory effect may be greater than 60%, greater than 70%, greater than 80%, or greater than 90%.

The term "isolated," as used herein, refers to a state obtained from natural state by artificial means. If a certain "isolated" substance or component is present in nature, it is possible because its natural environment changes, or the substance is isolated from natural environment, or both. For example, a certain un-isolated polynucleotide or polypeptide naturally exists in a certain living animal body, and the same polynucleotide or polypeptide with a high purity isolated from such a natural state is called isolated polynucleotide or polypeptide. The term "isolated" excludes neither the mixed artificial or synthesized substance nor other impure substances that do not affect the activity of the isolated substance.

The term "isolated antibody," as used herein, is intended to refer to an antibody that is substantially free of other antibodies having different antigenic specificities (e.g., an isolated antibody that specifically binds a CD3/PSMA protein is substantially free of antibodies that specifically bind antigens other proteins than CD3/PSMA). An isolated antibody that specifically binds a human CD3/PSMA protein may, however, have cross-reactivity to other antigens, such as CD3/PSMA proteins from other species. Moreover, an isolated antibody can be substantially free of other cellular material and/or chemicals.

The term "vector," as used herein, refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors can be plasmids, phages, cosmids, artificial chromosome such as yeast artificial chromosome (YAC), bacterial artificial chromosome (BAC) or P1-derived artificial chromosome (PAC); phage such as λ phage or M13 phage and animal virus. The animal viruses that can be used as vectors, include, but are not limited to, retrovirus (including lentivirus), adenovirus, adeno-associated virus, herpes virus (such as herpes simplex virus), pox virus, baculovirus, papillomavirus, papova virus (such as SV40). A vector may comprise multiple elements for controlling expression, including, but not limited to, a promoter sequence, a transcription initiation sequence, an enhancer sequence, a selection element and a reporter gene. In addition, a vector may comprise origin of replication.

The term "host cell," as used herein, refers to a cellular system which can be engineered to generate proteins, protein fragments, or peptides of interest. Host cells include, without limitation, cultured cells, e.g., mammalian cultured cells derived from rodents (rats, mice, guinea pigs, or hamsters) such as CHO, BHK, NSO, SP2/0, YB2/0; or human tissues or hybridoma cells, yeast cells, and insect cells, and cells comprised within a transgenic animal or cultured tissue. The term encompasses not only the particular subject cell but also the progeny of such a cell. Because certain modifications may occur in succeeding generations due to either mutation or environmental influences, such progeny may not be identical to the parent cell, but are still included within the scope of the term "host cell."

The term "transfection," as used herein, refers to the process by which nucleic acids are introduced into eukaryotic cells, particularly mammalian cells. Protocols and techniques for transfection include but not limited to lipid transfection and chemical and physical methods such as electroporation.

The term "SPR" or "surface plasmon resonance," as used herein, refers to and includes an optical phenomenon that allows for the analysis of real-time biospecific interactions by detection of alterations in protein concentrations within a biosensor matrix, for example using the BIACORE system (Pharmacia Biosensor AB, Uppsala, Sweden and Piscataway, N.J.).

The term "fluorescence-activated cell sorting" or "FACS," as used herein, refers to a specialized type of flow cytometry. It provides a method for sorting a heterogeneous mixture of biological cells into two or more containers, one cell at a time, based upon the specific light scattering and fluorescent characteristics of each cell. Instruments for carrying out FACS can include FACS STAR PLUS, FACSCAN and FACSORT instruments from Becton Dickinson (Foster City, Calif.) EPICS C from Coulter Epics Division (Hialeah, Fla.) and MOFLO from Cytomation (Colorado Springs, Colo.).

The term "subject" or "individual" or "animal" or "patient" as used herein refers to a human or non-human animal, including a mammal or a primate, in need of diagnosis, prognosis, amelioration, prevention, and/or treatment of a disease or condition. Mammalian subjects include humans, domestic animals, farm animals, and zoo, sports, or pet animals such as dogs, cats, guinea pigs, rabbits, rats, mice, horses, swine, cows, bears, and so on.

The term "effector functions" as used herein refer to biological activities attributable to the binding of Fc region of an antibody to its effectors such as C1 complex and Fc receptor. Exemplary effector functions include complement dependent cytotoxicity (CDC) induced by interaction of antibodies and C1q on the C1 complex; antibody-dependent cell-mediated cytotoxicity (ADCC) induced by binding of Fc region of an antibody to Fc receptor on an effector cell; and phagocytosis.

The term "antibody-dependent cell-mediated cytotoxicity" or "ADCC," as used herein, refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. In some instances, the antibodies "arm" the cytotoxic cells are required for such killing. The primary cells for mediating ADCC, NK cells, express FcγRIII only, whereas monocytes express FcγRI, FcγRII and FcγRIII. To assess ADCC activity of a molecule of interest, an in vitro ADCC assay. Useful effector cells for such assays include peripheral blood mononuclear cells (PBMC) and Natural Killer (NK) cells. In some instances, ADCC activity of the molecule of interest may be assessed in vivo.

The term "complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay may be performed.

The term "cancer" as used herein refers to any medical condition characterized by malignant cell growth or neoplasm, abnormal proliferation, infiltration or metastasis, and includes both solid tumors and non-solid cancers (hematologic malignancies) such as leukemia. As used herein "solid tumor" refers to a solid mass of neoplastic and/or malignant cells. Examples of cancer or tumors include hematological malignancies, oral carcinomas (for example of the lip, tongue or pharynx), digestive organs (for example esophagus, stomach, small intestine, colon, large intestine, or rectum), peritoneum, liver and biliary passages, pancreas, respiratory system such as larynx or lung (small cell and non-small cell), bone, connective tissue, skin (e.g., melanoma), breast, reproductive organs (fallopian tube, uterus, cervix, testicles, ovary, or prostate), urinary tract (e.g., bladder or kidney), brain and endocrine glands such as the thyroid. In some instances, the cancer is selected from ovarian cancer, breast cancer, head and neck cancer, renal cancer, bladder cancer, hepatocellular cancer, and colorectal cancer. In some instances, the cancer is selected from a lymphoma, Hodgkin's lymphoma, non-Hodgkin's lymphoma and B-cell lymphoma.

The term "treatment," "treating" or "treated," as used herein in the context of treating a condition, pertains generally to treatment and therapy, whether of a human or an animal, in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included. For cancer, "treating" may refer to dampen or slow the tumor or malignant cell growth, proliferation, or metastasis, or some combination thereof. For tumors, "treatment" includes removal of all or part of the tumor, inhibiting or slowing tumor growth and metastasis, preventing or delaying the development of a tumor, or some combination thereof.

The term "an effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen. For instance, the "an effective amount," when used in connection with treatment of CD3/PSMA-related diseases or conditions, refers to an antibody or antigen-binding portion thereof in an amount or concentration effective to treat the said diseases or conditions.

The term "prevent," "prevention" or "preventing," as used herein, with reference to a certain disease condition in a mammal, refers to preventing or delaying the onset of the disease, or preventing the manifestation of clinical or sub-clinical symptoms thereof.

The term "pharmaceutically acceptable," as used herein, means that the vehicle, diluent, excipient and/or salts thereof, are chemically and/or physically is compatible with other ingredients in the formulation, and the physiologically compatible with the recipient.

As used herein, the term "a pharmaceutically acceptable carrier and/or excipient" refers to a carrier and/or excipient pharmacologically and/or physiologically compatible with a subject and an active agent, and includes, but is not limited to pH adjuster, surfactant, adjuvant and ionic strength enhancer. For example, the pH adjuster includes, but is not limited to, phosphate buffer; the surfactant includes, but is not limited to, cationic, anionic, or non-ionic surfactant, e.g., Tween-80; the ionic strength enhancer includes, but is not limited to, sodium chloride.

As used herein, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminum adjuvants (for example, aluminum hydroxide), Freund's adjuvants (for example, Freund's complete adjuvant and Freund's incomplete adjuvant), *Coryne bacterium parvum*, lipopolysaccharide, cytokines, and the like.

Antibodies and Antigen-Binding Portions Thereof

The antibodies disclosed herein can bind to human PSMA and have one or more of the following properties:

(a) binding human PSMA with a $K_D$ of $1\times10^{-8}$ M or less;

(b) inducing production of a cytokine (e.g., IL-2 or IFN-γ) in $CD4^+$ T cells;

(c) enhancing proliferation of primary human $CD4^+$ T cells;

(d) enhancing proliferation of primary human $CD4^+$ T effector cells in the presence of Treg cells;

(e) binding human or rhesus monkey PSMA respectively; or (f) having no cross-reactivity to human CD40, CD137 and CD271.

The binding to PSMA can be assessed using ELISA. The binding specificity can be determined by monitoring binding of the antibody to cells expressing an PSMA protein, e.g., flow cytometry. For example, an antibody can be tested by a flow cytometry assay in which the antibody is reacted with a cell line that expresses human PSMA, such as CHO cells that have been transfected to express PSMA on their cell surface. The binding of the antibody, including the binding kinetics (e.g., $K_d$ value) can be tested in BIACORE binding assays. Still other suitable binding assays include ELISA assays, e.g., using a recombinant PSMA protein. For instance, the antibody can bind to a human PSMA with a $K_D$ of $1\times10^{-8}$ M or less, $1\times10^{-9}$ M or less, $5\times10^{-10}$ M or less, $2\times10^{-10}$ M or less, $1\times10^{-10}$ M or less, $5\times10^{-11}$ M or less, $3\times10^{-11}$ M or less, or $2\times10^{-11}$ M or less.

Variable regions and CDRs in an antibody sequence can be identified according to general rules that have been developed in the art (as set out above, such as, for example, the Kabat numbering system) or by aligning the sequences against a database of known variable regions. Exemplary databases of antibody sequences are described in, and can be accessed through, the "Abysis" website maintained by the Department of Biochemistry & Molecular Biology University College London, London, England and the VBASE2 website. Sequences can be analyzed using the Abysis database, which integrates sequence data from Kabat, IMGT and the Protein Data Bank (PDB) with structural data from the PDB. The Abysis database website further includes general rules that have been developed for identifying CDRs which can be used in accordance with the teachings herein. Unless otherwise indicated, CDR boundaries for antibodies are defined or identified by the conventions of Kabat and IMGT.

The percent identity between two amino acid sequences can be determined using the algorithm which has been incorporated into the ALIGN program (version 2.0), using a PAM120 weight residue table, a gap length penalty of 12 and a gap penalty of 4. In addition, the percentage of identity between two amino acid sequences can be determined by the algorithm which has been incorporated into the GAP program in the GCG software package, using either a BLOSSUM 62 matrix or a PAM250 matrix, and a gap weight of 16, 14, 12, 10, 8, 6, or 4 and a length weight of 1, 2, 3, 4, 5, or 6.

The protein sequences of the present disclosure can further be used as a "query sequence" to perform a search against public databases to, for example, identify related sequences. Such searches can be performed using the XBLAST program (version 2.0). BLAST protein searches can be performed with the XBLAST program, score=50, wordlength=3 to obtain amino acid sequences homologous to the antibody molecules of the disclosure. To obtain gapped alignments for comparison purposes, Gapped BLAST can be utilized. When utilizing BLAST and Gapped BLAST programs, the default parameters of the respective programs (e.g., XBLAST and NBLAST) can be used.

In some instances, the amino acid sequences of CDRs can be at least 90%, 91%, 92%, 93%, 94%, 95%, 96%, 97%, 98% or 99% identical to the respective sequences set forth above. In some instances, the amino acid sequences of the variable region can be at least 90%, 91%, 92%, 93%, 94%, 95%, 96%, 97%, 98% or 99% identical to the respective sequences set forth above.

In some instances, the CDRs of the isolated antibody or the antigen-binding portion thereof contain a conservative substitution of not more than 2 amino acids, or not more than 1 amino acid. The term "conservative substitution", as used herein, refers to amino acid substitutions which would not disadvantageously affect or change the essential properties of a protein/polypeptide comprising the amino acid sequence. For example, a conservative substitution may be introduced by site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue can be substituted with another amino acid residue from the same side-chain family.

In some instances, the first antigen-binding moiety and the second antigen-binding moiety of the bispecific antibody may be associated with one another via a knob-into-hole interaction.

In some instances, the first and/or the second antigen binding moiety is bivalent. The terms "bivalent" denotes the presence of two binding site respectively, in an antigen-binding molecule. This can provide for stronger binding to the antigen or the epitope than a monovalent counterpart. In some instances, in a bivalent antigen-binding moiety, the first valent of binding site and the second valent of binding site are structurally identical (i.e., having the same sequences).

In some instances, the antibodies and antigen-binding fragments thereof provided herein are bispecific. In some instances, the bispecific antibodies and antigen-binding portions thereof provided herein have a first specificity for PSMA, and a second specificity for a second antigen different from PSMA and whose blockade may produce a synergetic (e.g., synergistic) effect than blocking one antigen alone.

In some instances, the second specificity is for a tumor associated antigen or an epitope thereof. The term "tumor associated antigen" refers to a target antigen expressed by tumor cells, however, may be expressed by the cognate cell (or healthy cells) prior to transforming into a tumor. In some instances, the tumor associated antigens can be presented only by tumor cells and not by normal, i.e., non-tumor cells. In some instances, the tumor associated antigens can be exclusively expressed on tumor cells or may represent a tumor specific mutation compared to non-tumor cells. In some instances, the tumor associated antigens can be found in both tumor cells and non-tumor cells, but is overexpressed on tumor cells when compared to non-tumor cells or are accessible for antibody binding in tumor cells due to the less compact structure of the tumor tissue compared to non-tumor tissue. In some instances, the tumor associated antigen is located on the vasculature of a tumor.

Illustrative examples of a tumor associated antigen are LAG-3, CD10, CD19, CD20, CD22, CD21, CD22, CD25, CD30, CD33, CD34, CD37, CD44v6, CD45, CD133, Fms-like tyrosine kinase 3 (FLT-3, CD135), chondroitin sulfate proteoglycan 4 (CSPG4, melanoma-associated chondroitin sulfate proteoglycan), Epidermal growth factor receptor (EGFR), Her2neu, Her3, IGFR, IL3R, fibroblast activating protein (FAP), CDCP1, Derlin1, Tenascin, frizzled 1-10, the vascular antigens VEGFR2 (KDR/FLK1), VEGFR3 (FLT4, CD309), PDGFR-alpha (CD140a), PDGFR-beta (CD140b) Endoglin, CLEC14, Tem1-8, and Tie2. Further examples may include A33, CAMPATH-1 (CDw52), Carcinoembryonic antigen (CEA), Carboanhydrase IX (MN/CA IX), de2-7 EGFR, EGFRVIII, EpCAM, Ep-CAM, Folate-binding protein, G250, Fms-like tyrosine kinase 3 (FLT-3, CD135), c-Kit (CD117), CSFIR (CD115), HLA-DR, IGFR, IL-2 receptor, IL3R, MCSP (Melanoma-associated cell surface chondroitin sulphate proteoglycane), Muc-1, Prostate-specific membrane antigen (PSMA), Prostate stem cell antigen (PSCA), Prostate specific antigen (PSA), and TAG-72.

In some instances, the present disclosure includes a bispecific antibody or the antigen-binding portion thereof, comprising an antigen-binding site that specifically binds to CD3 and an antigen-binding site that specifically binds to PSMA. Such antibodies may be referred to herein as, e.g., "anti-CD3/anti-PSMA," or "anti-CD3/PSMA," or "anti-CD3×PSMA" or "CD3×PSMA" bispecific antibodies, or other similar terminology.

The bispecific antibody of the disclosure binds to human CD3 and human PSMA with high affinity. The binding of an antibody of the disclosure to CD3 or PSMA can be assessed using one or more techniques well established in the art, for instance, ELISA. The binding specificity of an antibody of the disclosure can also be determined by monitoring binding of the antibody to cells expressing a CD3 protein or an PSMA protein, e.g., flow cytometry. For example, an antibody can be tested by a flow cytometry assay in which the antibody is reacted with a cell line that expresses human CD3, such as CHO cells that have been transfected to express CD3 on their cell surface. In some instances, the binding of the antibody, including the binding kinetics (e.g., $K_D$ value) can be tested in BIACORE binding assays. Still other suitable binding assays include ELISA or FACS assays, for example using a recombinant CD3 protein.

In some instances, the bispecific antibody or an antigen-binding portion thereof of the disclosure comprises a CD3 binding moiety and an PSMA binding moiety, wherein the CD3 binding moiety comprises a chimeric Fab comprising a first heavy chain variable region of an anti-CD3 antibody operably linked to a first T cell receptor (TCR) constant region (C1), and a first light chain variable region of the anti-CD3 antibody operably linked to a second TCR constant region (C2), and wherein C1 and C2 are capable of forming a dimer via a non-native interchain disulphide bond which is capable of stabilizing the dimer, and the PSMA binding moiety comprises a Fab comprising a second heavy chain variable region of an anti-PSMA antibody operably linked to a heavy chain CH1 constant region domain, and a second light chain variable region of the anti-PSMA antibody operably linked to a light chain constant region, and wherein:

(A) the PSMA binding moiety comprises:
a heavy chain CDR1 comprising or consisting of SEQ ID NO: 1,
a heavy chain CDR2 comprising or consisting of SEQ ID NO: 2,
a heavy chain CDR3 comprising or consisting of SEQ ID NO: 3,
a light chain CDR1 comprising or consisting of SEQ ID NO: 4,
a light chain CDR2 comprising or consisting of SEQ ID NO: 5, and
a light chain CDR3 comprising or consisting of SEQ ID NO: 6,
and
(B) the CD3 binding moiety comprises:
a heavy chain CDR1 comprising or consisting of SEQ ID NO: 7,
a heavy chain CDR2 comprising or consisting of SEQ ID NO: 8,
a heavy chain CDR3 comprising or consisting of SEQ ID NO: 9,
a light chain CDR1 comprising or consisting of SEQ ID NO: 10,
a light chain CDR2 comprising or consisting of SEQ ID NO: 11, and
a light chain CDR3 comprising or consisting of SEQ ID NO: 12;
and/or
(A) the CD3 binding moiety comprises a heavy chain variable region comprising SEQ ID NO: 13 and a light chain variable region comprising SEQ ID NO: 14, and
(B) the PSMA binding moiety comprises a heavy chain variable region comprising SEQ ID NO: 15 and a light chain variable region comprising SEQ ID NO: 16.

In some instances, the bispecific antibody or the antigen-binding portion thereof has one or more of the following properties:

(a) specifically binding to human CD3 and PSMA protein simultaneously with a high affinity;
(b) specifically binding to human CD3 and/or cyno CD3 protein;
(c) specifically binding to human, mouse and/or cyno PSMA protein;
(d) capable of inducing potent T cell activation in the presence of PSMA-expression tumor cells compared to anti-CD3 antibodies, anti-PSMA antibodies, a combination thereof, and other bispecific antibodies targeting CD3 and PSMA;
(e) providing good thermal stability and being stable in human serum; and
(f) providing superior anti-tumor effect compared to anti-CD3 antibodies, anti-PSMA antibodies, a combination thereof, and other bispecific antibodies targeting CD3 and PSMA.

For instance, as studied in a tumor-bearing mice model, the bispecific antibody of the present disclosure achieved desirable tumor growth inhibition (TGI) as compared with the known anti-CD3 and anti-PSMA antibodies.

The Antigen-Binding Moiety that Specifically Binds to PSMA

The antigen-binding moiety provided herein specifically binds to PSMA and is also referred to as the PSMA binding moiety in the disclosure.

The antigen-binding moiety comprises a Fab comprising a heavy chain variable region of an anti-PSMA antibody operably linked to a heavy chain CH1 constant region domain, and a light chain variable region of the anti-PSMA antibody operably linked to a light chain constant region.

In some instances, the antigen-binding moiety comprises:

a heavy chain CDR1 comprising an amino acid sequence having at least 80%, at least 85%, at least 90%, at least 95%, at least 99% or even 100% sequence identity with SEQ ID NO: 1, or an amino acid sequence different from SEQ ID NO: 1 by an amino acid addition, deletion or substitution of not more than 2 amino acids,
a heavy chain CDR2 comprising an amino acid sequence having at least 80%, at least 85%, at least 90%, at least 95%, at least 99% or even 100% sequence identity with SEQ ID NO: 2, or an amino acid sequence different from SEQ ID NO: 2 by an amino acid addition, deletion or substitution of not more than 2 amino acids,
a heavy chain CDR3 comprising an amino acid sequence having at least 80%, at least 85%, at least 90%, at least 95%, at least 99% or even 100% sequence identity with SEQ ID NO: 3, or an amino acid sequence different from SEQ ID NO: 3 by an amino acid addition, deletion or substitution of not more than 1 amino acids,
a light chain CDR1 comprising an amino acid sequence having at least 80%, at least 85%, at least 90%, at least 95%, at least 99% or even 100% sequence identity with SEQ ID NO: 4, or an amino acid sequence different from SEQ ID NO: 4 by an amino acid addition, deletion or substitution of not more than 2 amino acids,
a light chain CDR2 comprising an amino acid sequence having at least 80%, at least 85%, at least 90%, at least 95%, at least 99% or even 100% sequence identity with SEQ ID NO: 5, or an amino acid sequence different from SEQ ID NO: 5 by an amino acid addition, deletion or substitution of not more than 1 amino acids, and
a light chain CDR3 comprising an amino acid sequence having at least 80%, at least 85%, at least 90%, at least 95%, at least 99% or even 100% sequence identity with SEQ ID NO: 6, or an amino acid sequence different from SEQ ID NO: 6 by an amino acid addition, deletion or substitution of not more than 1 amino acids.

In some instances, the antigen-binding moiety comprises:

a) a heavy chain CDR1 comprising an amino acid sequence represented by SEQ ID NO: 1,
b) a heavy chain CDR2 comprising an amino acid sequence represented by SEQ ID NO: 2,
c) a heavy chain CDR3 comprising an amino acid sequence represented by SEQ ID NO: 3,
d) a light chain CDR1 comprising an amino acid sequence represented by SEQ ID NO: 4,
e) a light chain CDR2 comprising an amino acid sequence represented by SEQ ID NO: 5, and
f) a light chain CDR3 comprising an amino acid sequence represented by SEQ ID NO: 6.

In some instances, the antigen-binding moiety comprises:

a) a heavy chain CDR1 consisting of an amino acid sequence represented by SEQ ID NO: 1,
b) a heavy chain CDR2 consisting of an amino acid sequence represented by SEQ ID NO: 2,
c) a heavy chain CDR3 consisting of an amino acid sequence represented by SEQ ID NO: 3,
d) a light chain CDR1 consisting of an amino acid sequence represented by SEQ ID NO: 4, e) a light chain CDR2 consisting of an amino acid sequence represented by SEQ ID NO: 5, and f) a light chain CDR3 consisting of an amino acid sequence represented by SEQ ID NO: 6.

In some instances, the heavy chain variable region of the antigen-binding moiety comprises:

(i) an amino acid sequence of SEQ ID NO: 15, and (ii) an amino acid sequence at least 85%, for example, 86%, 87%, 88%, 89%, 90%, 91%, 92%, 93%, 94%, 95%, 96%, 97%, 98%, or 99% identical to SEQ ID NO: 15 and at the same time maintaining the binding specificity to PSMA (e.g., containing the CDRs disclosed above); or (iii) an amino acid sequence with addition, deletion and/or substitution of one or more amino acids (e.g., 1 to 18, 1 to 15, 1 to 10, or 1 to 5) compared with SEQ ID NO: 15 and at the same time maintaining the binding specificity to PSMA (e.g., containing the CDRs disclosed above).

In some instances, the light chain variable region of the antigen-binding moiety comprises:

(i) an amino acid sequence of SEQ ID NO: 16, and (ii) an amino acid sequence at least 85%, for example, 86%, 87%, 88%, 89%, 90%, 91%, 92%, 93%, 94%, 95%, 96%, 97%, 98%, or 99% identical to SEQ ID NO: 16 and at the same time maintaining the binding specificity to PSMA (e.g., containing the CDRs disclosed above); or (iii) an amino acid sequence with addition, deletion and/or substitution of one or more amino acids (e.g., 1 to 16, 1 to 15, 1 to 10, or 1 to 5) compared with SEQ ID NO: 16 and at the same time maintaining the binding specificity to PSMA (e.g., containing the CDRs disclosed above).

In some instances, the heavy chain variable region of the antigen-binding moiety consists of an amino acid sequence of SEQ ID NO: 15, and the light chain variable region of the antigen-binding moiety consists of an amino acid sequence of SEQ ID NO: 16.

In some instances, the heavy chain variable region of the PSMA binding moiety is operably linked to a hinge-Fc region, such as a human IgG Fc region, especially a human IgG4 or IgG1 Fc region, e.g., a human IgG4 Fc region containing S228P mutation, Fc null mutations (F234A L235A) and hole mutations (Y349C-T366S-L368A-Y407V). In some instances, to construct the CD3×PSMA bispecific antibody, DNA sequence encoding the VH region of anti-CD3 antibody is fused to a modified TCR beta constant domain and the hinge-Fc region of human IgG4 with S228P mutation, Fc null mutations (F234A L235A) and knob mutations (S354C-T366W); DNA sequence encoding the VL region of anti-CD3 antibody is fused to a modified TCR alpha constant domain; DNA sequence encoding VH region of anti-PSMA antibody is fused to the hinge-Fc region of human IgG4 with S228P mutation, Fc null mutations (F234A L235A) and hole mutations (Y349C-T366S-L368A-Y407V); DNA sequence encoding VL region of anti-PSMA antibody is fused to CL domain.

In some instances, the antigen-binding moiety comprises two polypeptide chains:

i) a second heavy chain comprising an amino acid sequence having at least 85%, for example, 86%, 87%, 88%, 89%, 90%, 91%, 92%, 93%, 94%, 95%, 96%, 97%, 98%, 99%, or even 100% sequence identity to SEQ ID NO: 19 and at the same time maintaining the binding specificity to PSMA (e.g., containing the CDRs or/and variable regions disclosed above); and ii) a second light chain comprising or an amino acid sequence having at least 85%, for example, 86%, 87%, 88%, 89%, 90%, 91%, 92%, 93%, 94%, 95%, 96%, 97%, 98%, 99%, or even 100% sequence identity to SEQ ID NO: 20 and at the same time maintaining the binding specificity to PSMA (e.g., containing the CDRs or/and variable regions disclosed above).

In some instances, the antigen-binding moiety comprises two polypeptide chains:

i) a second heavy chain represented by SEQ ID NO: 19; and ii) a second light chain represented by SEQ ID NO: 20.

In some instances, the antigen-binding moiety consists of two polypeptide chains:

i) a second heavy chain represented by SEQ ID NO: 19; and ii) a second light chain represented by SEQ ID NO: 20.

In some instances, the antigen-binding moiety comprises two polypeptide chains:

i) a second heavy chain comprising an amino acid sequence having at least 85%, for example, 86%, 87%, 88%, 89%, 90%, 91%, 92%, 93%, 94%, 95%, 96%, 97%, 98%, 99%, or even 100% sequence identity to SEQ ID NO: 31 and at the same time maintaining the binding specificity to PSMA (e.g., containing the CDRs or/and variable regions disclosed above); and ii) a second light chain comprising or an amino acid sequence having at least 85%, for example, 86%, 87%, 88%, 89%, 90%, 91%, 92%, 93%, 94%, 95%, 96%, 97%, 98%, 99%, or even 100% sequence identity to SEQ ID NO: 32 and at the same time maintaining the binding specificity to PSMA (e.g., containing the CDRs or/and variable regions disclosed above).

In some instances, the antigen-binding moiety comprises two polypeptide chains:

i) a second heavy chain represented by SEQ ID NO: 31; and ii) a second light chain represented by SEQ ID NO: 32.

In some instances, the antigen-binding moiety consists of two polypeptide chains:

i) a second heavy chain represented by SEQ ID NO: 31; and ii) a second light chain represented by SEQ ID NO: 32.

The Antigen-Binding Moiety that Specifically Binds to CD3

The antigen-binding moiety specifically binds to CD3, and thus, it is also referred to as the CD3 binding moiety in the disclosure. The two terms can be used interchangeably.

The antigen-binding moiety comprises a chimeric Fab comprising a heavy chain variable region of an anti-CD3 antibody operably linked to a first T cell receptor (TCR) constant region (C1), and a light chain variable region of the anti-CD3 antibody operably linked to a second TCR constant region (C2), and wherein C1 and C2 are capable of forming a dimer via a non-native interchain disulphide bond which is capable of stabilizing the dimer.

In some instances, the antigen-binding moiety comprises:

a) a heavy chain CDR1 comprising an amino acid sequence having at least 80%, at least 85%, at least 90%, at least 95%, at least 99% or even 100% sequence identity with SEQ ID NO: 7, or an amino acid sequence different from SEQ ID NO: 7 by an amino acid addition, deletion or substitution of not more than 2 amino acids, b) a heavy chain CDR2 comprising an amino acid sequence having at least 80%, at least 85%, at least 90%, at least 95%, at least 99% or even 100% sequence identity with SEQ ID NO: 8, or an amino acid sequence different from SEQ ID NO: 8 by an amino acid addition, deletion or substitution of not more than 2 amino acids, c) a heavy chain CDR3 comprising an amino acid sequence having at least 80%, at least 85%, at least 90%, at least 95%, at least 99% or even 100% sequence identity with SEQ ID NO: 9, or an amino acid sequence different from SEQ ID NO: 9 by an amino acid addition, deletion or substitution of not more than 2 amino acids, d) a light chain CDR1 comprising an amino acid sequence having at least 80%, at least 85%, at least 90%, at least 95%, at least 99% or even 100% sequence identity with SEQ ID NO: 10, or an amino acid sequence different from SEQ ID NO: 10 by an amino acid addition, deletion or substitution of not more than 2 amino acids, e) a light chain CDR2 comprising an amino acid sequence having at least 80%, at least 85%, at least 90%, at least 95%, at least 99% or even 100% sequence identity with SEQ ID NO: 11, or an amino acid sequence different from SEQ ID NO: 11 by an amino acid addition, deletion or substitution of not more than 1 amino acids, and f) a light chain CDR3 comprising an amino acid sequence having at least 80%, at least 85%, at least 90%, at least 95%, at least 99% or even 100% sequence identity with SEQ ID NO: 12, or an amino acid sequence different from SEQ ID NO: 12 by an amino acid addition, deletion or substitution of not more than 1 amino acids.

In some instances, the antigen-binding moiety comprises:

a) a heavy chain CDR1 comprising an amino acid sequence represented by SEQ ID NO: 7, b) a heavy chain CDR2 comprising an amino acid sequence represented by SEQ ID NO: 8, c) a heavy chain CDR3 comprising an amino acid sequence represented by SEQ ID NO: 9, d) a light chain CDR1 comprising an amino acid sequence represented by SEQ ID NO: 10, e) a light chain CDR2 comprising an amino acid sequence represented by SEQ ID NO: 11, and f) a light chain CDR3 comprising an amino acid sequence represented by SEQ ID NO: 12.

In some instances, the antigen-binding moiety comprises:

a) a heavy chain CDR1 consisting of an amino acid sequence represented by SEQ ID NO: 7, b) a heavy chain CDR2 consisting of an amino acid sequence represented by SEQ ID NO: 8, c) a heavy chain CDR3 consisting of an amino acid sequence represented by SEQ ID NO: 9, d) a light chain CDR1 consisting of an amino acid sequence represented by SEQ ID NO: 10, e) a light chain CDR2 consisting of an amino acid sequence represented by SEQ ID NO: 11, and f) a light chain CDR3 consisting of an amino acid sequence represented by SEQ ID NO: 12.

In some instances, the heavy chain variable region of the antigen-binding moiety comprises:

(i) an amino acid sequence of SEQ ID NO: 13, and (ii) an amino acid sequence at least 85%, for example, 86%, 87%, 88%, 89%, 90%, 91%, 92%, 93%, 94%, 95%, 96%, 97%, 98%, or 99% identical to SEQ ID NO: 13 and at the same time maintaining the binding specificity to CD3 (e.g., containing the CDRs disclosed above); or (iii) an amino acid sequence with addition, deletion and/or substitution of one or more amino acids (e.g., 1 to 18, 1 to 15, 1 to 10, or 1 to 5) compared with SEQ ID NO: 13 and at the same time maintaining the binding specificity to CD3 (e.g., containing the CDRs disclosed above).

In some instances, the light chain variable region of the antigen-binding moiety comprises:

(i) an amino acid sequence of SEQ ID NO: 14, and (ii) an amino acid sequence at least 85%, for example, 86%, 87%, 88%, 89%, 90%, 91%, 92%, 93%, 94%, 95%, 96%, 97%, 98%, or 99% identical to SEQ ID NO: 14 and at the same time maintaining the binding specificity to CD3 (e.g., containing the CDRs disclosed above); or (iii) an amino acid sequence with addition, deletion and/or substitution of one or more amino acids (e.g., 1 to 17, 1 to 15, 1 to 10, or 1 to 5) compared with SEQ ID NO: 14 and at the same time maintaining the binding specificity to CD3 (e.g., containing the CDRs disclosed above).

In some instances, the heavy chain variable region of the antigen-binding moiety comprises or consists of an amino acid sequence of SEQ ID NO: 13, and the light chain variable region of the antigen-binding moiety comprises or consists of an amino acid sequence of SEQ ID NO: 14.

In some instances, the antigen-binding moiety comprises two polypeptide chains:

i) a first heavy chain comprising an amino acid sequence having at least 85%, for example, 86%, 87%, 88%, 89%, 90%, 91%, 92%, 93%, 94%, 95%, 96%, 97%, 98%, 99%, or even 100% sequence identity to SEQ ID NO: 17 and at the same time maintaining the binding specificity to CD3 (e.g., containing the CDRs or/and variable regions disclosed above); and ii) a first light chain comprising an amino acid sequence having at least 85%, for example, 86%, 87%, 88%, 89%, 90%, 91%, 92%, 93%, 94%, 95%, 96%, 97%, 98%, 99%, or even 100% sequence identity to SEQ ID NO: 18 and at the same time maintaining the binding specificity to CD3 (e.g., containing the CDRs or/and variable regions disclosed above).

In some instances, the antigen-binding moiety comprises two polypeptide chains:

i) a first heavy chain represented by SEQ ID NO: 17; and ii) a first light chain represented by SEQ ID NO: 18.

In some instances, the antigen-binding moiety consists of two polypeptide chains:

i) a first heavy chain represented by SEQ ID NO: 17; and ii) a first light chain represented by SEQ ID NO: 18.

In some aspects, the heavy chain variable region of the antigen-binding moiety is operably linked to C1 and a hinge-Fc region, such as a human IgG Fc region, especially a human IgG4 or IgG1 Fc region, e.g., a human IgG4 Fc region containing S228P mutation, Fc null mutations (F234A L235A), knob mutations (S354C-T366W), and/or hole mutations (Y349C-T366S-L368A-Y407V). In some instances, a VH region is fused to a modified TCR beta constant domain and the hinge-Fc region of human IgG4 with S228P mutation, Fc null mutations (F234A L235A) and knob mutations (S354C-T366W). In some instances, a VH region is fused to the hinge-Fc region of human IgG4 with S228P mutation, Fc null mutations (F234A L235A) and hole mutations (Y349C-T366S-L368A-Y407V).

TCR Constant Region

Human TCR beta chain constant region has two different variants, known as TRBC1 and TRBC2 (IMGT nomenclature). In the present disclosure, the sequence of wild type TCR beta domain is with the NCBI accession number of A0A5B9. The modified TCR beta constant domain in the present disclosure is:

(SEQ ID NO: 29)
DLKNVFPPEVAVFEPSECEISHTQKATLVCLATGFYPDHVELSWWVNGK

EVHSGVCTDPQPLKEQPALQDSRYALSSRLRVSATFWQNPRNHFRCQVQ

FYGLSENDEWTQDRAKPVTQIVSAEAWGR.

In some instances, a first T cell receptor (TCR) constant region (C1) comprises a modified TCRβ constant region comprising the amino acid sequence of SEQ ID NO: 29, and in some instances, C1 comprises or consists of a modified TCRβ constant region represented by SEQ ID NO: 29.

Human TCR alpha chain constant region is known as TRAC, with the NCBI accession number of P01848. The modified TCR alpha constant domain in the present disclosure is:

(SEQ ID NO: 30)
PDIQNPDPAVYQLRDSKSSDKSVCLFTDFDSQTQVSQSKDSDVYITDKC

VLDMRSMDFKSNSAVAWSQKSDFACANAFQNSIIPEDTFFCS.

In some instances, a second T cell receptor (TCR) constant region (C2) comprises a modified TCRα constant region comprising the amino acid sequence of SEQ ID NO: 30, and in some instances, C2 comprises or consists of a modified TCRα constant region represented by SEQ ID NO: 30.

In the present disclosure, the first and the second TCR constant regions of the polypeptide complexes provided herein are capable of forming a dimer comprising, between the TCR constant regions, at least one non-native interchain bond that is capable of stabilizing the dimer.

The term "dimer" as used herein refers to an associated structure formed by two molecules, such as polypeptides or proteins, via covalent or non-covalent interactions. A homodimer or homodimerization is formed by two identical molecules, and a heterodimer or heterodimerization is formed by two different molecules. The dimer formed by the first and the second TCR constant regions is a heterodimer.

An interchain bond is formed between one amino acid residue on one TCR constant region and another amino acid residue on the other TCR constant region. In some instances, the non-native interchain bond can be any bond or interaction that is capable of associating two TCR constant regions into a dimer. Examples of suitable non-native interchain bond include, a disulphide bond, a hydrogen bond, electrostatic interaction, a salt bridge, or hydrophobic-hydrophilic interaction, a knobs-into-holes or the combination thereof.

A "disulphide bond" refers to a covalent bond with the structure R—S—S—R'. The amino acid cysteine comprises a thiol group that can form a disulphide bond with a second thiol group, for example from another cysteine residue. The disulphide bond can be formed between the thiol groups of two cysteine residues residing respectively on the two polypeptide chains, thereby forming an interchain bridge or interchain bond.

A "non-native" interchain bond as used herein refers to an interchain bond which is not found in a native association of the native counterpart TCR constant regions. For example, a non-native interchain bond can be formed between a mutated amino acid residue and a native amino acid residue, each residing on a respective TCR constant region; or alternatively between two mutated amino acid residues residing respectively on the TCR constant regions. In some instances, the at least one non-native interchain bond is formed between a first mutated residue comprised in the first TCR constant region and a second mutated residue comprised in the second TCR constant region of the polypeptide complex.

The term "contact interface" as used herein refers to the particular region(s) on the polypeptides where the polypeptides interact/associate with each other. A contact interface comprises one or more amino acid residues that are capable of interacting with the corresponding amino acid residue(s) that comes into contact or association when interaction occurs. The amino acid residues in a contact interface may or may not be in a consecutive sequence. For example, when the interface is three-dimensional, the amino acid residues within the interface may be separated at different positions on the linear sequence.

Generation of Hybridomas Producing Antibodies

To generate hybridomas producing the antibodies disclosed herein, for instance human monoclonal antibodies, splenocytes and/or lymph node cells from immunized mice can be isolated and fused to an appropriate immortalized cell line, such as a mouse myeloma cell line. The resulting hybridomas can be screened for the production of antigen-specific antibodies.

Generation of Transfectomas Producing Antibodies

Antibodies of the present disclosure can also be produced in a host cell transfectoma using, for example, a combination of recombinant DNA techniques and gene transfection methods. In some instances, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The antibody light chain gene and the antibody heavy chain gene can be inserted into the same or separate expression vectors. In some instances, the variable regions are used to create full-length antibody genes of any antibody isotype by inserting them into expression vectors already encoding heavy chain constant and light chain constant regions of the desired isotype such that the heavy chain variable domain is operatively linked to the CH segment(s) within the vector and the heavy chain variable domain is operatively linked to the CL segment within the vector. The recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is possible to express the antibodies of the invention in either prokaryotic or eukaryotic host cells, for example, mammalian host cells, which can assemble and secrete a properly folded and immunologically active antibody.

Mammalian host cells for expressing the recombinant antibodies of the invention include Chinese Hamster Ovary (CHO cells), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, secretion of the antibody into the culture medium in which the host cells are grown. Antibodies can be recovered from the culture medium using standard protein purification methods.

Generation of Bispecific Antibodies

The bispecific antibodies and antigen-binding fragments provided herein can be made with any suitable methods, e.g., two immunoglobulin heavy chain-light chain pairs can be co-expressed in a host cell to produce bispecific antibodies in a recombinant way, followed by purification by affinity chromatography.

Recombinant approach may also be used, where sequences encoding the antibody heavy chain variable domains for the two specificities are respectively fused to immunoglobulin constant domain sequences, followed by insertion to an expression vector which is co-transfected with an expression vector for the light chain sequences to a suitable host cell for recombinant expression of the bispecific antibody. Similarly, scFv dimers can also be recombinantly constructed and expressed from a host cell.

In another method, leucine zipper peptides from the Fos and Jun proteins can be linked to the Fab' portions of two different antibodies by gene fusion. The linked antibodies are reduced at the hinge region to four half antibodies (i.e., monomers) and then re-oxidized to form heterodimers.

The two antigen-binding sites may also be conjugated or cross-linked to form a bispecific antibody or antigen-binding fragment. For example, one antibody can be coupled to biotin while the other antibody to avidin, and the strong association between biotin and avidin would complex the two antibodies together to form a bispecific antibody.

Bispecific antigen-binding fragments may be generated from a bispecific antibody, for example, by proteolytic cleavage, or by chemical linking. For example, an antigen-binding fragment (e.g., Fab$^{5}$) of an antibody may be prepared and converted to Fab'-thiol derivative and then mixed and reacted with another converted Fab$^{5}$ derivative having a different antigenic specificity to form a bispecific antigen-binding fragment.

Nucleic Acid Molecules Encoding the Antibody of the Disclosure

In some aspects, the disclosure is directed to an isolated nucleic acid molecule, comprising a nucleic acid sequence encoding the bispecific antibody or the antigen-binding portion as disclosed herein, e.g., the nucleic acid sequence comprises any combination of the heavy chain or light chain sequences of SEQ ID NOs: 35 to 38 such as SEQ ID NOs: 35 and 36, or SEQ ID NOs: 37 and 38. For example, the nucleic acid sequence may encode the heavy chain and/or the light chain of the bispecific antibody, e.g., the nucleic acid sequence comprises all the sequences of SEQ ID NOs: 35 to 38.

An isolated nucleic acid molecule encoding the heavy chain variable region of the CD3 binding moiety may comprise a nucleic acid sequence selected from:

(A) a nucleic acid sequence that encodes the heavy chain variable region as set forth in SEQ ID NO: 13;
(B) a nucleic acid sequence as set forth in SEQ ID NO: 21; or
(C) a nucleic acid sequence that hybridized under high stringency conditions to the complementary strand of the nucleic acid sequence of (A) or (B).

An isolated nucleic acid molecule encoding the light chain variable region of the CD3 binding moiety may comprise a nucleic acid sequence selected from:

(A) a nucleic acid sequence that encodes the light chain variable region as set forth in SEQ ID NO: 14;
(B) a nucleic acid sequence as set forth in SEQ ID NO: 22; or
(C) a nucleic acid sequence that hybridized under high stringency conditions to the complementary strand of the nucleic acid sequence of (A) or (B).

An isolated nucleic acid molecule encoding the heavy chain variable region of the PSMA binding moiety may comprise a nucleic acid sequence selected from:

(A) a nucleic acid sequence that encodes the heavy chain variable region as set forth in SEQ ID NO: 15;
(B) a nucleic acid sequence as set forth in SEQ ID NO: 23; or
(C) a nucleic acid sequence that hybridized under high stringency conditions to the complementary strand of the nucleic acid sequence of (A) or (B).

An isolated nucleic acid molecule encoding the light chain variable region of the PSMA binding moiety may comprise a nucleic acid sequence selected from:

(A) a nucleic acid sequence that encodes light chain variable region as set forth in SEQ ID NO: 16;
(B) a nucleic acid sequence as set forth in SEQ ID NO: 24; or
(C) a nucleic acid sequence that hybridized under high stringency conditions to the complementary strand of the nucleic acid sequence of (A) or (B).

In some instances, the present disclosure provides an isolated nucleotide sequence encoding the heavy chain of the CD3 binding moiety, wherein the isolated nucleotide sequence encoding the heavy chain of the CD3 binding moiety comprises or consists of:

(A) a nucleic acid sequence that encodes the heavy chain as set forth in SEQ ID NO: 17;
(B) a nucleic acid sequence as set forth in SEQ ID NO: 25 or 35; or
(C) a nucleic acid sequence that hybridized under high stringency conditions to the complementary strand of the nucleic acid sequence of (A) or (B).

In some instances, the present disclosure provides an isolated nucleotide sequence encoding the light chain of the CD3 binding moiety, wherein the isolated nucleotide sequence encoding the light chain of the CD3 binding moiety comprises or consists of:

(A) a nucleic acid sequence that encodes the light chain as set forth in SEQ ID NO: 18;
(B) a nucleic acid sequence as set forth in SEQ ID NO: 26 or 36; or
(C) a nucleic acid sequence that hybridized under high stringency conditions to the complementary strand of the nucleic acid sequence of (A) or (B).

In some instances, the present disclosure provides an isolated nucleotide sequence encoding the heavy chain of the PSMA binding moiety, wherein the isolated nucleotide sequence encoding the heavy chain of the PSMA binding moiety comprises or consists of:

(A) a nucleic acid sequence that encodes the heavy chain as set forth in SEQ ID NO: 19;

(B) a nucleic acid sequence as set forth in SEQ ID NO: 27 or 37; or (C) a nucleic acid sequence that hybridized under high stringency conditions to the complementary strand of the nucleic acid sequence of (A) or (B).

In some instances, the present disclosure provides an isolated nucleotide sequence encoding the light chain of the PSMA binding moiety, wherein the isolated nucleotide sequence encoding the light chain of the PSMA binding moiety comprises or consists of:

(A) a nucleic acid sequence that encodes the light chain as set forth in SEQ ID NO: 20;

(B) a nucleic acid sequence as set forth in SEQ ID NO: 28 or 38; or (C) a nucleic acid sequence that hybridized under high stringency conditions to the complementary strand of the nucleic acid sequence of (A) or (B).

In some instances, the present disclosure provides an isolated nucleotide sequence encoding the heavy chain of the PSMA binding moiety, wherein the isolated nucleotide sequence encoding the heavy chain of the PSMA binding moiety comprises or consists of:

(A) a nucleic acid sequence of SEQ ID NO: 33;

(B) a nucleic acid sequence that encodes the amino acid sequence of SEQ ID NO: 31; or (C) a nucleic acid sequence that hybridized under high stringency conditions to the complementary strand of the nucleic acid sequence of (A) or (B).

In some instances, the present disclosure provides an isolated nucleotide sequence encoding the light chain of the PSMA binding moiety, wherein the isolated nucleotide sequence encoding the light chain of the PSMA binding moiety comprises or consists of:

(A) a nucleic acid sequence of SEQ ID NO: 34;

(B) a nucleic acid sequence that encodes the amino acid sequence of SEQ ID NO: 32; or (C) a nucleic acid sequence that hybridized under high stringency conditions to the complementary strand of the nucleic acid sequence of (A) or (B).

In some aspects, the disclosure is directed to a vector comprising the nucleic acid sequence as disclosed herein. In some instances, the expression vector further comprises a nucleotide sequence encoding the constant region of a bispecific antibody.

A vector in the context of the present disclosure may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In some instances, a CD3 or a PSMA antibody-encoding nucleic acid is comprised in a naked DNA or RNA vector, including, for example, a linear expression element, a compacted nucleic acid vector, a plasmid vector such as pBR322, pUC 19/18, or pUC 118/119, a "midge" minimally-sized nucleic acid vector, or as a precipitated nucleic acid vector construct, such as a CaP04-precipitated construct.

In some instances, the vector is suitable for expression of the anti-CD3 antibody and/or anti-PSMA antibody in a bacterial cell. Examples of such vectors include expression vectors such as BlueScript (Stratagene), pIN vectors, pET vectors (Novagen, Madison WI) and the like). A vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH.

A vector may also or alternatively be a vector suitable for expression in mammalian cells, e.g., a vector comprising glutamine synthetase as a selectable marker.

A nucleic acid and/or vector may also comprise a nucleic acid sequence encoding a secretion/localization sequence, which can target a polypeptide, such as a nascent polypeptide chain, to the periplasmic space or into cell culture media. Such sequences can include secretion leader or signal peptides.

The vector may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE.

In an even further aspect, the disclosure relates to a host cell comprising the vector specified herein above.

Thus, the present disclosure also relates to a recombinant eukaryotic or prokaryotic host cell which produces a bispecific antibody of the present disclosure, such as a transfectoma.

The CD3-specific antibody may be expressed in a recombinant eukaryotic or prokaryotic host cell, such as a transfectoma, which produces an antibody of the disclosure as defined herein or a bispecific antibody of the disclosure as defined herein. The PSMA-specific antibody may likewise be expressed in a recombinant eukaryotic or prokaryotic host cell, such as a transfectoma, which produces an antibody of the disclosure as defined herein or a bispecific antibody of the disclosure as defined herein.

Examples of host cells include yeast, bacterial, plant and mammalian cells, such as CHO, CHO-S, HEK, HEK293, HEK-293F, Expi293F, PER.C6 or NSO cells or lymphocytic cells. For example, in some instances, the host cell may comprise a first and second nucleic acid construct stably integrated into the cellular genome. In some instances, the present disclosure provides a cell comprising a non-integrated nucleic acid, such as a plasmid, cosmid, phagemid, or linear expression element, which comprises a first and second nucleic acid construct as specified above.

In an even further aspect, the disclosure relates to a transgenic non-human animal or plant comprising nucleic acids encoding one or two sets of a human heavy chain and a human light chain, wherein the animal or plant produces a bispecific antibody of the disclosure.

In a further aspect, the disclosure relates to a hybridoma which produces an antibody for use in a bispecific antibody of the disclosure as defined herein. In an even further aspect, the disclosure relates to a transgenic non-human animal or plant comprising nucleic acids encoding one or two sets of a human heavy chain and a human light chain, wherein the animal or plant produces an antibody for use in a bispecific antibody or a bispecific antibody of the disclosure.

In one aspect, the disclosure relates to an expression vector comprising:

(i) a nucleic acid sequence encoding a heavy chain variable region of the first antigen-binding moiety and/or a heavy chain variable region of the second antigen-binding moiety according to any one of the instances or embodiments disclosed herein, optionally, further encoding the CH1 domain or CL domain;

(ii) a nucleic acid sequence encoding a light chain variable region of the first antigen-binding moiety and/or a light chain variable region of the second antigen-binding moiety according to any one of the instances or embodiments disclosed herein;

(iii) a nucleic acid sequence encoding the modified TCR beta constant domain or the modified TCR alpha constant domain;

(iv) a nucleic acid sequence encoding a Fc region;

(v) a nucleic acid sequence encoding a linker; or (vi) the combinations of at least two of the above.

In one aspect, the disclosure relates to a nucleic acid construct encoding one or more amino acid sequences set forth in the sequence listing.

In one aspect, the disclosure relates to a method for producing a bispecific antibody according to any one of the instances or embodiments as disclosed herein, comprising the steps of culturing a host cell as disclosed herein comprising an expression vector or more than one expression vectors as disclosed herein expressing the bispecific antibody as disclosed herein and purifying said antibody from the culture media. In one aspect, the disclosure relates to a host cell comprising an expression vector as defined above. In some instances, the host cell is a recombinant eukaryotic, recombinant prokaryotic, or recombinant microbial host cell.

Pharmaceutical Compositions

In some aspects, the disclosure is directed to a pharmaceutical composition comprising at least one antibody or antigen-binding portion thereof as disclosed herein and a pharmaceutically acceptable carrier.

Components of the Compositions

The pharmaceutical composition may optionally contain one or more additional pharmaceutically active ingredients, such as another antibody or a drug. The pharmaceutical compositions of the disclosure also can be administered in a combination therapy with, for example, another immune-stimulatory agent, anti-cancer agent, an antiviral agent, or a vaccine, such that the anti-CD3/anti-PSMA bispecific antibody enhances the immune response against the vaccine. A pharmaceutically acceptable carrier can include, for example, a pharmaceutically acceptable liquid, gel or solid carriers, an aqueous medium, a non-aqueous medium, an anti-microbial agent, isotonic agents, buffers, antioxidants, anesthetics, suspending/dispersing agent, a chelating agent, a diluent, adjuvant, excipient or a nontoxic auxiliary substance, other various combinations of components or more.

Suitable components may include, for example, antioxidants, fillers, binders, disintegrating agents, buffers, preservatives, lubricants, flavorings, thickening agents, coloring agents, emulsifiers or stabilizers such as sugars and cyclodextrin. Suitable anti-oxidants may include, for example, methionine, ascorbic acid, EDTA, sodium thiosulfate, platinum, catalase, citric acid, cysteine, mercapto glycerol, thioglycolic acid, Mercapto sorbitol, butyl methyl anisole, butylated hydroxy toluene and/or propylgalacte. As disclosed in the present disclosure, in a solvent containing an antibody or an antigen-binding fragment of the present disclosure discloses compositions include one or more anti-oxidants such as methionine, reducing antibody or antigen binding portion thereof may be oxidized. The oxidation reduction may prevent or reduce a decrease in binding affinity, thereby enhancing antibody stability and extended shelf life. In some instances, the present disclosure provides a composition comprising one or more antibodies or antigen binding portion thereof and one or more anti-oxidants such as methionine. The present disclosure further provides a variety of methods, wherein an antibody or antigen binding portion thereof is mixed with one or more anti-oxidants, such as methionine, so that the antibody or antigen binding portion thereof can be prevented from oxidation, to extend their shelf life and/or increased activity.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethyl celluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetra-acetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

Administration, Formulation and Dosage

The pharmaceutical composition of the disclosure may be administered to a subject in need thereof, by various routes, including, but not limited to, oral, intravenous, intra-arterial, subcutaneous, parenteral, intranasal, intramuscular, intracranial, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

Suitable formulations for enteral administration include hard or soft gelatin capsules, pills, tablets, including coated tablets, elixirs, suspensions, syrups or inhalations and controlled release forms thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilizers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Similarly, the particular dosage regimen, including dose, timing and repetition, will depend on the particular individual and that individual's medical history, as well as empirical considerations such as pharmacokinetics (e.g., half-life, clearance rate, etc.).

Frequency of administration may be determined and adjusted over the course of therapy, and is based on reducing the number of proliferative or tumorigenic cells, maintaining the reduction of such neoplastic cells, reducing the proliferation of neoplastic cells, or delaying the development of metastasis. In some instances, the dosage administered may be adjusted or attenuated to manage potential side effects and/or toxicity. Alternatively, sustained continuous release formulations of a subject therapeutic composition may be appropriate.

In some instances, the antibody or the antigen binding portion thereof of the disclosure may be administered in suitable ranges, which can include about 5 μg/kg body weight to about 100 mg/kg body weight per dose; about 50 μg/kg body weight to about 5 mg/kg body weight per dose; about 100 μg/kg body weight to about 10 mg/kg body weight per dose. Other ranges can include about 100 μg/kg body weight to about 20 mg/kg body weight per dose and about 0.5 mg/kg body weight to about 20 mg/kg body weight per dose. In some instances, the dosage is at least about 100 μg/kg body weight, at least about 250 μg/kg body weight, at least about 750 μg/kg body weight, at least about 3 mg/kg body weight, at least about 5 mg/kg body weight, at least about 10 mg/kg body weight per dose.

In some instances, the course of treatment involving the antibody or the antigen-binding portion thereof of the instant disclosure will comprise multiple doses of the selected drug product over a period of weeks or months. More specifically, the antibody or the antigen-binding portion thereof of the instant disclosure may be administered once every day, every two days, every four days, every week, every ten days, every two weeks, every three weeks, every month, every six weeks, every two months, every ten weeks or every three months. In this regard, it will be appreciated that the dosages may be altered, or the interval may be adjusted based on patient response and clinical practices.

Dosages and regimens may also be determined empirically for the disclosed therapeutic compositions in individuals who have been given one or more administration(s). For example, individuals may be given incremental dosages of a therapeutic composition produced as described herein. In some instances, the dosage may be gradually increased or reduced or attenuated based respectively on empirically determined or observed side effects or toxicity. To assess efficacy of the selected composition, a marker of the specific disease, disorder or condition can be followed as described previously. For cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or a tumorigenic antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

Compatible formulations for parenteral administration (e.g., intravenous injection) will comprise the antibody or antigen-binding portion thereof as disclosed herein in concentrations of from about 10 μg/ml to about 100 mg/ml. In some instances, the concentrations of the antibody or the antigen binding portion thereof will comprise 20 μg/ml, 40 μg/ml, 60 μg/ml, 80 μg/ml, 100 μg/ml, 200 μg/ml, 300, μg/ml, 400 μg/ml, 500 μg/ml, 600 μg/ml, 700 μg/ml, 800 μg/ml, 900 μg/ml or 1 mg/ml. In some instances, ADC concentrations will comprise 2 mg/ml, 3 mg/ml, 4 mg/ml, 5 mg/ml, 6 mg/ml, 8 mg/ml, 10 mg/ml, 12 mg/ml, 14 mg/ml, 16 mg/ml, 18 mg/ml, 20 mg/ml, 25 mg/ml, 30 mg/ml, 35 mg/ml, 40 mg/ml, 45 mg/ml, 50 mg/ml, 60 mg/ml, 70 mg/ml, 80 mg/ml, 90 mg/ml or 100 mg/ml.

Medical Uses/Methods

In some aspects, the present disclosure provides a method of treating a disorder in a subject, which comprises administering to the subject (e.g., a mammal for example a human) in need of treatment a therapeutically effective amount of the antibody or antigen-binding portion thereof as disclosed herein. For example, the disorder is a cancer.

A variety of cancers where PSMA is implicated, whether malignant or benign and whether primary or secondary, may be treated or prevented with a method provided by the disclosure. The cancers may be solid cancers. Examples of such cancers include lung cancers such as bronchogenic carcinoma (e.g., squamous cell carcinoma, small cell carcinoma, large cell carcinoma, and adenocarcinoma), alveolar cell carcinoma, bronchial adenoma, chondromatous hamartoma (noncancerous), and sarcoma (cancerous); a kidney cancer; a breast cancer; a gastric cancer; a colorectal cancer; glioblastoma; a prostate cancer; pancreatic cancers; or ovarian cancer. In some instances, the cancer is a prostate cancer, especially metastatic castration-resistant prostate cancer (mCRPC).

Combined Use with Chemotherapies

The antibody or the antigen-binding portion thereof may be used in combination with an anti-cancer agent, a cytotoxic agent or chemotherapeutic agent.

The term "anti-cancer agent" or "anti-proliferative agent" means any agent that can be used to treat a cell proliferative disorder such as cancer, and includes, but is not limited to, cytotoxic agents, cytostatic agents, anti-angiogenic agents, debulking agents, chemotherapeutic agents, radiotherapy and radiotherapeutic agents, targeted anti-cancer agents, BRMs, therapeutic antibodies, cancer vaccines, cytokines, hormone therapies, radiation therapy and anti-metastatic agents and immunotherapeutic agents. It will be appreciated that, in some instances as discussed above, such anti-cancer agents may comprise conjugates and may be associated with the disclosed site-specific antibodies prior to administration. More specifically, in some instances selected anti-cancer agents will be linked to the unpaired cysteines of the engineered antibodies to provide engineered conjugates as set forth herein. Accordingly, such engineered conjugates are expressly contemplated as being within the scope of the instant disclosure. In some instances, the disclosed anti-cancer agents will be given in combination with site-specific conjugates comprising a different therapeutic agent as set forth above.

As used herein the term "cytotoxic agent" means a substance that is toxic to the cells and decreases or inhibits the function of cells and/or causes destruction of cells. In some instances, the substance is a naturally occurring molecule derived from a living organism. Examples of cytotoxic agents include, but are not limited to, small molecule toxins or enzymatically active toxins of bacteria (e.g., Diptheria toxin, *Pseudomonas* endotoxin and exotoxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, *Aleurites fordii* proteins, dianthin proteins, *Phytolacca* mericana proteins (PAPI, PAPII, and PAP-S), *Momordica charantia* inhibitor, curcin, crotin, hlorambu *officinalis* inhibitor, gelonin, mitegellin, restrictocin, phenomycin, neomycin, and the tricothecenes) or animals, (e.g., cytotoxic Rnases, such as extracellular pancreatic Rnases; Dnase I, including fragments and/or variants thereof).

For the purposes of the instant disclosure a "chemotherapeutic agent" comprises a chemical compound that non-specifically decreases or inhibits the growth, proliferation, and/or survival of cancer cells (e.g., cytotoxic or cytostatic agents). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous or generate tumorigenic progeny (e.g., TIC). Such agents are often administered, and are often most effective, in combination, e.g., in regimens such as CHOP or FOLFIRI.

Examples of anti-cancer agents that may be used in combination with the site-specific constructs of the present disclosure (either as a component of a site specific conjugate or in an unconjugated state) include, but are not limited to, abiraterone, apalutamide, bicalutamide, alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, esperamicin, chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, erlotinib, vemurafenib, crizotinib,sorafenib, ibrutinib, enzalutamide, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, PSK polysaccharide complex (JHS Natural Products, Eugene, OR), razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; GEMZAR gemcitabine; 6-thioguanine; mercaptopurine; methotrexate; platinum analogs, vinblastine; platinum; etoposide (VP-16); ifosfamide; mitoxantrone; vincristine; NAVELBINE vinorelbine; novantrone; teniposide; edatrexate; daunomycin; aminopterin; xeloda; ibandronate; irinotecan (Camptosar, CPT-11), topoisomerase inhibitor RFS 2000; difluorometlhylornithine; retinoids; capecitabine; combretastatin; leucovorin; oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN rIL-2; LURTOTECAN topoisomerase 1 inhibitor; ABARELIX rmRH; Vinorelbine and Esperamicins and pharmaceutically acceptable salts, acids or derivatives of any of the above.

Combined Use with Radiotherapies

The present disclosure also provides for the combination of the antibody or the antigen-binding portion thereof with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and the disclosed conjugates may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

Pharmaceutical Packs and Kits

Pharmaceutical packs and kits comprising one or more containers, comprising one or more doses of the antibody or the antigen-binding portion thereof are also provided. In some instances, a unit dosage is provided wherein the unit dosage contains a predetermined amount of a composition comprising, for example, the antibody or the antigen-binding portion thereof, with or without one or more additional agents. In some instances, such a unit dosage is supplied in single-use prefilled syringe for injection. In some instances, the composition contained in the unit dosage may comprise saline, sucrose, or the like; a buffer, such as phosphate, or the like; and/or be formulated within a stable and effective pH range. Alternatively, in some instances, the conjugate composition may be provided as a lyophilized powder that may be reconstituted upon addition of an appropriate liquid, for example, sterile water or saline solution. In some instances, the composition comprises one or more substances that inhibit protein aggregation, including, but not limited to, sucrose and arginine. Any label on, or associated with, the container(s) indicates that the enclosed conjugate composition is used for treating the neoplastic disease condition of choice.

The present disclosure also provides kits for producing single-dose or multi-dose administration units of site-specific conjugates and, optionally, one or more anti-cancer agents. The kit comprises a container and a label or package insert on or associated with the container. Suitable containers include, for example, bottles, vials, syringes, etc. The containers may be formed from a variety of materials such as glass or plastic and contain a pharmaceutically effective amount of the disclosed conjugates in a conjugated or unconjugated form. In some instances, the container(s) comprise a sterile access port (for example the container may be an intravenous solution bag or a vial having a stopper pierceable by a hypodermic injection needle). Such kits will generally contain in a suitable container a pharmaceutically acceptable formulation of the engineered conjugate and, optionally, one or more anti-cancer agents in the same or different containers. The kits may also contain other pharmaceutically acceptable formulations, either for diagnosis or combined therapy. For example, in addition to the antibody or the antigen-binding portion thereof of the disclosure such kits may contain any one or more of a range of anti-cancer agents such as chemotherapeutic or radiotherapeutic drugs; anti-angiogenic agents; anti-metastatic agents; targeted anti-cancer agents; cytotoxic agents; and/or other anti-cancer agents.

More specifically the kits may have a single container that contains the disclosed the antibody or the antigen-binding portion thereof, with or without additional components, or they may have distinct containers for each desired agent. Where combined therapeutics are provided for conjugation, a single solution may be pre-mixed, either in a molar equivalent combination, or with one component in excess of the other. Alternatively, the conjugates and any optional anti-cancer agent of the kit may be maintained separately within distinct containers prior to administration to a patient.

The kits may also comprise a second/third container means for containing a sterile, pharmaceutically acceptable buffer or other diluent such as bacteriostatic water for injection (BWFI), phosphate-buffered saline (PBS), Ringer's solution and dextrose solution.

When the components of the kit are provided in one or more liquid solutions, the liquid solution may be an aqueous solution, e.g., a sterile aqueous or saline solution. However, the components of the kit may be provided as dried powder (s). When reagents or components are provided as a dry powder, the powder can be reconstituted by the addition of a suitable solvent. It is envisioned that the solvent may also be provided in another container.

As indicated briefly above the kits may also contain a means by which to administer the antibody or the antigen-binding portion thereof and any optional components to a patient, e.g., one or more needles, I.V. bags or syringes, or even an eye dropper, pipette, or other such like apparatus, from which the formulation may be injected or introduced into the animal or applied to a diseased area of the body. The kits of the present disclosure will also typically include a means for containing the vials, or such like, and other component in close confinement for commercial sale, such as, e.g., injection or blow-molded plastic containers into which the desired vials and other apparatus are placed and retained.

Illustrative Antibodies

One illustrative antibody is an anti-CD3/anti-PSMA bispecific antibody designated as W308051-T3U5.E17-61.uIgG4V322, or W308051. The CDR numbering is defined using IMGT+Kabat, covering all the residues defined by both IMGT and Kabat.

Amino Acid Sequences of W308051 CDRs

| Moiety | portion | CDR1 | CDR2 | CDR3 |
|---|---|---|---|---|
| U5 (anti-PSMA arm) | Heavy chain CDR | SEQ ID NO: 1<br>GYSFTTYWIG | SEQ ID NO: 2<br>IIYPYDSDTRYSPSFQG | SEQ ID NO: 3<br>ITGGYLFDY |
| | Light chain CDR | SEQ ID NO: 4<br>TGTSSDVGGYNYVS | SEQ ID NO: 5<br>EVTKRPS | SEQ ID NO: 6<br>TSYAGSNKYV |
| T3 (anti-CD3 arm) | Heavy chain CDR | SEQ ID NO: 7<br>GFAFTDYYIH | SEQ ID NO: 8<br>WISPGNVNTKYNENFKG | SEQ ID NO: 9<br>DGYSLYYFDY |
| | Light chain CDR | SEQ ID NO: 10<br>KSSQSLLNSRTRKNYLA | SEQ ID NO: 11<br>WASTRQS | SEQ ID NO: 12<br>TQSHTLRT |

Amino Acid Sequences of W308051 Variable Regions

| Moiety | VH (heavy chain variable region) | VL (light chain variable region) |
|---|---|---|
| T3<br>(anti-CD3 arm) | SEQ ID NO: 13<br>**QVQLVQSGAEVKKPGSSVKVSCK**<br>**AS**GFAFTDYYIH**WVRQAPGQGLE**<br>**WMG**WISPGNVNTKYNENFKG**RVT**<br>**ITADKSTSTAYMELSSLRSEDTAV**<br>**YYCAR**DGYSLYYFDY**WGQGTLVT**<br>**VLE** | SEQ ID NO: 14<br>**DIVMTQSPDSLAVSLGERATINC**<br>KSSQSLLNSRTRKNYLA**WYQQKP**<br>**GQPPKLLIY**WASTRQS**GVPDRFS**<br>**GSGSGTDFTLTISSLQAEDVAVY**<br>**YC**TQSHTLRT**FGGGTKVEIK** |
| U5<br>(anti-PSMA arm) | SEQ ID NO: 15<br>**EVQLVQSGAEVKKPGESLKISCK**<br>**AS**GYSFTTYWIG**WVRQMPGKGLE**<br>**LMG**IIYPYDSDTRYSPSFQG**QVTIS**<br>**ADKSINTAYLQWSSLKASDTAMY**<br>**YCAR**ITGGYLFDY**WGQGILVTVSS** | SEQ ID NO: 16<br>**QSALTQPPSASGSPGQSVTISC**TG<br>TSSDVGGYNYVS**WYQQHPGKAP**<br>**KLMIY**EVTKRPS**GVPDRFSGSKS**<br>**GNTASLTVSGLQAEDEADYYC**T<br>SYAGSNKYV**FGTGTKVTVL** |

Note:

VH and VL are in a format of FR1-CDR1-FR2-CDR2-FR3-CDR3-FR4 from N-terminus to C-terminus, with FRs in bold and CDRs underlined.

Amino Acid Sequences of W308051 Heavy Chain and Light Chain

| moiety | Heavy chain | Light chain |
|---|---|---|
| T3<br>(anti-CD3 arm) | SEQ ID NO: 17<br>QVQLVQSGAEVKKPGSSVKVSCK<br>ASGFAFTDYYIHWVRQAPGQGLE<br>WMGWISPGNVNTKYNENFKGRVT<br>ITADKSTSTAYMELSSLRSEDTAV<br>YYCARDGYSLYYFDYWGQGTLVT<br>VLEDLKNVFPPEVAVFEPSECEISHT<br>QKATLVCLATGFYPDHVELSWWVNG<br>KEVHSGVCTDPQPLKEQPALQDSRYA<br>LSSRLRVSATFWQNPRNHFRCQVQFY<br>GLSENDEWTQDRAKPVTQIVSAEAWG<br>RYGPPCPPCPAPEAAGGPSVFLFPPK<br>PKDTLMISRTPEVTCVVVDVSQEDP<br>EVQFNWYVDGVEVHNAKTKPREE<br>QFNSTYRVVSVLTVLHQDWLNGKE<br>YKCKVSNKGLPSSIEKTISKAKGQP<br>REPQVYTLPPCQEEMTKNQVSLWC<br>LVKGFYPSDIAVEWESNGQPENNY<br>KTTPPVLDSDGSFFLYSRLTVDKSR<br>WQEGNVFSCSVMHEALHNHYTQK<br>SLSLSLG | SEQ ID NO: 18<br>DIVMTQSPDSLAVSLGERATINC<br>KSSQSLLNSRTRKNYLAWYQQKP<br>GQPPKLLIYWASTRQSGVPDRFS<br>GSGSGTDFTLTISSLQAEDVAVY<br>YCTQSHTLRTFGGGTKVEIKPDI<br>QNPDPAVYQLRDSKSSDKSVCLFTD<br>FDSQTQVSQSKDSDVYITDKCVLDM<br>RSMDFKSNSAVAWSQKSDFACANAF<br>QNSIIPEDTFFCS |
| U5<br>(anti-PSMA arm) | SEQ ID NO: 19<br>EVQLVQSGAEVKKPGESLKISCK<br>ASGYSFTTYWIGWVRQMPGKGLE<br>LMGIIYPYDSDTRYSPSFQGQVTIS<br>ADKSINTAYLQWSSLKASDTAMY<br>YCARITGGYLFDYWGQGILVTVSS<br>ASTKGPSVFPLAPCSRSTSESTAALG<br>CLVKDYFPEPVTVSWNSGALTSGV<br>HTFPAVLQSSGLYSLSSVVTVPSSSL<br>GTKTYTCNVDHKPSNTKVDKRVES<br>KYGPPCPPCPAPEAAGGPSVFLFPPK<br>PKDTLMISRTPEVTCVVVDVSQEDP<br>EVQFNWYVDGVEVHNAKTKPREE<br>QFNSTYRVVSVLTVLHQDWLNGKE<br>YKCKVSNKGLPSSIEKTISKAKGQP<br>REPQVCTLPPSQEEMTKNQVSLSCA<br>VKGFYPSDIAVEWESNGQPENNYK<br>TTPPVLDSDGSFFLVSRLTVDKSRW<br>QEGNVFSCSVMHEALHNHYTQKSL<br>SLSLG | SEQ ID NO: 20<br>QSALTQPPSASGSPGQSVTISCTG<br>TSSDVGGYNYVSWYQQHPGKAP<br>KLMIYEVTKRPSGVPDRFSGSKS<br>GNTASLTVSGLQAEDEADYYCT<br>SYAGSNKYVFGTGTKVTVLGQP<br>KAAPSVTLFPPSSEELQANKATLV<br>CLISDFYPGAVTVAWKADSSPVK<br>AGVETTTPSKQSNNKYAASSYLSL<br>TPEQWKSHKSYSCQVTHEGSTVE<br>KTVAPTECS |

Note:
The modified TCR beta constant region and modified TCR alpha constant region in the anti-CD3 arm are highlighted in italics.

Nucleotide Sequences of W308051 Variable Regions

| moiety | VH | VL |
|---|---|---|
| T3<br>(anti-CD3 arm) | SEQ ID NO: 21<br>CAGGTGCAGCTTGTGCAGTCTGGG<br>GCAGAAGTGAAGAAGCCTGGGTC<br>TAGTGTCAAGGTGTCATGCAAGGC<br>TAGCGGGTTCGCCTTTACTGACTA<br>CTACATCCACTGGGTGCGGCAGGC<br>TCCCGGACAAGGGTTGGAGTGGA<br>TGGGATGGATCTCCCCAGGCAATG<br>TCAACACAAAGTACAACGAGAAC<br>TTCAAAGGCCGCGTCACCATTACC<br>GCCGACAAGAGCACCTCCACAGC<br>CTACATGGAGCTGTCCAGCCTCAG<br>AAGCGAGGACACTGCCGTCTACTA<br>CTGTGCCAGGGATGGGTACTCCCT<br>GTATTACTTTGATTACTGGGGCCA<br>GGGCACACTGGTGACAGTGCTGG<br>AG | SEQ ID NO: 22<br>GATATCGTGATGACCCAGAGCC<br>CAGACTCCCTTGCTGTCTCCCTC<br>GGCGAAAGAGCAACCATCAACT<br>GCAAGAGCTCCCAAAGCCTGCT<br>GAACTCCAGGACCAGGAAGAAT<br>TACCTGGCCTGGTATCAGCAGAA<br>GCCCGGCCAGCCTCCTAAGCTGC<br>TCATCTACTGGGCCTCCACCCGG<br>CAGTCTGGGGTGCCCGATCGGTT<br>TAGTGGATCTGGGAGCGGGACA<br>GACTTCACATTGACAATTAGCTC<br>ACTGCAGGCCGAGGACGTGGCC<br>GTCTACTACTGTACTCAGAGCCA<br>CACTCTCCGCACATTCGGCGGAG<br>GGACTAAAGTGGAGATTAAG |
| U5<br>(anti-PSMA arm) | SEQ ID NO: 23<br>GAGGTGCAGCTGGTGCAGTCTGG<br>AGCAGAGGTGAAAAAGCCCGGGG<br>AGTCTCTGAAGATCTCCTGTAAGG<br>CTTCTGGATACAGCTTTACCACCT | SEQ ID NO: 24<br>CAGTCTGCCCTGACTCAGCCTCC<br>CTCCGCGTCCGGGTCTCCTGGAC<br>AGTCAGTCACCATCTCCTGCACT<br>GGAACCAGCAGTGACGTTGGTG |

-continued

| moiety | VH | VL |
|---|---|---|
| | ACTGGATCGGCTGGGTGCGCCAG | GTTATAACTATGTCTCCTGGTAC |
| | ATGCCCGGGAAAGGCCTGGAGTT | CAACAGCACCCAGGCAAAGCCC |
| | AATGGGGATCATCTATCCTTATGA | CCAAACTCATGATTTATGAGGTC |
| | CTCTGATACCAGATACAGCCCGTC | ACTAAGCGGCCCTCAGGGGTCC |
| | CTTCCAAGGCCAGGTCACCATCTC | CTGATCGCTTCTCTGGCTCCAAG |
| | AGCCGACAAGTCCATCAACACCG | TCTGGCAACACGGCCTCCCTGAC |
| | CCTACCTGCAGTGGAGCAGCCTGA | CGTCTCTGGGCTCCAGGCTGAGG |
| | AGGCCTCGGACACCGCCATGTATT | ATGAGGCTGATTATTACTGCACC |
| | ACTGTGCGAGAATTACGGGTGGCT | TCATATGCAGGCAGCAACAAAT |
| | ACCTCTTTGACTACTGGGGCCAGG | ATGTCTTCGGAACTGGGACCAA |
| | GAATCCTGGTCACCGTCTCCTCA | GGTCACCGTCCTA |

Nucleotide Sequences of W308051 Heavy Chain and Light Chain

| moiety | Sequence |
|---|---|
| T3<br>(anti-CD3 arm) | Heavy chain (SEQ ID NO: 25)<br>CAGGTGCAGCTTGTGCAGTCTGGGGCAGAAGTGAAGAAGCCTGGGTC<br>TAGTGTCAAGGTGTCATGCAAGGCTAGCGGGTTCGCCTTTACTGACT<br>ACTACATCCACTGGGTGCGGCAGGCTCCCGGACAAGGGTTGGAGTGG<br>ATGGGATGGATCTCCCCAGGCAATGTCAACACAAAGTACAACGAGA<br>ACTTCAAAGGCCGCGTCACCATTACCGCCGACAAGAGCACCTCCACA<br>GCCTACATGGAGCTGTCCAGCCTCAGAAGCGAGGACACTGCCGTCTA<br>CTACTGTGCCAGGGATGGGTACTCCCTGTATTACTTTGATTACTGGGG<br>CCAGGGCACACTGGTGACAGTGCTGGAGgacctgaagaacgtgttccctcccgaggtg<br>gccgtgttcgaacccagcgagtgcgagatcagccacacccagaaggccaccctggtgtgtctggccaccggcttc<br>taccccgaccacgtggagctgagctggtgggtgaacggcaaggaggtgcacagcggcgtgtgtaccgaccctca<br>gcccctgaaggagcagcccgccctgcaggacagcaggtacgccctgagcagcaggctgagagtgagcgccac<br>cttctggcagaaccccaggaaccacttcaggtgccaggtgcagttctacggcctgagcgagaacgacgagtgga<br>cccaggacagggccaagcccgtgacccagatcgtgagcgctgaggcctggggcagatatggtcccccatgccc<br>accatgcccagcacctgaggccgctggggggaccatcagtcttcctgttcccccccaaaacccaaggacactctcatg<br>atctcccggacccctgaggtcacgtgcgtggtggtggacgtgagccaggaagaccccgaggtccagttcaactg<br>gtacgtggatggcgtggaggtgcataatgccaagacaaagccgcgggaggagcagttcaacagcacgtaccgtg<br>tggtcagcgtcctcaccgtcctgcaccaggactggctgaacggcaaggagtacaagtgcaaggtctccaacaaag<br>gcctcccgtcctccategagaaaaccatctccaaagccaaagggcagccccgagagccacaggtgtacaccctg<br>cccccatgccaggaggagatgaccaagaaccaggtcagcctgtggtgcctggtcaaaggcttctaccccagcga<br>catcgccgtggagtgggagagcaatgggcagccggagaacaactacaagaccacgcctcccgtgctggactcc<br>gacggctccttcttcctctacagcaggctaaccgtggacaagagcaggtggcaggaggggaatgtcttctcatgct<br>ccgtgatgcatgaggctctgcacaaccactacacacagaagagcctctccctgtctctgggt<br>Light chain (SEQ ID NO: 26)<br>GATATCGTGATGACCCAGAGCCCAGACTCCCTTGCTGTCTCCCTCGGC<br>GAAAGAGCAACCATCAACTGCAAGAGCTCCCAAAGCCTGCTGAACTC<br>CAGGACCAGGAAGAATTACCTGGCCTGGTATCAGCAGAAGCCCGGCC<br>AGCCTCCTAAGCTGCTCATCTACTGGGCCTCCACCCGGCAGTCTGGG<br>GTGCCCGATCGGTTTAGTGGATCTGGGAGCGGGACAGACTTCACATT<br>GACAATTAGCTCACTGCAGGCCGAGGACGTGGCCGTCTACTACTGTA<br>CTCAGAGCCACACTCTCCGCACATTCGGCGGAGGGACTAAAGTGGAG<br>ATTAAGcccgacatccagaaccccgaccccgccgtgtaccagctgagagacagcaagagcagcgacaag<br>agcgtgtgcctgttcaccgacttcgacagccagacccaggtgagccagagcaaggactccgacgtgtatatcacc<br>gacaagtgcgtgctggacatgaggagcatggacttcaagagcaacagcgccgtggcctggagccagaagagcg<br>acttcgcctgcgccaacgccttccagaacagcatcatccccgaggacaccttcttctgcagc |
| U5<br>(anti-PSMA arm) | Heavy chain (SEQ ID NO: 27)<br>GAGGTGCAGCTGGTGCAGTCTGGAGCAGAGGTGAAAAAGCCCGGGG<br>AGTCTCTGAAGATCTCCTGTAAGGCTTCTGGATACAGCTTTACCACCT<br>ACTGGATCGGCTGGGTGCGCCAGATGCCCGGGAAAGGCCTGGAGTTA<br>ATGGGGATCATCTATCCTTATGACTCTGATACCAGATACAGCCCGTCC<br>TTCCAAGGCCAGGTCACCATCTCAGCCGACAAGTCCATCAACACCGC<br>CTACCTGCAGTGGAGCAGCCTGAAGGCCTCGGACACCGCCATGTATT<br>ACTGTGCGAGAATTACGGGTGGCTACCTCTTTGACTACTGGGGCCAG<br>GGAATCCTGGTCACCGTCTCCTCAgegtcgaccaagggcccatccgtcttccccctggcgc<br>cctgctccaggagcacctccgagagcacagccgccctgggctgcctggtcaaggactacttccccgaaccggtg<br>acggtgtcgtggaactcaggcgccctgaccagcggcgtgcacaccttcccggctgtcctacagtcctcaggactct<br>actccctcagcagcgtggtgaccgtgccctccagcagcttgggcacgaagacctacacctgcaacgtagatcaca<br>agcccagcaacaccaaggtggacaagagagttgagtccaaatatggtcccccatgcccaccatgcccagcacct<br>gaggcagcaggggggaccatcagtcttcctgttccccccaaaacccaaggacactctcatgatctcccggacccctg<br>aggtcacgtgcgtggtggtggacgtgagccaggaagaccccgaggtccagttcaactggtacgtggatggcgtg<br>gaggtgcataatgccaagacaaagccgcgggaggagcagttcaacagcacgtaccgtgtggtcagegtcctcac<br>cgtcctgcaccaggactggctgaacggcaaggagtacaagtgcaaggtctccaacaaaggcctcccgtcctccat<br>cgagaaaaccatctccaaagccaaagggcagccccgagagccacaggtgtgcaccctgcccccatcccaggag<br>gagatgaccaagaaccaggtcagcctgagctgcgcggtcaaaggcttctaccccagcgacatcgccgtggagtg<br>ggagagcaatgggcagccggagaacaactacaagaccacgcctcccgtgctggactccgacggctccttcttcct<br>cgttagcaggctaaccgtggacaagagcaggtggcaggaggggaatgtcttctcatgctccgtgatgcatgaggc |

-continued

| moiety | Sequence |
|---|---|
| | tctgcacaaccactacacacagaagagcctctccctgtctctgggt |
| | Light chain (SEQ ID NO: 28) |
| | CAGTCTGCCCTGACTCAGCCTCCCTCCGCGTCCGGGTCTCCTGGACAG |
| | TCAGTCACCATCTCCTGCACTGGAACCAGCAGTGACGTTGGTGGTTAT |
| | AACTATGTCTCCTGGTACCAACAGCACCCAGGCAAAGCCCCCAAACT |
| | CATGATTTATGAGGTCACTAAGCGGCCCTCAGGGGTCCCTGATCGCTT |
| | CTCTGGCTCCAAGTCTGGCAACACGGCCTCCCTGACCGTCTCTGGGCT |
| | CCAGGCTGAGGATGAGGCTGATTATTACTGCACCTCATATGCAGGCA |
| | GCAACAAATATGTCTTCGGAACTGGGACCAAGGTCACCGTCCTAggtca |
| | gcccaaggctgccccctcggtcactctgttcccgccctcctctgaggagcttcaagccaacaaggccacactggtg |
| | tgtctcataagtgacttctacccgggagccgtgacagtggcctggaaggcagatagcagccccgtcaaggcggga |
| | gtggagaccaccacaccctccaaacaaagcaacaacaagtacgoggccagcagctacctgagcctgacgcctg |
| | agcagtggaagtcccacaaaagctacagttgccaggtcacgcatgaagggagcaccgtggagaagacagtggc |
| | ccctacagaatgttca |

Note:
The nucleotide sequences of variable regions are shown in capital.

Codon Optimized Nucleotide Sequences of W308051 Heavy Chain and Light Chain

| moiety | Sequence |
|---|---|
| T3 | Heavy chain (SEQ ID NO: 35) |
| (anti-CD3 arm) | caggtgcagttggtgcaatcaggggctgaagtcaaaaagccagggtcttccgttaaggttagc |
| | tgcaaagcatccggatttgcctttaccgattactacattcactgggtcaggcaagcgcca |
| | ggtcagggcctggaatggatgggctggattagtcccggaaacgtgaacactaagtataat |
| | gagaattttaaaggacgagtgactatcaccgccgacaagtccacatccaccgcctatatg |
| | gagctgtcttcattgcgctcggaggacacagctgtttactactgtgcccgagatggctat |
| | agcctgtattactttgactactggggccagggtacccttgtcaccgtgctcgaggacctc |
| | aaaaatgtgtttccacctgaggtggccgtgtttgagccaagcgaatgtgaaatctctcac |
| | acccaaaaagctacacttgtttgcttagcgaccggcttttatcctgatcatgtggagctc |
| | tcatggtgggtcaacgggaaggaggtccattccggagtttgcaccgacccgcaacccctc |
| | aaggagcagcctgccctccaagatagcagatacgcactttcatcacggctgcgggtgtct |
| | gctactttttggcaaaatcctcggaatcacttccgttgccaagtacagttctacgggctg |
| | tctgagaacgatgagtggacccaggacagggccaagcccgtgactcagattgtgtcggcc |
| | gaagcatggggtaggtatggtcccccatgcccaccatgcccagcacctgaggccgccggg |
| | ggaccatcagtcttcctgttcccccaaaacccaaggacactctcatgatctcccggacc |
| | cctgaggtcacgtgcgtggtggtggacgtgagccaggaagaccccgaggtccagttcaac |
| | tggtacgtggatggcgtggaggtgcataatgccaagacaaagccgcgggaggagcagttc |
| | aacagcacgtaccgtgtggtcagcgtcctcaccgtcctgcaccaggactggctgaacggc |
| | aaggagtacaagtgcaaggtctccaacaaaggcctcccgtcctccatcgagaaaaccatc |
| | tccaaagccaaagggcagccccgagagccacaggtgtacaccctgcccccatgccaggag |
| | gagatgaccaagaaccaggtcagcctgtggtgcctggtcaaaggcttctaccccagcgac |
| | atcgccgtggagtgggagagcaatgggcagccggagaacaactacaagaccacgcctccc |
| | gtgctggactccgacggctccttcttcctctacagcaggctaaccgtggacaagagcagg |
| | tggcaggaggggaatgtcttctcatgctccgtgatgcatgaggctctgcacaaccactac |
| | acacagaagagcctctccctgtctctgggc |
| | Light chain (SEQ ID NO: 36) |
| | gacattgtgatgacacagagtcctgattctctggctgttagcctgggggaacgagccaca |
| | atcaactgcaaatcgtcacaatcactcctcaatagcagaacgcgcaagaattatttggcc |
| | tggtatcaacaaaagccgggccagcccccaaagctcctgatctactgggcttccacgcgg |
| | cagtcgggcgtgccggataggttcagtggcagtggctctggaaccgatttcaccctgaca |
| | attagcagcctgcaagccgaggacgtggctgtgtactactgcacacaaagccacacactg |
| | cggaccttcggtggtggaaccaaggtcgagatcaaacccgatattcaaaaccccgaccct |
| | gctgtatatcaactacgggacagcaagtctagtgataagtctgtctgcctgttcactgac |
| | ttcgatagtcagacccaggtatctcaaagcaaggactctgatgtgtacataactgataaa |
| | tgcgtgctggacatgcggagcatggattttaaaagtaacagtgccgtggcctggtcgcaa |
| | aagtcagacttcgcttgtgccaatgcctttcaaaattccatcattcctgaggataccttc |
| | ttctgctct |
| U5 | Heavy chain (SEQ ID NO: 37) |
| (anti-PSMA arm) | gaggtgcagctggtgcaaagtggagctgaagtgaagaagccaggcgagtccctcaagatttcc |
| | tgcaaggctagcggatattcgttcacaacttattggatcggatgggttaggcagatgcct |
| | ggcaagggtcttgagctgatgggcattatttatccttatgactcggacactaggtactcc |
| | ccaagcttccaaggccaggttactattagtgccgacaagagcattaacactgcctatttg |
| | caatggagttctcttaaagccagtgataccgcaatgtattactgtgctcgaatcaccgga |
| | ggctacctgtttgattactggggccaaggcattctggtgaccgtttcaagcgcaagcacc |
| | aaagggccaagcgtgttcccacttgcaccttgttcccggagcacctccgagagcacggcc |
| | gcgctgggctgcttagtgaaagactactttcctgagccggtgacagttagctggaattct |
| | ggcgccctgacatcaggagtccacacgttcccggctgtactccaaagctcaggcttgtat |
| | tctttgtcttctgtggtgaccgtgcctagtagctctctcggaaccaaaacctatacttgt |
| | aatgtagaccataagccaagcaatactaaagtggataaacgcgtcgagtccaaatacgga |
| | ccaccatgtccccccttgtcctgctcctgaggccgccggtggacctagcgtatttctcttt |
| | cctcctaagcctaaggatactctgatgatatcgcggaccccagaagtgacctgcgtggtg |

-continued

| moiety | Sequence |
|---|---|
| | gtagatgtcagtcaggaagatcccgaagtgcaattcaattggtacgtggatggagttgag<br>gtgcacaacgccaagactaaaccccgtgaagagcaattcaactctacttaccgggtggtg<br>tccgtgcttaccgtgctacatcaagattggctgaatggaaaggagtacaaatgtaaagtg<br>tcaaataaggggctgccctctagcatagagaagacaatctccaaggctaaggggcagcca<br>agggagccccaagtctgcactcttcctcctagccaagaagagatgaccaagaaccaggtg<br>tctctgagctgtgctgtgaagggcttctatcctagcgatattgcggtcgaatgggaatcc<br>aacgggcagccagagaacaactacaagaccacacccccctgtgctcgattccgacggaagc<br>tttttcttggtttcgaggctgactgtggacaaatcaaggtggcaggaggggaacgtattt<br>tcgtgctctgtgatgcatgaagctctgcacaaccactatactcaaaaatccctgtctctg<br>agcttgggc<br>Light chain (SEQ ID NO: 38)<br>caaagcgccctcacgcaacccccctagcgcgtctggctcccctggacaaagcgtaacgatatct<br>tgtactggtacctcttctgacgttggcggctataactatgtgtcttggtatcaacaacac<br>ccaggcaaagctcccaagctgatgatttacgaagtcaccaagcggcccagcggagtgcct<br>gaccggttctctggatccaaatctgggaacacagcatccctcaccgtttctggactacag<br>gcagaggatgaggccgactattactgcacatcttacgctggtagcaataaatacgttttt<br>gggacaggcaccaaagtgactgtgcttggtcagcccaaggctgcccccctcggtcactctg<br>ttcccgccctcctctgaggagcttcaagccaacaaggccacactggtgtgtctcataagt<br>gacttctacccgggagccgtgacagtggcctggaaggcagatagcagccccgtcaaggcg<br>ggagtggagaccaccacaccctccaaacaaagcaacaacaagtacgcggccagcagctac<br>ctgagcctgacgcctgagcagtggaagtcccacaagagctacagctgccaggtcacgcat<br>gaagggagcaccgtggagaagacagtggcccctacagaatgttca |

The other illustrative antibody is a fully human anti-PSMA monoclonal antibody designated as W305042-1.135.2-uIgGIL, or WBP305042. The CDR numbering is defined using IMGT+Kabat, covering all the residues defined by both IMGT and Kabat.

WBP305042 CDR Amino Acid Sequences

| | CDR1 | CDR2 | CDR3 |
|---|---|---|---|
| Heavy chain CDR | SEQ ID NO: 1<br>GYSFTTYWIG | SEQ ID NO: 2<br>IIYPYDSDTRYSPSFQG | SEQ ID NO: 3<br>ITGGYLFDY |
| Light chain CDR | SEQ ID NO: 4<br>TGTSSDVGGYNYVS | SEQ ID NO: 5<br>EVTKRPS | SEQ ID NO: 6<br>TSYAGSNKYV |

WBP305042 Variable Region Amino Acid Sequences

| VH (heavy chain variable region) | VL (light chain variable region) |
|---|---|
| SEQ ID NO: 15<br>EVQLVQSGAEVKKPGESLKISCKASG<br>YSFTTYWIGWVRQMPGKGLELMGII<br>YPYDSDTRYSPSFQGQVTISADKSINT<br>AYLQWSSLKASDTAMYYCARITGGY<br>LFDYWGQGILVTVSS | SEQ ID NO: 16<br>QSALTQPPSASGSPGQSVTISCTGTS<br>SDVGGYNYVSWYQQHPGKAPKLM<br>IYEVTKRPSGVPDRFSGSKSGNTAS<br>LTVSGLQAEDEADYYCTSYAGSNK<br>YVFGTGTKVTVL |

WBP305042 Variable Region Nucleotide Sequences

| VHnu (heavy chain variable region nucleotide sequence) | VLnu (light chain variable region nucleotide sequence) |
|---|---|
| SEQ ID NO: 23<br>gaggtgcagctggtgcagtctggagcagaggtgaaaaa<br>gcccggggagtctctgaagatctcctgtaaggcttctggat<br>acagctttaccacctactggatcggctgggtgcgccagat<br>gcccgggaaaggcctggagttaatggggatcatctatcct<br>tatgactctgataccagatacagcccgtccttccaaggcca<br>ggtcaccatctcagccgacaagtccatcaacaccgcctac<br>ctgcagtggagcagcctgaaggcctoggacaccgccat<br>gtattactgtgcgagaattacgggtggctacctctttgacta<br>ctggggccagggaatcctggtcaccgtctcctca | SEQ ID NO: 24<br>cagtctgccctgactcagcctccctccgcgtccgggtct<br>cctggacagtcagtcaccatctcctgcactggaaccag<br>cagtgacgttggtggttataactatgtctcctggtaccaa<br>cagcacccaggcaaagcccccaaactcatgatttatga<br>ggtcactaagcggccctcaggggtccctgatcgcttct<br>ctggctccaagtctggcaacacggcctccctgaccgtc<br>tctgggctccaggctgaggatgaggctgattattactgc<br>acctcatatgcaggcagcaacaaatatgtcttcggaact<br>gggaccaaggtcaccgtccta |

WBP305042 Heavy Chain and Light Chain

| Heavy chain (amino acid sequence) | Light chain (amino acid sequence) |
|---|---|
| SEQ ID NO: 31<br>EVQLVQSGAEVKKPGESLKISCKASG<br>YSFTTYWIGWVRQMPGKGLELMGII<br>YPYDSDTRYSPSFQGQVTISADKSINT<br>AYLQWSSLKASDTAMYYCARITGGY<br>LFDYWGQGILVTVSSASTKGPSVFPL<br>APSSKSTSGGTAALGCLVKDYFPEPV<br>TVSWNSGALTSGVHTFPAVLQSSGL<br>YSLSSVVTVPSSSLGTQTYICNVNHK<br>PSNTKVDKRVEPKSCDKTHTCPPCPA<br>PELLGGPSVFLFPPKPKDTLMISRTPE<br>VTCVVVDVSHEDPEVKFNWYVDGV<br>EVHNAKTKPREEQYNSTYRVVSVLT<br>VLHQDWLNGKEYKCKVSNKALPAPI<br>EKTISKAKGQPREPQVYTLPPSREEM<br>TKNQVSLTCLVKGFYPSDIAVEWESN<br>GQPENNYKTTPPVLDSDGSFFLYSKL<br>TVDKSRWQQGNVFSCSVMHEALHN<br>HYTQKSLSLSPG | SEQ ID NO: 32<br>QSALTQPPSASGSPGQSVTISCTGTS<br>SDVGGYNYVSWYQQHPGKAPKLM<br>IYEVTKRPSGVPDRFSGSKSGNTAS<br>LTVSGLQAEDEADYYCTSYAGSNK<br>YVFGTGTKVTVLGQPKAAPSVTLFP<br>PSSEELQANKATLVCLISDFYPGAV<br>TVAWKADSSPVKAGVETTTPSKQS<br>NNKYAASSYLSLTPEQWKSHRSYS<br>CQVTHEGSTVEKTVAPTECS |

| Heavy chain (nucleotide sequence) | Light chain (nucleotide sequence) |
|---|---|
| SEQ ID NO: 33<br>gaggtgcagctggtgcagtctggagcagaggtgaaaaa<br>gcccggggagtctctgaagatctcctgtaaggcttctggat<br>acagctttaccacctactggatcggctgggtgcgccagat<br>gcccgggaaaggcctggagttaatggggatcatctatcct<br>tatgactctgataccagatacagcccgtccttccaaggcca<br>ggtcaccatctcagccgacaagtccatcaacaccgcctac<br>ctgcagtggagcagcctgaaggcctcggacaccgccat<br>gtattactgtgcgagaattacgggtggctacctctttgacta<br>ctggggccagggaatcctggtcaccgtctcctcagcgtc<br>gaccaagggcccatccgtcttccccctggcaccctcctcc<br>aagagcacctctgggggcacagcggccctgggctgcct<br>ggtcaaggactacttccccgaaccggtgacggtgtcctg<br>gaactcaggcgctctgaccagcggcgtgcacaccttccc<br>ggctgtcctacagtcctcaggactctactccctcagcagc<br>gtggtgaccgtgccctccagcagcttgggcacccagacc<br>tacatctgcaacgtgaatcacaagcccagcaacaccaag<br>gtggacaagagagttgagcccaaatcttgtgacaaaactc<br>acacatgcccaccgtgcccagcacctgaactcctgggggg<br>gaccgtcagtcttcctcttccccccaaaacccaaggacac<br>cctcatgatctcccggacccctgaggtcacatgcgtggtg<br>gtggacgtgagccacgaagaccctgaggtcaagttcaac<br>tggtacgtggacggcgtggaggtgcataatgccaagaca<br>aagccgcgggaggagcagtacaacagcacgtaccgtgt<br>ggtcagcgtcctcaccgtcctgcaccaggactggctgaat<br>ggcaaggagtacaagtgcaaggtctccaacaaagccctc<br>ccagcccccatcgagaaaaccatctccaaagccaaagg<br>gcagccccgagaaccacaggtctacaccctgcccccatc<br>ccgggaggagatgaccaagaaccaggtcagcctgacct<br>gcctggtcaaaggcttctatcccagcgacatcgccgtgga<br>gtgggagagcaatgggcagccggagaacaactacaaga<br>ccacgcctcccgtgctggactccgacggctccttcttcctc<br>tatagcaagctcaccgtggacaagagcaggtggcagca<br>ggggaacgtcttctcatgctccgtgatgcatgaggctctgc<br>acaaccactacacgcagaagagcttaagcctgtctccgg<br>gttga | SEQ ID NO: 34<br>cagtctgccctgactcagcctccctccgcgtccgggtct<br>cctggacagtcagtcaccatctcctgcactggaaccag<br>cagtgacgttggtggttataactatgtctcctggtaccaa<br>cagcacccaggcaaagcccccaaactcatgatttatga<br>ggtcactaagcggccctcaggggtccctgatcgcttct<br>ctggctccaagtctggcaacacggcctccctgaccgtc<br>tctgggctccaggctgaggatgaggctgattattactgc<br>acctcatatgcaggcagcaacaaatatgtcttcggaact<br>gggaccaaggtcaccgtcctaggtcagcccaaggctg<br>ccccctcggtcactctgttcccgccctcctctgaggagc<br>ttcaagccaacaaggccacactggtgtgtctcataagtg<br>acttctacccgggagccgtgacagtggcctggaaggc<br>agatagcagccccgtcaaggcgggagtggagaccac<br>cacaccctccaaacaaagcaacaacaagtacgcggcc<br>agcagctacctgagcctgacgcctgagcagtggaagt<br>cccacagaagctacagctgccaggtcacgcatgaagg<br>gagcaccgtggagaagacagtggcccctacagaatgt<br>tcatag |

ILLUSTRATIVE EMBODIMENTS

Embodiment 1: An isolated antibody or the antigen-binding portion thereof, comprising a prostate-specific membrane antigen (PSMA) binding moiety capable of binding to PSMA, wherein the PSMA binding moiety comprises: a heavy chain CDR1 comprising the sequence of SEQ ID NO: 1; a heavy chain CDR2 comprising the sequence of SEQ ID NO: 2; a heavy chain CDR3 comprising the sequence of SEQ ID NO: 3; a light chain CDR1 comprising the sequence of SEQ ID NO: 4; a light chain CDR2 comprising the sequence of SEQ ID NO: 5; and a light chain CDR3 comprising the sequence of SEQ ID NO: 6.

Embodiment 2: The isolated antibody or the antigen-binding portion thereof of Embodiment 1, wherein the PSMA binding moiety comprises a heavy chain variable region comprising the amino acid sequence of SEQ ID NO: 15 or an amino acid sequence encoded by SEQ ID NO: 23 and a light chain variable region comprising the amino acid sequence of SEQ ID NO: 16 or an amino acid sequence encoded by SEQ ID NO: 24.

Embodiment 3: The isolated antibody or the antigen-binding portion thereof of Embodiments 1 or 2, which is a bispecific antibody or an antigen-binding portion thereof and comprises a CD3 binding moiety that is capable of binding to CD3.

Embodiment 4: The isolated antibody or the antigen-binding portion thereof of Embodiment 3, wherein the CD3 binding moiety comprises: a heavy chain CDR1 comprising the sequence of SEQ ID NO: 7, a heavy chain CDR2 comprising the sequence of SEQ ID NO: 8, a heavy chain CDR3 comprising the sequence of SEQ ID NO: 9, a light chain CDR1 comprising the sequence of SEQ ID NO: 10, a light chain CDR2 comprising the sequence of SEQ ID NO: 11, and a light chain CDR3 c comprising the sequence of SEQ ID NO: 12.

Embodiment 5: The isolated antibody or the antigen-binding portion thereof of Embodiment 3 or 4, wherein the CD3 binding moiety comprises a heavy chain variable region comprising the sequence of SEQ ID NO: 13 or an amino acid sequence encoded by SEQ ID NO: 21, and a light chain variable region comprising the sequence of SEQ ID NO: 14 or an amino acid sequence encoded by SEQ ID NO: 22.

Embodiment 6: The isolated antibody or the antigen-binding portion thereof of Embodiment 5, wherein the CD3 binding moiety comprises a heavy chain TCR beta constant region comprising the sequence of SEQ ID NO: 29, and a light chain TCR beta constant region comprising the sequence of SEQ ID NO: 30.

Embodiment 7: The isolated antibody or the antigen-binding portion thereof of Embodiment 6, wherein the CD3 binding moiety comprises a heavy chain comprising the sequence of SEQ ID NO: 17, and a light chain comprising the sequence of SEQ ID NO: 18.

Embodiment 8: The isolated antibody or the antigen-binding portion thereof of any one of Embodiments 1-7, wherein the PSMA binding moiety comprises a heavy chain comprising the sequence of SEQ ID NO: 19, and a light chain comprising the sequence of SEQ ID NO: 20.

Embodiment 9: The isolated antibody or the antigen-binding portion thereof of Embodiments 1 or 2, wherein the PSMA binding moiety comprises a heavy chain comprising the sequence of SEQ ID NO: 31 or an amino acid sequence encoded by SEQ ID NO: 33, and a light chain comprising the sequence of SEQ ID NO: 32 or an amino acid sequence encoded by SEQ ID NO: 34.

Embodiment 10: The isolated antibody or the antigen-binding portion thereof of any one of Embodiments 1-9, which is a monoclonal antibody, a chimeric antibody, or a humanized antibody.

Embodiment 11: The isolated antibody or the antigen-binding portion thereof of Embodiment 10, which is a monoclonal antibody.

Embodiment 12: The isolated antibody or the antigen-binding portion thereof of Embodiment 11, which is a human monoclonal antibody.

Embodiment 13: The isolated antibody or the antigen-binding portion thereof of any one of Embodiments 1-12, which is fused to a constant region of an IgG, optionally a human IgG, optionally, a human IgG1 or human IgG4.

Embodiment 14: A pharmaceutical composition comprising the isolated antibody or the antigen-binding portion thereof of any one of Embodiments 1-13 and a pharmaceutically acceptable carrier.

Embodiment 15: A conjugate comprising the isolated antibody or the antigen-binding portion thereof of any one of Embodiments 1-13 and one or more moieties conjugated to the isolated antibody or the antigen-binding portion thereof.

Embodiment 16: An isolated nucleic acid molecule, comprising a nucleic acid sequence encoding the isolated antibody or the antigen-binding portion thereof of any one of Embodiments 1-13, optionally wherein the nucleic acid sequence comprises any combination of the sequences of SEQ ID NOs: 35 to 38.

Embodiment 17: A vector comprising the nucleic acid molecule of Embodiment 16.

Embodiment 18: A host cell comprising the isolated nucleic acid molecule of Embodiment 16 or the vector of Embodiment 17.

Embodiment 19: A method for preparing the antibody or antigen-binding portion thereof of any one of Embodiments 1-14 comprising: a) expressing the antibody or antigen-binding portion thereof in the host cell of Embodiment 18; and b) isolating the antibody or antigen-binding portion thereof from the host cell.

Embodiment 20: A method for inhibiting growth or metastasis of tumor cells in a subject (e.g., a human subject), comprising administering to the subject an effective amount of the isolated antibody or antigen-binding portion thereof of any one of Embodiments 1-13 or the pharmaceutical composition of Embodiment 14.

Embodiment 21: A method for modulating an immune response in a subject (e.g., a human subject), comprising administering to the subject an effective amount of the isolated antibody or antigen-binding portion thereof of any one of Embodiments 1-13 or the pharmaceutical composition of Embodiment 14.

Embodiment 22: A method for treating or preventing a proliferative disorder, autoimmune disease, inflammatory disease, or infectious disease in a subject (e.g., a human subject), comprising administering to the subject an effective amount of the isolated antibody or antigen-binding portion thereof of any one of Embodiments 1-13 or the pharmaceutical composition of Embodiment 14.

Embodiment 23: The method of Embodiment 22, wherein the method treats a proliferative disorder that is a cancer, optionally prostate cancer, lung cancer, bronchogenic carcinoma, squamous cell carcinoma, small cell carcinoma, large cell carcinoma, adenocarcinoma, alveolar cell carcinoma, bronchial adenoma, chondromatous hamartoma (noncancerous), sarcoma, kidney cancer, breast cancer, gastric cancer, colorectal cancer, glioblastoma, pancreatic cancer, ovarian cancer, or metastatic castration-resistant prostate cancer (mCRPC).

Embodiment 24: The method of Embodiment 23, wherein the cancer is a prostate cancer.

Embodiment 25: The method of any one of Embodiments 20-24, wherein the isolated antibody or antigen-binding portion thereof of any one of Embodiments 1-13 or the pharmaceutical composition of Embodiment 14 is administered in combination with a chemotherapeutic agent, radiation and/or another cancer immunotherapy.

Embodiment 26: A kit for treating or diagnosing a proliferative disorder, an immune disorder, or an infection, comprising a container comprising at least one of the isolated antibody or antigen-binding portion thereof of any one of Embodiments 1-13.

EXAMPLES

The present invention, thus generally described, will be understood more readily by reference to the following Examples, which are provided by way of illustration and are not intended to be limiting of the instant invention. The Examples are not intended to represent that the experiments below are all or the only experiments performed.

The commercial materials used in Examples 1-4 are listed in the table immediately below.

| Materials | Vendor | Cat. No. |
|---|---|---|
| Expi293F ™ Cells | Thermo Fisher | Cat. A14635 |
| ExpiFectamine293 transfection kit | Thermo Fisher | Cat. A14524 |
| Expi293F ™ expression medium | Thermo Fisher | Cat. A1435101 |
| Opti-MEM | Thermo Fisher | Cat. 31985070 |
| Lipofectamine ™ 2000 Transfection Reagent | Thermo Fisher | Cat. 11668019 |
| Protein A column | GE healthcare | Cat. 175438 |
| HPLC-SEC | TOSOH | Cat. 0008541 |
| NuPAGE4%-12% Bis-Tris Gel | Thermo Fisher | Cat. NP0322BOX |
| SYPRO Orange Protein Gel Stain | Invitrogen | S6651 |
| TSKgel butyl-NPR column | Tosoh Bioscience | 0042168 |
| Aurora 1536 SQ Lobase Assay Plates | Aurora | ABI1-00110A |
| HT Protein Express Reagent Kit | PerkinElmer | 760499 |
| THETM His Tag Antibody, mAb, Mouse | GenScript | A00186-100 |
| Human PSMA.ECD.His (Acro) | Acro Biosystems | PSA-H52H3 |
| Mouse PSMA.ECD.His (Acro) | Acro Biosystems | PSA-M5245 |
| Cyno PSMA.ECD.His (Acro) | Acro Biosystems | PSA-C5247 |
| Goat anti-human-Fc-HRP | BETHYL | A80-304P |
| BupH Carbonate-Bicarbonate Buffer | PIERCE | 28382 |
| TMB | LIFE TECHNOLOGIES | 002023 |
| PBS (10X) | Invitrogen | AM9624 |
| TWEEN20 | Sigma | P1379 |
| Bovine Serum Albumin (BSA) | Bovogen | BSAS |
| Goat Anti-human-Fc-Alexa fluor 647 | Jackson ImmunoResearch | 109-605-098 |
| RPMI1640 medium (1X) | Gibco | 22400-089 |
| F-12 medium (1X) | Invitrogen | 21127022 |
| Fetal Bovine Serum (FBS) | ExCell Bio | FND500/L |
| Hygromycin B | Invitrogen | 10687010 |
| DPBS | CORNING | 21-031-CVR |
| 0.25% Trypsin-EDTA (1X) | Gibco | 25200-072 |
| LNCaP FGC | ATCC | CRL-1740 |

Example 1. Preparation of Materials

1.1 Establishment of Stable Cell Lines

Cynomolgus PSMA-expressing cell line WBP3xx042-FlpinCHO.cPro1.B7 (Cyno PSMA+CHO cells) was generated using Flp-in CHO cells (Thermo, R75807) transfected with the plasmid encoding full-length cynomolgus PSMA (XM_005579322.1, NCBI) following the user instructions.

1.2 Production of Benchmark Antibodies

DNA sequences encoding J591 antibody (W3XX042-BMK1) were synthesized in Genewiz (Suzhou, China) according to the sequence 21&22 from WO 02/098897 A2, and then subcloned into modified pcDNA3.3 expression vectors (Thermo).

The plasmids encoding heavy chain and light chain were co-transfected into Expi293 cells. Cells were cultured for 5 days, and supernatant was collected for protein purification using Protein A column (GE Healthcare, 175438). The obtained antibody was analyzed by SDS-PAGE and SEC-HPLC, and then stored at −80° C.

Example 2. Antibody Hybridoma Generation

2.1 Immunization and Cell Fusion

Three OMT rats at the ages of 6-8 weeks, were immunized with human PSMA ECD protein and cynomolgus PSMA ECD protein alternately. Serum antibody titers against the antigen was monitored by ELISA and FACS. For ELISA, 96-well plates (Nunc) were coated with 100 μL of human PSMA antigen at 2 μg/mL at 4° C. overnight, and then blocked with blocking buffer (1×PBS/2% BSA) for 1 hour at ambient temperature. Rat serum was 3-fold serially diluted starting at 1:100 dilutions in blocking buffer and incubated for 1 hour at ambient temperature. The well with no serum sample added was used as negative control. The plates were then washed and subsequently incubated with secondary antibody, goat anti-rat IgG-Fc-HRP (Bethyl), for 1 hour. After washing, TMB substrate was added and the interaction was stopped by 2M HCl. The absorbance at 450 nm was read using a microplate reader (Molecular Device). For FACS, the plates (96 well) were pre-coated with 3×104 of LNCaP cells per well and cultured for 2 days in an incubator set to 37° C., 5% CO2. The plates were blocked with blocking buffer (1×PBS/5% milk) at ambient temperature for 1 hour. Then 50 μL hybridoma supernatant was added into the plates, incubator for 1 hour at ambient temperature. The plates were washed with PBS for 3 times and subsequently incubated with secondary antibody, goat Anti-Rat-Fc-Alexa647 (1:500), at ambient temperature for 1 hour. The mean fluorescence intensity (MFI) of the cells was measured by a flow cytometer and analyzed by FLOWJO.

Lymph nodes and spleen from immunized animal were homogenized and filtered to remove blood clots and cell debris. B cells and Sp2/0 myeloma cells were treated separately with pronase solution, and the reaction was stopped by 100% FBS. The cells were washed and counted. B cells were fused with Sp2/0 myeloma cells at 1:1 ratio in electric fusion solution following general electro-fusion procedures. The fused cells were re-suspended in DMEM medium supplemented with 20% FBS and 1×HAT, and then transferred into 96-well plates. The fused cells were cultured for 10-14 days in an incubator set to 37° C. and 5% $CO_2$.

2.2 High Throughput Screening of Hybridoma Supernatants and IgG Conversion

The process of high-throughput screening with hybridoma culture supernatants includes primary screening by ELISA binding to human PSMA, and confirmation screening by FACS/ELISA binding to human and cynomolgus PSMA.

Total RNAs were isolated from hybridoma cells by using RNeasy Plus Mini Kit (Qiagen). The first strand cDNA was reverse transcripted using oligo dT. VH and VL genes of the antibodies were amplified from cDNA using 3'-constant region degenerated primer and 5'-degenerated primer sets. The 5' degenerated primers were designed based on the upstream signal sequence-coding region of Ig variable sequences. The PCR product was then ligated into pMD18-T vector and 10 μL of the ligation product was transformed into Top 10 competent cells. Transformed cells were plated on 2×YT plates with carbocinin and incubated overnight at 37° C. Total of 12 positive colonies were randomly picked for DNA sequencing.

After sequence analysis and functional screening, candidates were selected for fully human antibody production. The DNA sequences of the variable domain of the candidates were synthesized and cloned into modified pcDNA3.4 vectors containing human IgG1 Fc. After sequence confirming, the expression vectors containing whole IgG of fully human antibodies were used for transient transfection for antibodies production.

Purified IgG antibodies were further screened by ELIAS and FACS binding to human and cynomolgus PSMA. The antibody W305042 was designated as one of the antibodies.

Example 3. Fully Human Antibody Molecules Construction and Purification

Heavy chain and light chain expression plasmids of the antibody W305042 were co-transfected into Expi293 cells using Expi293 expression system kit (ThermoFisher-A14635) according to the manufacturer's instructions. 5 days after transfection, the supernatant was collected and used for protein purification using Protein A column. Antibody concentration was measured by NanoDrop. The purity of proteins was evaluated by SDS-PAGE and SEC-HPLC (FIG. 1). After purification, the yield of W305042 was 223.16 mg/L, and the purity by SEC-HPLC was 99.19%.

Example 4. Antibody Characterization 4.1 Binding Ability Test by ELISA

The binding of W305042 antibody to human PSMA was determined by ELISA. Plate was pre-coated with 1 μg/mL THE™ His Tag Antibody overnight in a refrigerator set to 4° C. After blocking with 200 μL of 1×PBS/2% BSA for 1 hour, the plates were washed with 1×PBST for three times, then 0.5 g/mL human PSMA ECD protein diluted in 1×PBS/2% BSA was added in a volume of 50 μL/well to the plate and incubated for 1 hour at ambient temperature. After washing the plates with 1×PBST for three times, various concentrations (4-fold serially diluted in 1×PBS/2% BSA from 100 nM to 0.095 pM) of W305042 antibody, J591 (positive control) as well as human IgG isotype antibody (negative control) were added in a volume of 50 μL/well to the plate and incubated for 2 hours at ambient temperature. After washing the plates with 1×PBST for three times, 50 μL/well of HRP-labeled goat anti-human IgG antibody (1:5000 diluted in 1×PBS/2% BSA) were added into the plate and incubated for 1 hour at ambient temperature. After washing the plates with 1×PBST for six times, the color was developed by dispensing 50 μL/well of TMB substrate for 4-8 minutes, and then the reaction was stopped by adding 50 μL/well of 2M HCl. The absorbance was read at 450 nm using a microplate reader. The binding EC50 was calculated by GraphPad Prism through plotting antibody concentration (x-axis) versus OD450 value (y-axis) and analyzing as: Nonlinear regression (curve fit)-log (agonist) vs. response-Variable slope (four parameters).

Figure 2:
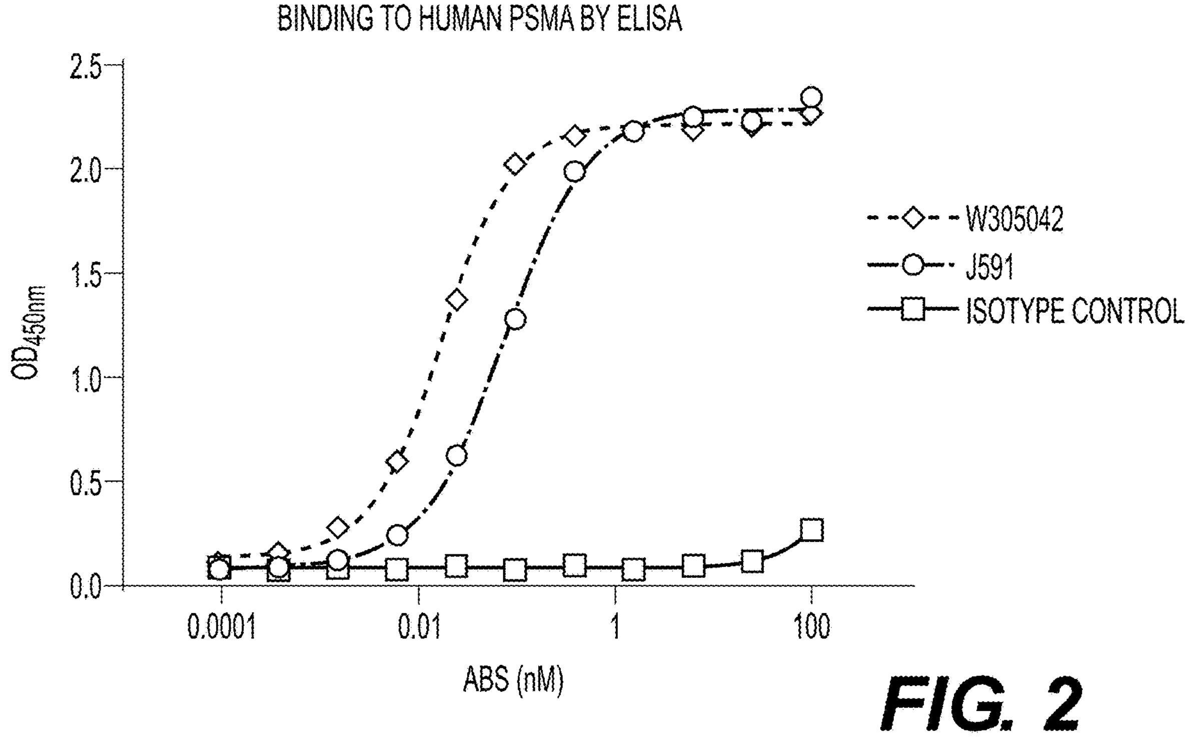
FIG. 2 shows the binding of the antibodies (W305042, J591, and isotope control) to human PSMA by ELISA.

The result of antibodies binding to human PSMA protein is shown in FIG. 2 and Table 1. W305042 could effectively bind to human PSMA ECD protein with an EC50 of 0.017 nM, which was slightly more potent than the reference antibody J591. Human IgG isotype antibody, which was used as the negative control, showed no obvious binding to human PSMA protein. The result suggested good binding ability of W305042 to human PSMA.

TABLE 1

Antibodies binding to human PSMA

| Antibody | $EC_{50}$ (nM) | Max $OD_{450}$ |
|---|---|---|
| W305042 | 0.017 | 2.268 |
| J591 | 0.077 | 2.342 |
| Isotype control | >100 | 0.263 |

4.2 Binding Ability Analysis by Flow Cytometry

Fluorescence activated cell sorting (FACS) was used to detect the binding of W305042 antibody to human PSMA. Briefly, 1×105 cells per well of LNCaP was incubated with various concentrations of W305042 antibody (4-fold serially diluted with 1×PBS/1% BSA from 100 nM to 0.095 pM) in a volume of 100 μL/well for 1 hour in a refrigerator set to 4° C. J591 was used as the positive control and human IgG isotype antibody was used as the negative control. After washing the cells twice with 1×PBS/1% BSA, Alexa fluor 647-labeled goat anti-human antibody (1:500 diluted with 1×PBS/1% BSA) was added into the cells and incubated in a refrigerator set to 4° C. for 0.5 hour in the dark. After washing the cells twice with 1×PBS/1% BSA, the mean fluorescence intensity (MFI) of the cells was measured by a flow cytometer and analyzed by FLOWJO. The binding EC50 was calculated by GraphPad Prism through plotting antibody concentration (x-axis) versus MFI (y-axis) and analyzing as: Nonlinear regression (curve fit)-log (agonist) vs. response-Variable slope (four parameters).

Figure 3:
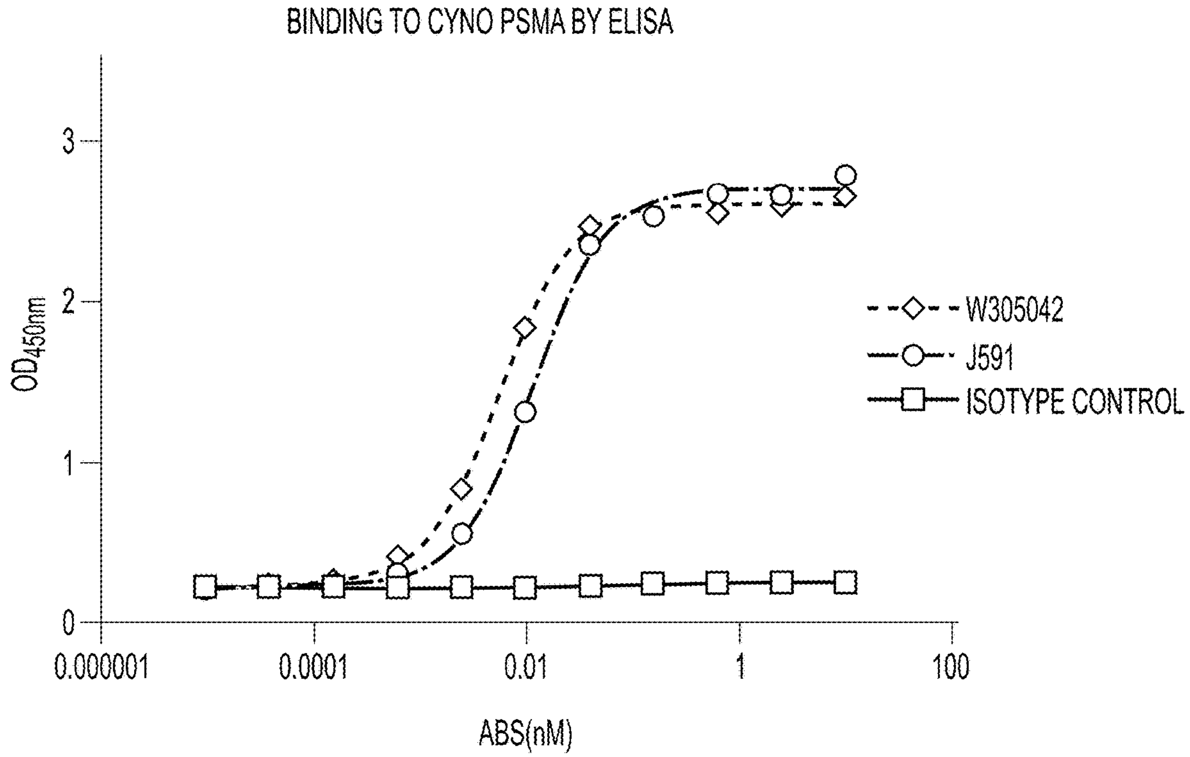
FIG. 3 shows the binding of the antibodies (W305042, J591, and isotope control) to cynomolgus PSMA by ELISA.

The binding result of antibodies to human PSMA-expressing LNCaP cells is shown in FIG. 3 and Table 2. W305042 could effectively bind to LNCaP cells with an EC50 of 0.25 nM, which was comparable to the reference antibody J591. Human IgG isotype antibody, which was used as the negative control, showed no obvious binding to LNCaP cells. The result suggested good binding ability of W305042 to LNCaP cells.

TABLE 2

| Antibodies binding to LNCaP | | |
|---|---|---|
| Antibody | $EC_{50}$ (nM) | Max MFI |
| W305042 | 0.25 | 3987 |
| J591 | 0.48 | 3590 |
| Isotype control | >100 | 47.7 |

4.3 Orthologue (Cross-Species) Binding Test 4.3.1 Binding to Cynomolgus PSMA by ELISA The binding of W305042 antibody to cynomolgus PSMA was determined by ELISA. Plate was pre-coated with 1 μg/mL THETM His Tag Antibody overnight in a refrigerator set to 4° C. After blocking with 200 μL of 1×PBS/2% BSA for 1 hour, the plates were washed with 1×PBST for three times, then 0.5 μg/mL cynomolgus PSMA ECD protein diluted in 1×PBS/2% BSA was added in a volume of 50 μL/well to the plate and incubated for 1 hour at ambient temperature. After washing the plates with 1×PBST for three times, various concentrations (4-fold serially diluted in 1×PBS/2% BSA from 10 nM to 0.0095 pM) of W305042 antibody, J591 (positive control) as well as human IgG isotype antibody (negative control) were added in a volume of 50 μL/well to the plate and incubated for 2 hours at ambient temperature. After washing the plates with 1×PBST for three times, 50 μL/well of HRP-labeled goat anti-human IgG antibody (1:5000 diluted in 1×PBS/2% BSA) were added into the plate and incubated for 1 hour at ambient temperature. After washing the plates with 1×PBST for six times, the color was developed by dispensing 50 μL/well of TMB substrate for 4-8 minutes, and then the reaction was stopped by adding 50 μL/well of 2M HCl. The absorbance was read at 450 nm using a microplate reader. EC50 was determined as described above.

Figure 4:
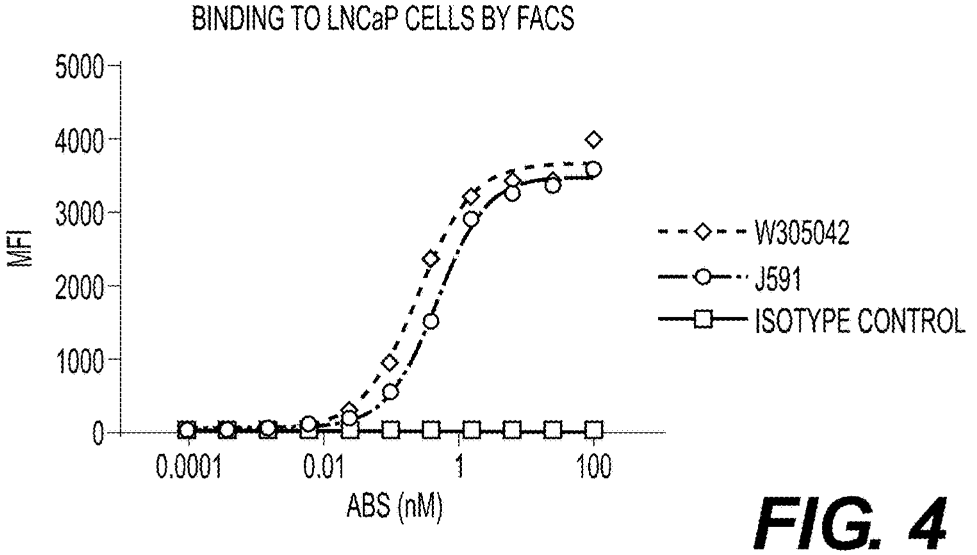
FIG. 4 shows the binding of the antibodies (W305042, J591, and isotope control) to LNCaP cells by FACS.

The result of antibodies binding to cynomolgus PSMA protein is shown in FIG. 4 and Table 3. W305042 could effectively bind to cynomolgus PSMA ECD protein with an EC50 of 0.006 nM, which was comparable to the reference antibody J591. Human IgG isotype antibody, which was used as the negative control, showed no obvious binding to cynomolgus PSMA protein. The result suggested good binding ability of W305042 to cynomolgus PSMA.

TABLE 3

| Antibodies binding to cynomolgus PSMA | | |
|---|---|---|
| Antibody | $EC_{50}$ (nM) | Max $OD_{450}$ |
| W305042 | 0.006 | 2.659 |
| J591 | 0.011 | 2.790 |
| Isotype control | >10 | 0.258 |

4.3.2 Binding to Cynomolgus PSMA by FACS

Fluorescence activated cell sorting (FACS) was used to detect the binding of W305042 antibody to cynomolgus PSMA. This method can quantitatively analyze and identify specific molecules expressed on the surface of living cells. Unlabeled cells were used as a control to set the threshold before detection, and the percentage change of each group that exceeded the fluorescence intensity threshold was analyzed. Cynomolgus PSMA-expressing engineered cell (W3xx042.FIpinCHO.cPro1.B7) was maintained in F-12 medium containing 10% FBS and 600 μg/mL hygromycin. Briefly, 1×105 cells per well of W3xx042.FIpinCHO.cPro1.B7 was incubated with various concentrations of W305042 antibody (4-fold serially diluted with 1×PBS/1% BSA from 100 nM to 6.1 pM) in a volume of 100 μL/well for 1 hour in a refrigerator set to 4° C. J591 was used as the positive control and human IgG isotype antibody was used as the negative control. After washing the cells twice with 1×PBS/1% BSA, Alexa fluor 647-labeled goat anti-human antibody (1:500 diluted with 1×PBS/1% BSA) was added into the cells and incubated in a refrigerator set to 4° C. for 0.5 hour in the dark. After washing the cells twice with 1×PBS/1% BSA, the mean fluorescence intensity (MFI) of the cells was measured by a flow cytometer and analyzed by FLOWJO. MFI and EC50 were determined as described above.

Figure 5:
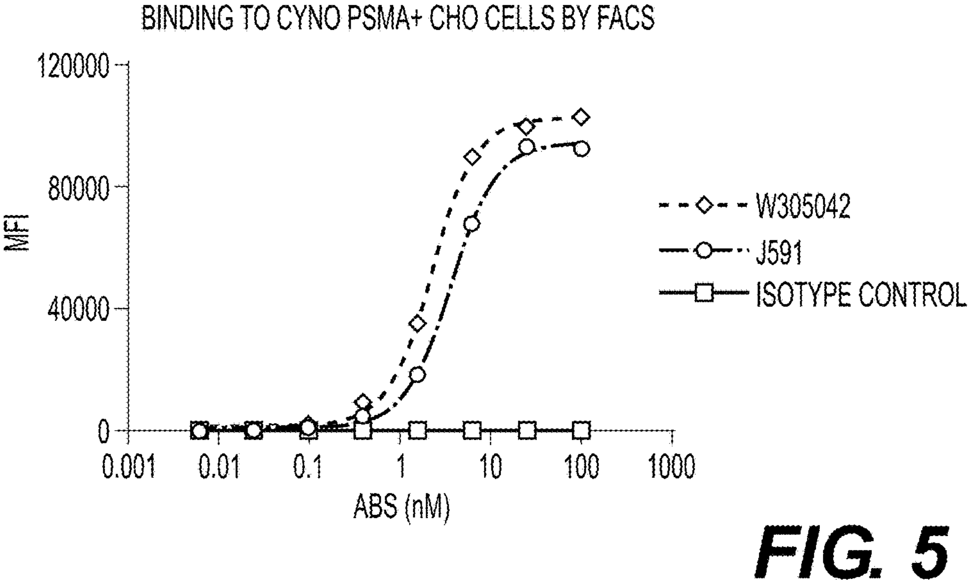
FIG. 5 shows the binding of the antibodies (W305042, J591, and isotope control) to cynomolgus PSMA-expressing CHO cells measured by FACS.

The binding result of antibodies to cynomolgus PSMA-expressing engineered CHO cells is shown in FIG. 5 and Table 4. W305042 could effectively bind to cynomolgus PSMA+ CHO cells with an EC50 of 2.25 nM, which was comparable to the reference antibody J591. Human IgG isotype antibody, which was used as the negative control, showed no obvious binding to cynomolgus PSMA+ CHO cells. The result suggested good binding ability of W305042 to cynomolgus PSMA.

TABLE 4

| Antibodies binding to cynomolgus PSMA-expressing CHO cells | | |
|---|---|---|
| Antibody | $EC_{50}$ (nM) | Max MFI |
| W305042 | 2.25 | 103000 |
| J591 | 3.63 | 93300 |
| Isotype control | >100 | 34.8 |

4.3.3 Binding to Mouse PSMA by ELISA

Briefly, 2 μg/mL mouse PSMA protein (His tag) were coated onto well in ELISA plate in coating buffer for 16 hours in a refrigerator set to 4° C. After washing plate once time with 1×PBST, 200 μL/well 2% BSA were added into wells and incubated for one hour at ambient temperature. After washing three times with 1×PBST, various concentrations of antibodies diluted in 2% BSA (6-fold serially diluted from 100 nM to 0.357 pM for W305042-1.135.2-uIgGIL and isotype control) in a volume of 100 μL/well were added into wells and incubated for one hour at ambient temperature. After washing three times with 1×PBST, 100 μL/well of secondary antibody, Goat anti-human-IgG-Fc-HRP (at 1:5000 dilution) for W305042-1.135.2-uIgGIL and isotype control were added into wells and incubated for one hour at ambient temperature. After washing six times with 1×PBST, 100 μL/well of TMB substrate solution were added into wells and incubated for 5 minutes in dark and then 100 μL/well of 2M HCL were added into wells to stop the reaction. The relative light unit (RLU) were measured at OD450 and OD540 by SPECTRAMAX M5E. EC50 was determined as described above.

Figure 6:
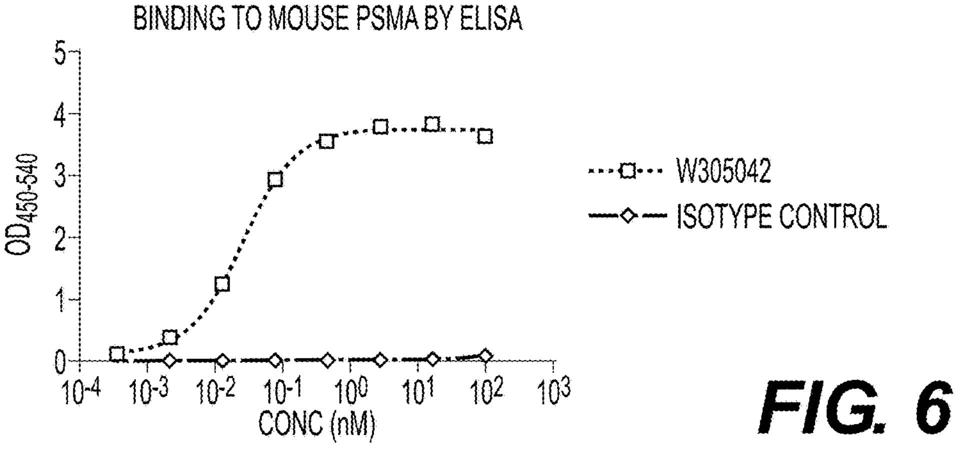
FIG. 6 shows the binding of the antibodies (W305042 and isotope control) to mouse PSMA measured by ELISA.

The result of antibodies binding to mouse PSMA protein is shown in FIG. 6 and Table 5. W305042 could effectively bind to mouse PSMA ECD protein with an EC50 of 0.026 nM. Human IgG isotype antibody, which was used as the negative control, showed no obvious binding to mouse PSMA protein. The result suggested good binding ability of W305042 to mouse PSMA.

TABLE 5

| Antibodies binding to mouse PSMA | | |
|---|---|---|
| Antibody | $EC_{50}$ (nM) | Max $OD_{450}$ |
| W305042 | 0.026 | 3.84 |
| Isotype control | >100 | 0.093 |

4.4 Binding Affinity Test by Surface Plasmon Resonance (SPR)

The binding affinity of W305042 and J591 to human and cynomolgus PSMA were detected by SPR assay using BIACORE 8K. Each antibody was captured on an anti-human IgG Fc antibody immobilized CM5 sensor chip (Cytiva). Human and cynomolgus PSMA at different concentrations were injected over the sensor chip at a flow rate of 30 μL/min for an association phase of 120-180 s, followed by 600-3600 s dissociation. The chip was regenerated by 10 mM glycine (pH 1.5) after each binding cycle.

The sensorgrams of blank surface and buffer channel were subtracted from the test sensorgrams. The experimental data was fitted by 1:1 binding model. Molecular weight of 81.4 and 82.7 kDa were used to calculate the molar concentration of human and cynomolgus PSMA.

The on-rate constants (ka), off-rate constants (kd) and affinity constants (KD) of the antibodies are listed in Table 6. The binding affinity of W305042 to human PSMA was higher than that of J591, and the binding affinity of W305042 to cynomolgus PSMA was similar to J591.

TABLE 6

| Kinetic affinity results of antibodies | | | | |
|---|---|---|---|---|
| Analyte | Ligand | ka (1/Ms) | kd (1/s) | KD (M) |
| Human PSMA | W305042 | 3.81E+05 | 1.12E−05 | 2.94E−11 |
| | J591 | 9.36E+04 | 1.19E−04 | 1.27E−09 |
| Cynomolgus PSMA | W305042 | 2.06E+05 | 5.84E−04 | 2.84E−09 |
| | J591 | 1.06E+05 | 1.92E−04 | 1.82E−09 |

4.5 Developability Test

Thermal Stability by DSF

Figure 7:
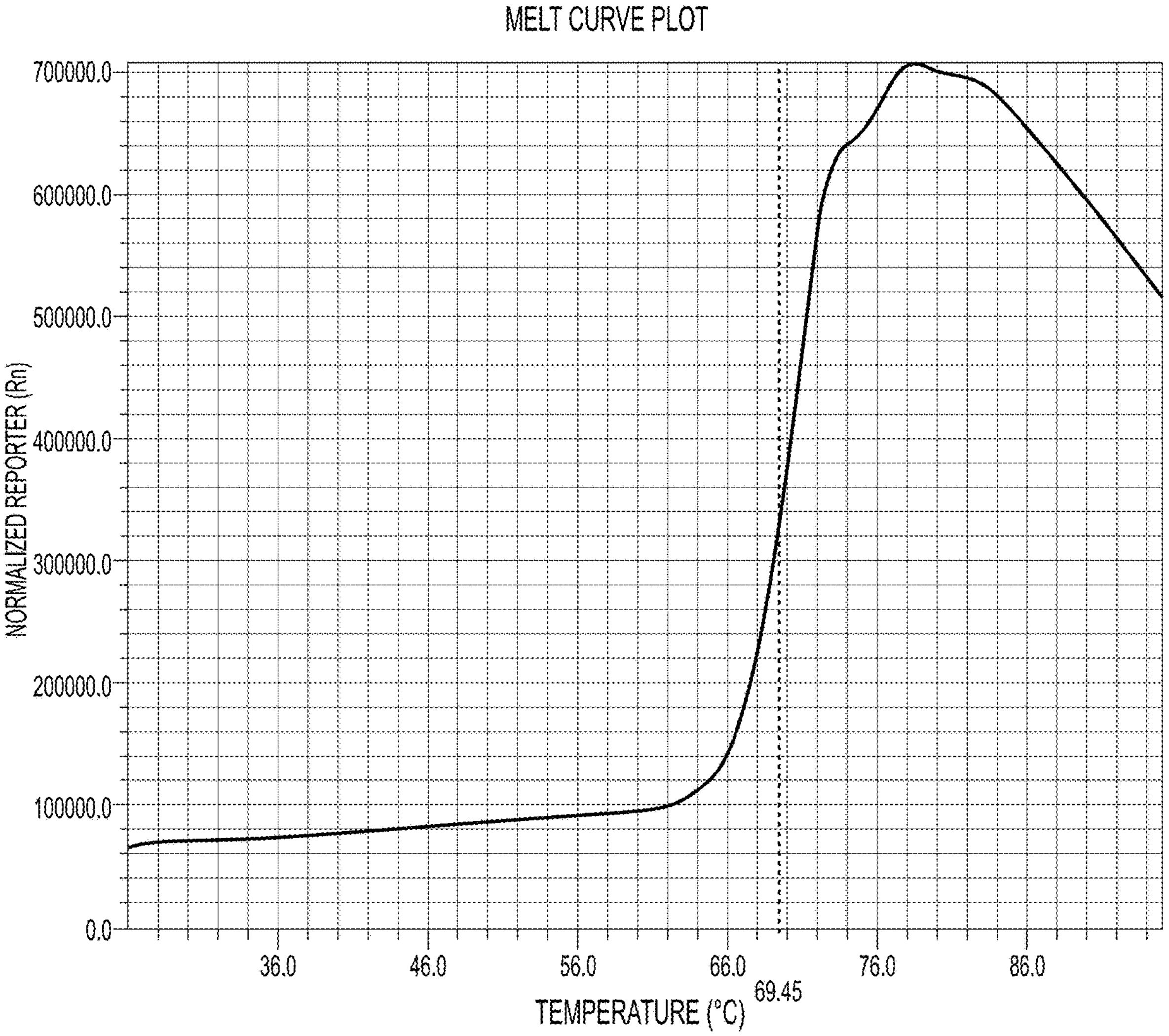
FIG. 7 shows a DSF profile of W305042.

Tm (melting temperature) of each antibody was investigated using QUANTSTUDIO 7 Flex Real-Time PCR system (Applied Biosystems). 19 μL of antibody solution was mixed with 1 μL of 80×SYPRO Orange Protein Gel Stain and transferred to the 96 well plate. The plate was sealed with the Optical Adhesive Film and centrifuged at 3,000 rpm for 5 min to remove any air bubbles. The plate was heated from 26° C. to 95° C. at a rate of 0.9° C./min, and the resulting fluorescence data was collected. The negative derivatives of the fluorescence changes with respect to different temperatures were calculated, and the maximal value was defined as melting temperature Tm. If a protein has multiple unfolding transitions, the first two Tm were reported, named as Tm1 and Tm2. Data collection and Tm calculation were conducted automatically by the QUANTSTUDIO Real-Time PCR software (v1.3). W305042 showed good thermal stability with Tm1 of 69.5° C. and Tm2 of 71.1° C. (FIG. 7).

Determination of Diffusion Interaction Parameter (kD) by DLS kD measurement was investigated using DYNAPRO Plate Reader III (Wyatt Technology). During the sample preparation process, the appearance of samples was recorded at thawing, filtration and concentration. 7.5 μL sample solution was then added to a 1536 well microplate. Data collection was performed by the DYNAMICS operation software (v7.8.1.3). 5 acquisitions were collected for each protein sample while each acquisition time was 5 s. For each measurement, the diffusion coefficient was determined and plotted against protein concentration. kD values were calculated automatically by the software.

W305042 showed high kD value and monodisperse size distribution, indicating that W305042 had good solubility properties. See Table 7.

TABLE 7

| Diffusion interaction parameter (kD) by DLS | | | | | |
|---|---|---|---|---|---|
| Antibody | kD (mL/g) | R^2 | Size Distribution | pI | Buffer |
| W305042 | −5.07 | 0.958 | monodisperse size | 8.35 | PBS |

Hydrophobicity Interaction Chromatography HPLC (HIC-HPLC)

Figure 8:
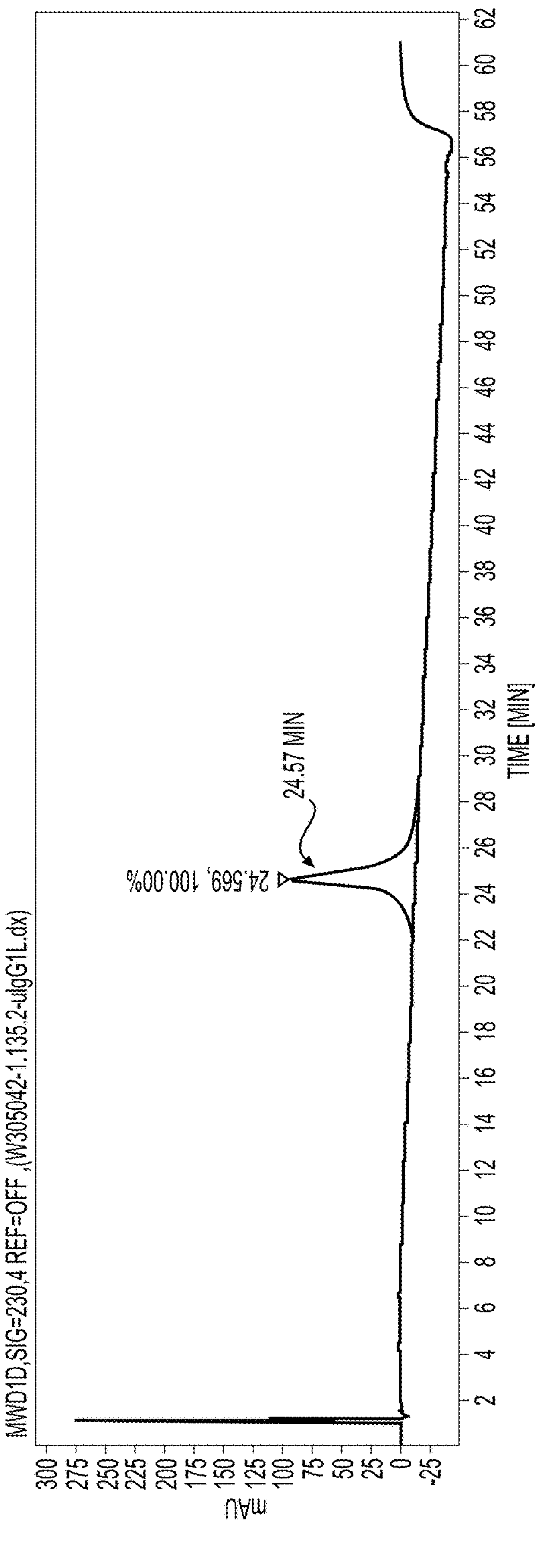
FIG. 8 shows an HIC-HPLC profile of W305042.

Hydrophobicity property of antibody was detected by HPLC 1260 Infinity II system (Agilent Technologics™) with TSKgel butyl-NPR column. The sample was diluted in PBS buffer and 20 μL diluted sample was injected into the column, and separated with a flow rate of 0.5 ml/min for 61 min. The peak retention was detected with UV light of the wavelength 280 nm and 230 nm. The retention time was analyzed with the HIC-HPLC analysis method to integrate all peak areas from 20 min to 40 min. The operation and analysis software are the OPENLAB CDS Workstation (v2.6.0.691). The retention time of W305042 by HIC-HPLC was 24.57 min, indicating that W305042 had low hydrophobicity (FIG. 8).

Example 5. Preparation of Materials, Cell Lines and Benchmark (BMK) Antibodies Information on the commercially available materials used in the following examples are provided in the table immediately below.

| Materials | Vendor | Cat. No. |
|---|---|---|
| Expi293F ™ Cells | Thermo Fisher | Cat. A14527 |
| ExpiFectamine293 transfection kit | Thermo Fisher | Cat. A14524 |
| Expi293F ™ expression medium | Thermo Fisher | Cat. A1435101 |
| Opti-MEM | Gibco | Cat. 31985070 |
| Lipofectamine ™ 2000 Transfection Reagent | Thermo Fisher | Cat. 11668019 |
| Ni column | GE healthcare | Cat. 173712 |
| MabSelect PrismA ™ protein A chromatography resin | Cytiva | 17549802 |
| RESOURCE S cation exchange chromatography column | Cytiva | 17118001 |
| Superdex 200 increase 10/300GL | Cytiva | 28990944 |

-continued

| Materials | Vendor | Cat. No. |
|---|---|---|
| TSKgel G3000SWXL column | Tosoh Bioscience | 0008541 |
| NuPAGE4%-12% Bis-Tris Gel | Thermo Fisher | Cat. NP0322BOX |
| PTS/MCS Cartridges | Charles River | PTS2001 |
| SYPRO Orange Protein Gel Stain | Invitrogen | S6651 |
| TSKgel butyl-NPR column | Tosoh Bioscience | 0042168 |
| Aurora 1536 SQ Lobase Assay Plates | Aurora | ABI1-00110A |
| HT Protein Express Reagent Kit | PerkinElmer | 760499 |
| Human PSMA/FOLH1 protein, His tag | ACRO | PSA-H52H3 |
| Biotinylated Human PSMA/FOLH1 Protein, His, Avitag | ACRO | PSA-H82Qb |
| Cynomolgus PSMA/FOLH1 protein, His tag | ACRO | PSA-C5247 |
| Mouse PSMA/FOLH1 protein, His tag | ACRO | PSA-M5245 |
| Human CD3δ & CD3ε heterodimer protein | SINO | CT038-H2508H |
| RPMI Medium 1640 (1x) | Gibco | 22400-089 |
| F-12K nutrient mixture | Gibco | 21127-022 |
| F-12 (1x) | Gibco | 11765-054 |
| DMEM (1x) | Gibco | 11995-065 |
| FBS | ExCell | FND500 |
| Hygromycin B | Invitrogen | 10687010 |
| DPBS | Corning | 21-031-CVC |
| 0.25% Trypsin-EDTA (1x) | Gibco | 25200-072 |
| Penicillin-Streptomycin | Gibco | 15140122 |
| EDTA (0.5M, pH 8.0) | Invitrogen | AM9260G |
| 4% PFA | Beyotime | P0099 |
| 96-well round bottom microplate | Corning | 3799 |
| White 96-well Microplate with Clear Bottom | PerkinElmer | 6005181 |
| NuncMaxiSorp flat-bottom96 | Thermo | 442404 |
| BovoStar' Bovine Serum Albumin | BovoGen | BSAS 1.0 |
| PBS | MXB biotechnologies | PBS-0061 |
| Tween 20 | Sigma | P1379 |
| TMB substrate solution | Solarbio | PR1200 |
| Goat anti-human-IgG-Fc-HRP | Bethyl | A80-304P |
| Goat anti-human-Fc-Alexa fluor 647 | Jackson ImmunoResearch | 109-605-098 |
| T Cell TransAct ™ human | Miltenyi | 130-111-160 |
| Recombinant Human Interleukin-2(125Ala) | SL Pharma | 1000000 IU |
| EasySep Human T cell enrichment kit | StemCell | #19051 |
| Cell Titer-Glo Luciferase Assay System | Promega | G7573 |
| FITC Mouse Anti-Human CD4 | BD Pharmingen | 550628 |
| PerCP-Cy5.5 Mouse Anti-Human CD8 | BD Pharmingen | 565310 |
| APC Mouse Anti-Human CD25 | BD Pharmingen | 555434 |
| PE Mouse Anti-Human CD69 | BD Pharmingen | 555531 |
| Human IFN-γELISA Set | BD Pharmingen | 555142 |
| Human IL-2 ELISA Set | BD Pharmingen | 555190 |
| Human TNF-αELISA Set | BD Pharmingen | 555212 |
| Human IL-6 ELISA Set | BD Pharmingen | 555220 |
| C4-2 cells | Biovector | / |
| LNCaP cells | ATCC | CRL-1740 |
| 22Rv1 cells | ATCC | CRL-2505 |
| PC-3 cells | ATCC | CRL-1435 |
| Jurkat cells | ATCC | TIB-152 |

Generation of Stable Cell Line

Cynomolgus PSMA-expressing cell line WBP3xx042-FlpinCHO.cPro1.B7 (Cyno PSMA+ CHO cells) was generated using Flp-in CHO cells (Thermo, R75807) transfected with the plasmid encoding full-length cynomolgus PSMA (XM_005579322.1, NCBI) following the user instructions.

Production of Benchmark (BMK) Antibodies

DNA sequences encoding a CD3×PSMA reference antibody, AMG 340/TNB-585 (BMK1), were synthesized according to the SEQ ID Nos. 49&56&61 from WO 2021/222578 A1, and then subcloned into modified pcDNA3.3 expression vectors (Thermo).

DNA sequences encoding a CD3×PSMA reference antibody, AMG 160 (BMK2) were synthesized according to SEQ ID No. 382 from US20170218079A1, and then subcloned into modified pcDNA3.3 expression vectors (Thermo).

The recombinant plasmids expressing reference antibodies were transfected into Expi293 cells. Cells were cultured for 5 days, and supernatant was collected for protein purification using Protein A column (GE Healthcare, 175438) and/or SEC column (Cytiva, 28990944). The obtained antibodies were analyzed by SDS-PAGE and HPLC-SEC, and then stored at −80° C.

Example 6. Generation of the Bispecific Antibody

Anti-CD3 monoclonal antibody was discovered from immunized mouse by hybridoma technology (WO2019057099A1). Anti-PSMA monoclonal antibody was discovered from immunized transgenic rat by hybridoma technology.

Figure 9:
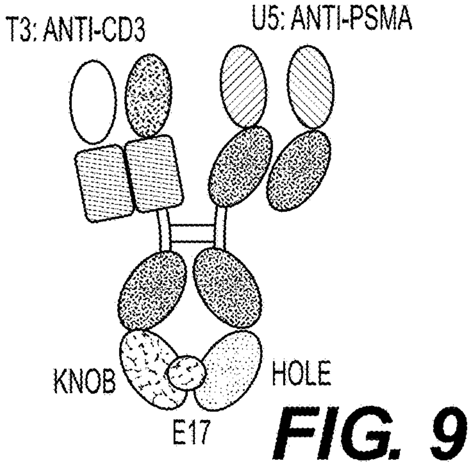
FIG. 9 is a schematic representation of a bispecific CD3×PSMA antibody W308051, wherein T3 represents anti-CD3 arm, wherein the heavy chain variable domain of the anti-CD3 arm is fused to a modified TCR beta constant domain (represented by a gray rectangle) and the hinge-Fc region of human IgG4 with S228P mutation, Fc null mutations (F234A L235A) and knob mutations (S354C-T366W), and VL of the anti-CD3 arm is fused to a modified TCR alpha constant domain (represented by another gray rectangle); and U5 represents anti-PSMA arm, wherein the heavy chain variable domain of the anti-PSMA arm was fused to the hinge-Fc region of human IgG4 with S228P mutation, Fc null mutations (F234A L235A) and hole mutations (Y349C-T366S-L368A-Y407V) and VL of the anti-PSMA arm is fused to CL domain.

Construction of the bispecific antibody was conducted using standard molecular biology protocol. For the construction of the CD3×PSMA bispecific antibody W308051-T3U5.E17-61.uIgG4V322 (W308051) as illustrated in FIG. 9, DNA sequence encoding the VH region of anti-CD3 antibody was fused to a modified TCR beta constant domain and the hinge-Fc region of human IgG4 with S228P mutation, Fc null mutations (F234A L235A) and knob mutations (S354C-T366W); DNA sequence encoding the VL region of anti-CD3 antibody was fused to a modified TCR alpha constant domain; DNA sequence encoding VH region of anti-PSMA antibody was fused to the hinge-Fc region of human IgG4 with S228P mutation, Fc null mutations (F234A L235A) and hole mutations (Y349C-T366S-L368A-Y407V); DNA sequence encoding VL region of anti-PSMA antibody was fused to CL domain. And then coding regions were cloned into modified pcDNA3.3 expression vectors.

The plasmids encoding the bispecific antibody were transfected into Expi293 cells at 1000 ml scale. Cells were cultured for 5 days, and the supernatant was collected for protein purification using Protein A column (Cytiva, 17549802) and CEX column (Cytiva, 17118001). The antibody concentration was detected by Nano Drop at 280 nm. The purity of the antibody was analyzed by SDS-PAGE and SEC-HPLC. Endotoxin level was determined by PTS/MCS Cartridges. The antibody was stored at −80° C.

Figure 10A:
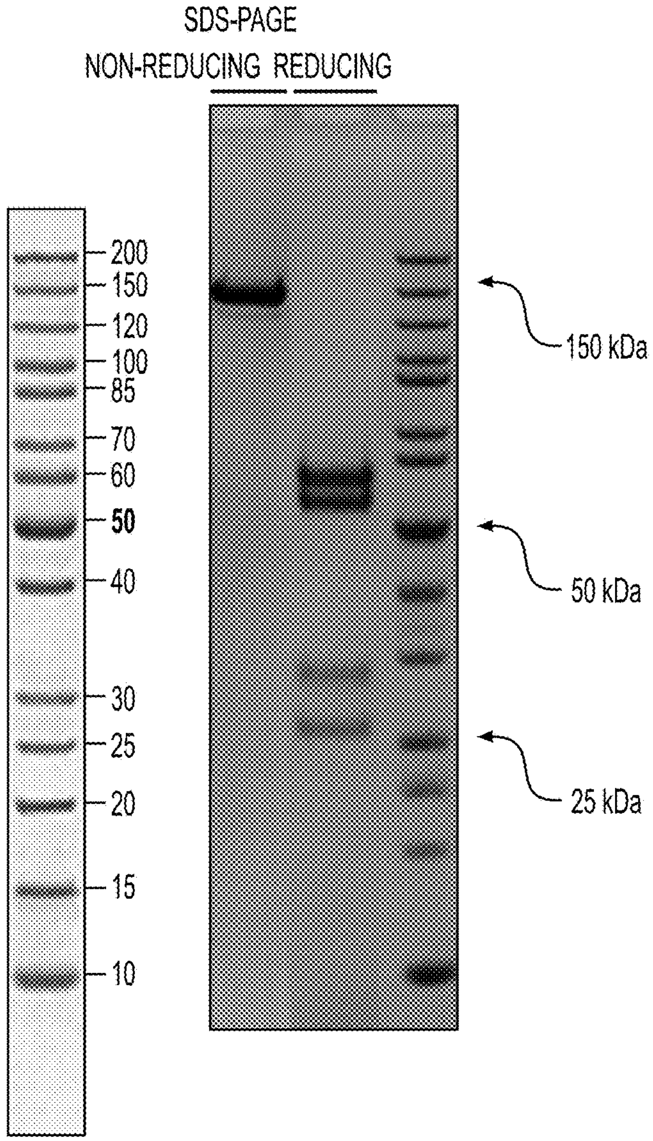
FIGS. 10A and 10B show the results of SDS-PAGE (FIG. 10A) and SEC-HPLC (FIG. 10B) analysis of W308051.
Figure 10B:
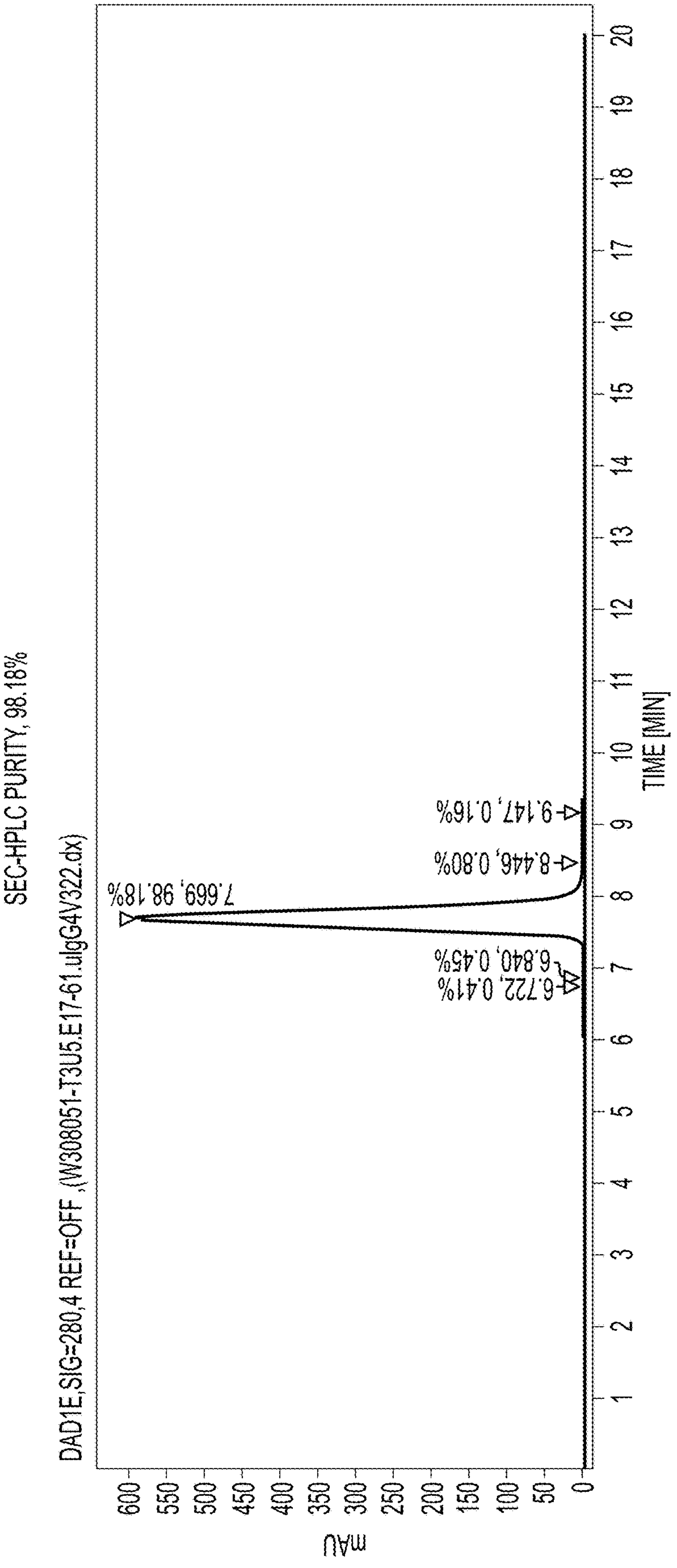

As shown in FIGS. 10A and 10B, the yield of W308051 was 79.22 mg/L, and the purity by SEC-HPLC was 98.18%.

Example 7. In Vitro Characterization

7.1 Target Binding Measured by ELISA/FACS

Binding to Human PSMA Measured by ELISA

Briefly, 1 μg/mL human PSMA protein (His tag) were coated onto wells in ELISA plate in coating buffer at 4° C. for 16 hours. After washing the plate with 1×PBST once, the plate was blocked by using 200 μL/well 2% BSA for one hour. After washing the plate for three times with 1×PBST, various concentrations of antibodies diluted in 2% BSA (5-fold serially diluted from 200 nM to 0.004096 pM) were added to the wells and the plate was incubated for one hour at ambient temperature. After washing the plate three times with 1×PBST, Goat anti-human-IgG-Fc-HRP (at 1:5000 dilution) was added into wells and incubated for one hour. After washing six times with 1×PBST, 100 μL/well of TMB substrate solution was added into wells and incubated for 5 minutes in dark and then 100 μL/well of 2M HCl was added into wells to stop the reaction. The relative light unit (RLU) was measured at $OD_{450}$ and $OD_{540}$ by SPECTRAMAX M5E. The binding $EC_{50}$ was calculated by GraphPad Prism 7 software by plotting antibody concentration (x-axis) versus $OD_{450-540}$ (y-axis) and analyzing as: Nonlinear regression (curve fit)-log (agonist) vs. response-Variable slope (four parameters).

Figure 11:
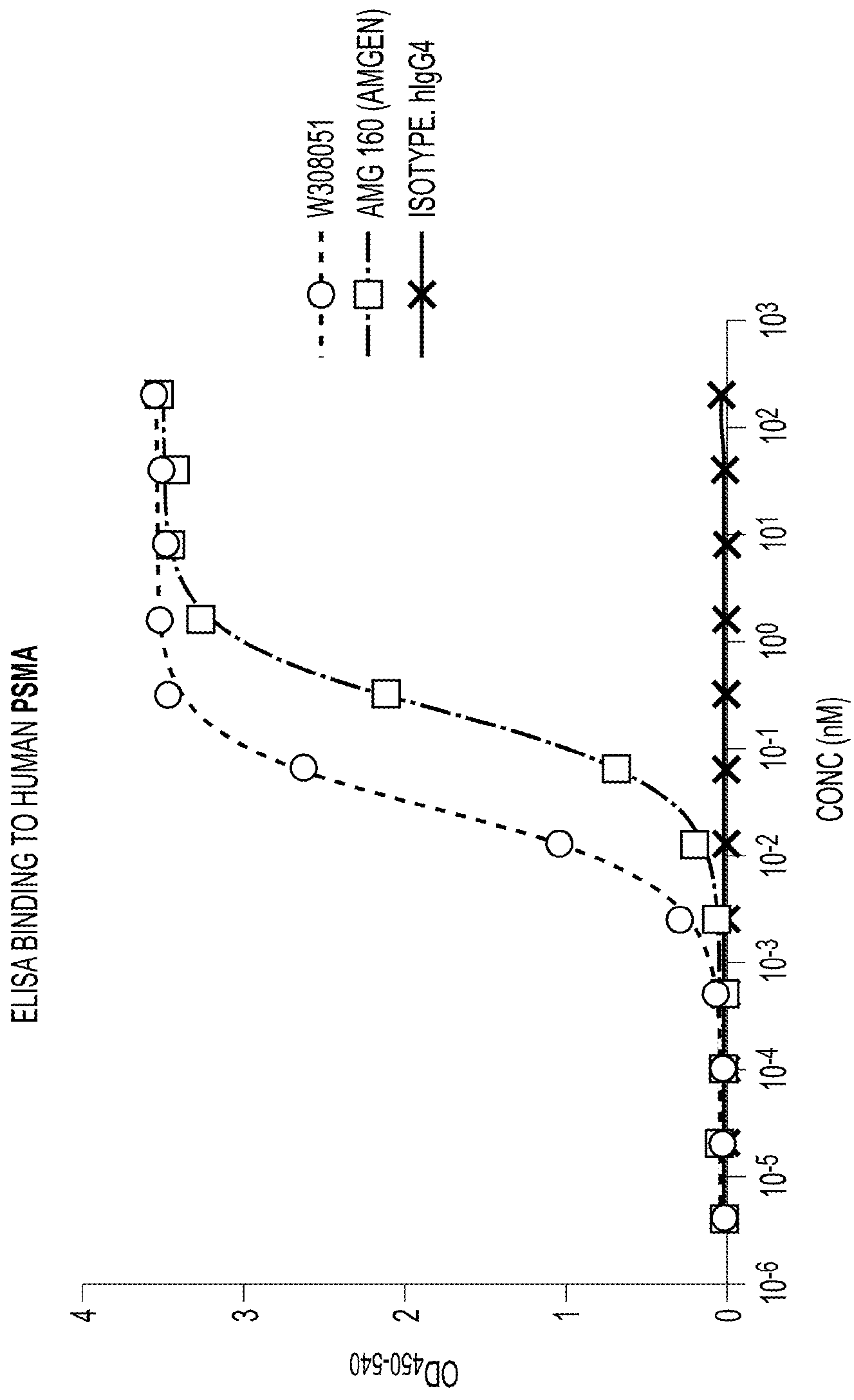
FIG. 11 shows the binding of the antibodies (W308051, AMG160, and isotype hIgG4 control) to human PSMA measured by ELISA.

The results were shown in FIG. 11 and Table 8, W308051 binds to human PSMA protein with an $EC_{50}$ of 0.027 nM, which was more potent than that of the reference antibody AMG 160.

TABLE 8

$EC_{50}$ of antibodies to human PSMA

| | Human PSMA ECD protein | |
|---|---|---|
| Antibody | $EC_{50}$ (nM) | Max $OD_{450-540}$ |
| W308051 | 0.03 | 3.55 |
| AMG 160 | 0.22 | 3.52 |
| Isotype. hIgG4 | NA | 0.04 |

NA: Not applicable.

Binding to Human PSMA and CD3 Measured by FACS

Four human prostate cancer cells, human C4-2 (with high PSMA expression), LNCaP (with high PSMA expression), and 22Rv1 (with low PSMA expression), PC-3 (PSMA negative), as well as Jurkat 2B8 (CD3 positive) cells and primary T cells isolated from fresh PBMCs ($5\times10^4$ cells) were incubated with various concentrations of antibodies (5-fold serially diluted from 200 nM to 2.56 pM for W308051, AMG160 and isotype control, 5-fold serially diluted from 500 nM to 6.40 pM for AMG 340) at 4° C. for one hour. After washing twice with 1×PBS/1% BSA/0.1 mM EDTA, Alexa fluor 647-labeled goat anti-human IgG Fc (at 1:500 dilution) was added and the plate was incubated at 4° C. for half an hour in dark. After washing twice with 1×PBS/1% BSA/0.1 mM EDTA, cells were re-suspended in 1×PBS/1% BSA/0.1 mM EDTA, and mean fluorescence intensity (MFI) was measured by a flow cytometer and analyzed by FLOWJO. The binding $EC_{50}$ was calculated by GraphPad Prism 7 software by plotting antibody concentration (x-axis) versus $OD_{450-540}$ (y-axis) and analyzing as: Nonlinear regression (curve fit)-log (agonist) vs. response-Variable slope (four parameters).

Figure 12:
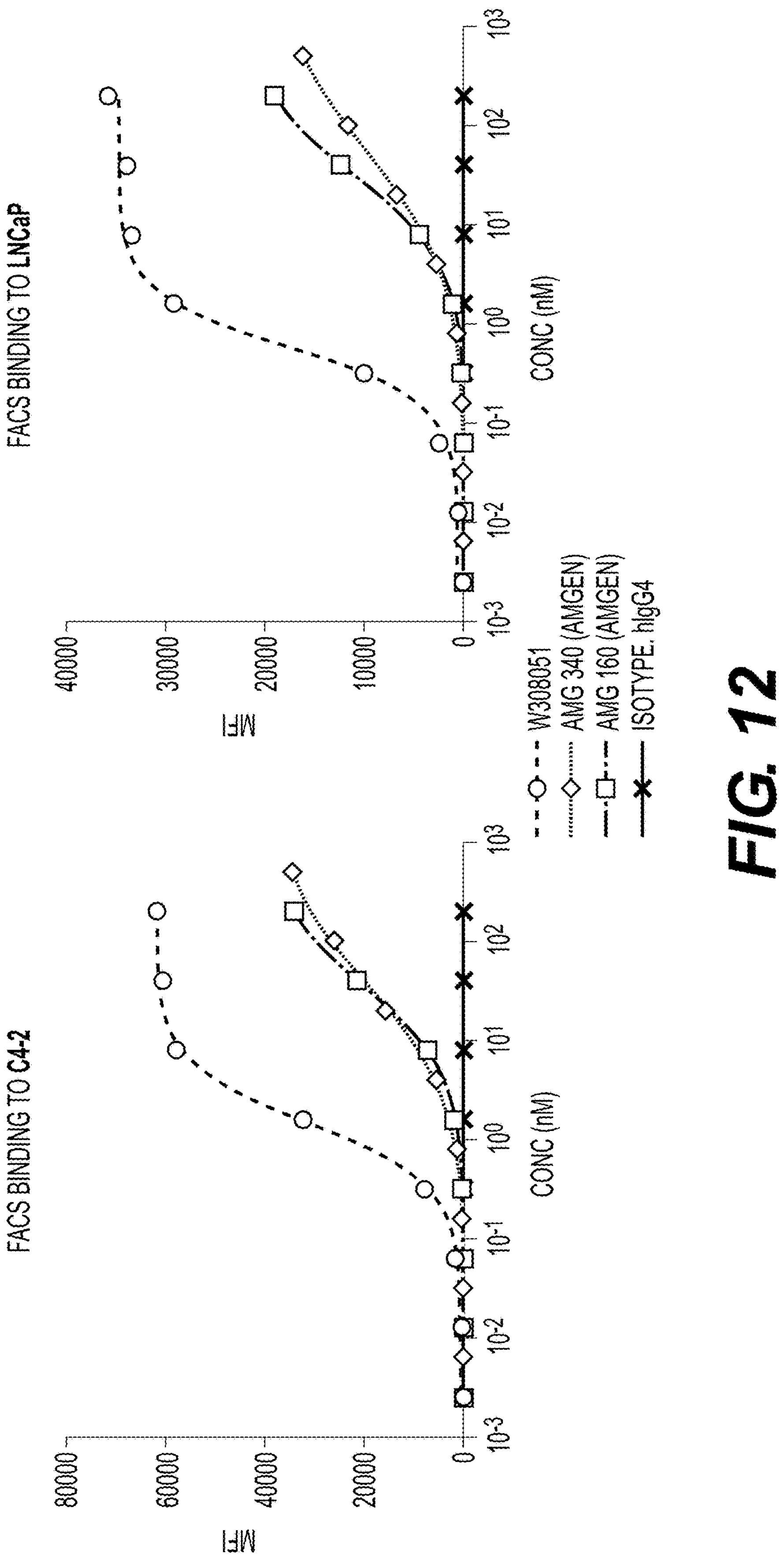
FIG. 12 shows the binding of the antibodies (W308051, AMG340, AMG160, and isotype hIgG4 control) to human C4-2 (with high PSMA expression), LNCaP (with high PSMA expression), 22Rv1 (with low PSMA expression) and PC-3 cells (PSMA negative) measured by FACS.
Figure 12:
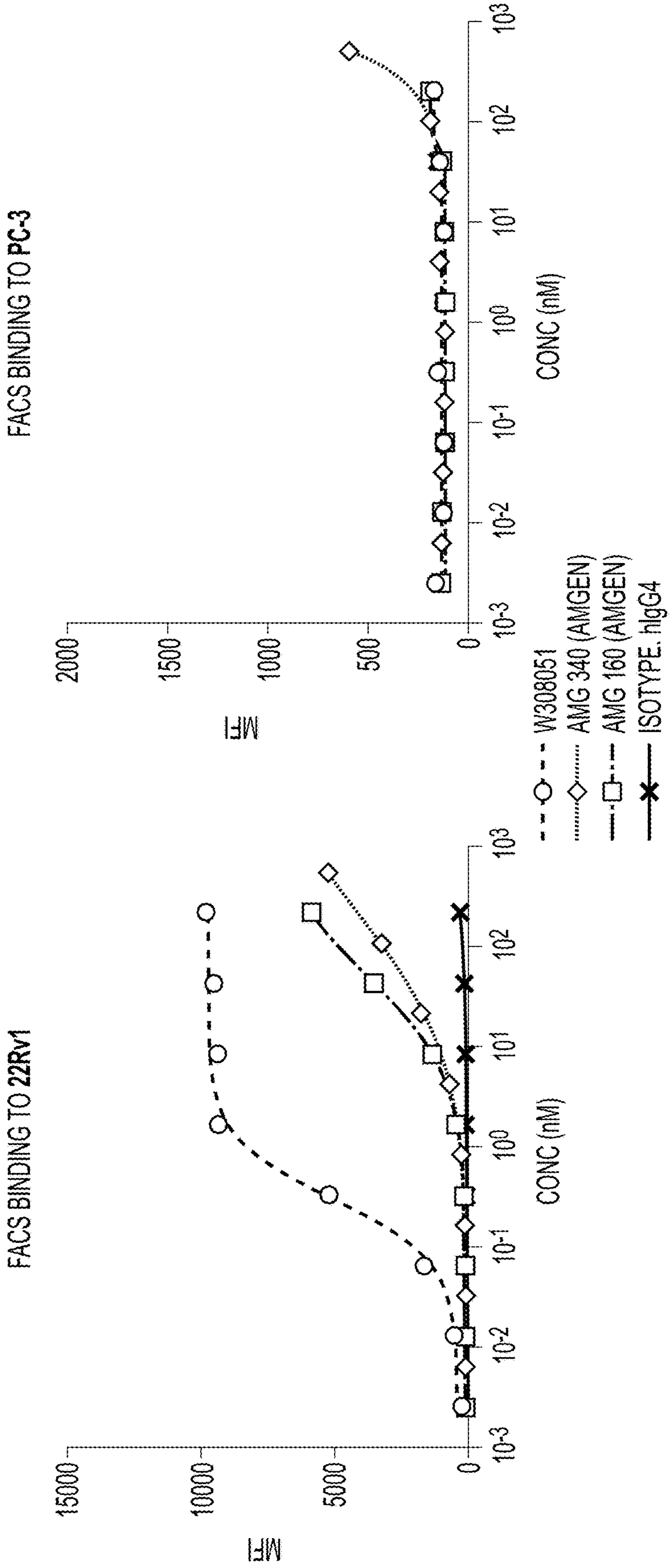
Figure 13:
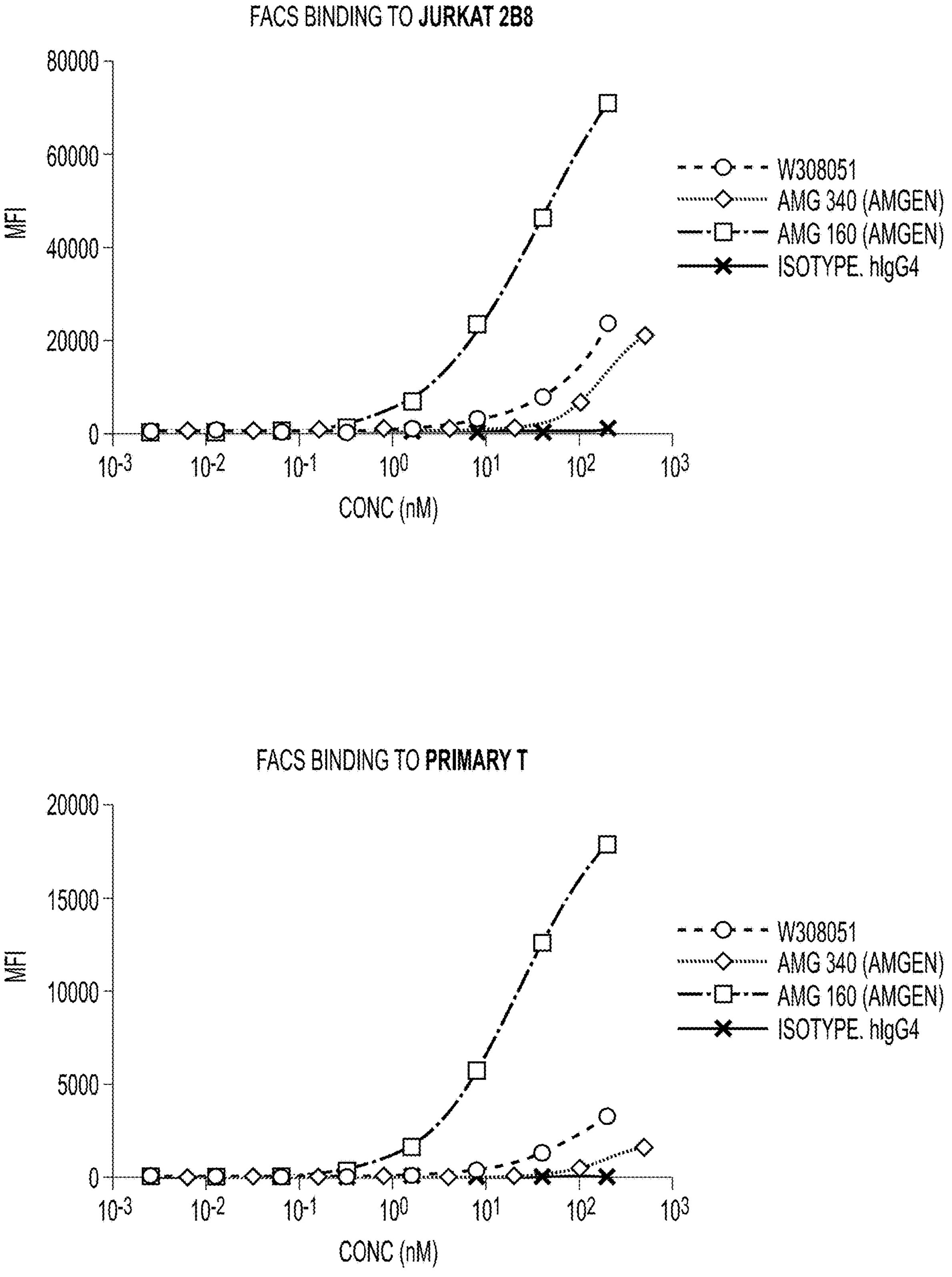
FIG. 13 shows the binding of the antibodies (W308051, AMG340, AMG160, and isotype hIgG4 control) to CD3 positive Jurkat cells and primary human T cells as measured by FACS.

The results were shown in FIGS. 12-13 and Table 9. As shown in FIG. 12 and Table 9, W308051 bound to human PSMA positive C4-2 (with high PSMA expression), LNCaP (with high PSMA expression) and 22Rv1 (with low PSMA expression) human tumor cells with $EC_{50}$ of 1.48 nM, 0.58 nM and 0.29 nM, respectively, indicating that W308051 was more potent than AMG 160 and AMG 340. Meanwhile, W308051 did not bind to PSMA negative PC-3 cell line. As shown in FIG. 13, W308051 bound to CD3 positive Jurkat cells and primary human T cells with lower binding affinity than AMG 160.

TABLE 9

Binding of the antibodies to PSMA positive and negative cells

| | C4-2 (PSMA High) | | LNCaP (PSMA High) | | 22Rv1 (PSMA Low) | | PC-3 (PSMA Negative) | |
|---|---|---|---|---|---|---|---|---|
| Antibody | $EC_{50}$ (nM) | Max MFI | EC50 (nM) | Max MFI | EC50 (nM) | Max MFI | EC50 (nM) | Max MFI |
| W308051 | 1.48 | 62000 | 0.58 | 35900 | 0.29 | 9861 | NA | 177 |
| AMG 340 | ~35.3 | 34700 | ~55.7 | 16300 | ~174.2 | 5279 | NA | 599 |
| AMG 160 | ~34.4 | 34200 | ~30.8 | 19100 | ~46.1 | 5910 | NA | 198 |
| Isotype. hIgG4 | NA | 138 | NA | 181 | NA | 372 | NA | 187 |

NA: Not applicable.

3.2 Cross Species Binding Measured by ELISA/FACS

Binding to Cyno and Mouse PSMA Measured by ELISA

Briefly, 1 μg/mL cynomolgus PSMA protein (His tag) and 2 μg/mL mouse PSMA protein (His tag) were coated onto wells in an ELISA plate in coating buffer at 4° C. for 16 hours. After washing plate with 1×PBST once, the plate was blocked by using 200 μL/well 2% BSA for one hour. After washing three times with 1×PBST, various concentrations of antibodies diluted in 2% BSA (5-fold serially diluted from 200 nM to 0.004 pM for W308051, AMG 160 and isotype control for cynomolgus PSMA, 6-fold serially diluted from 100 nM to 0.357 pM for W308051, AMG 160 and isotype control for mouse PSMA and 6-fold serially diluted from 500 nM to 1.786 pM for AMG 340 for mouse PSMA) were added and incubated for one hour at ambient temperature. After washing three times with 1×PBST, Goat anti-human-IgG-Fc-HRP (at 1:5000 dilution) was added and incubated for one hour. After washing six times with 1×PBST, 100 μL/well of TMB substrate solution was added into wells and incubated for 5 minutes in dark and then 100 μL/well of 2M HCL were added into wells to stop the reaction. The relative light unit (RLU) was measured at $OD_{450}$ and $OD_{540}$ by SPECTRAMAX M5E. $EC_{50}$ was determined as described above.

Figure 14A:
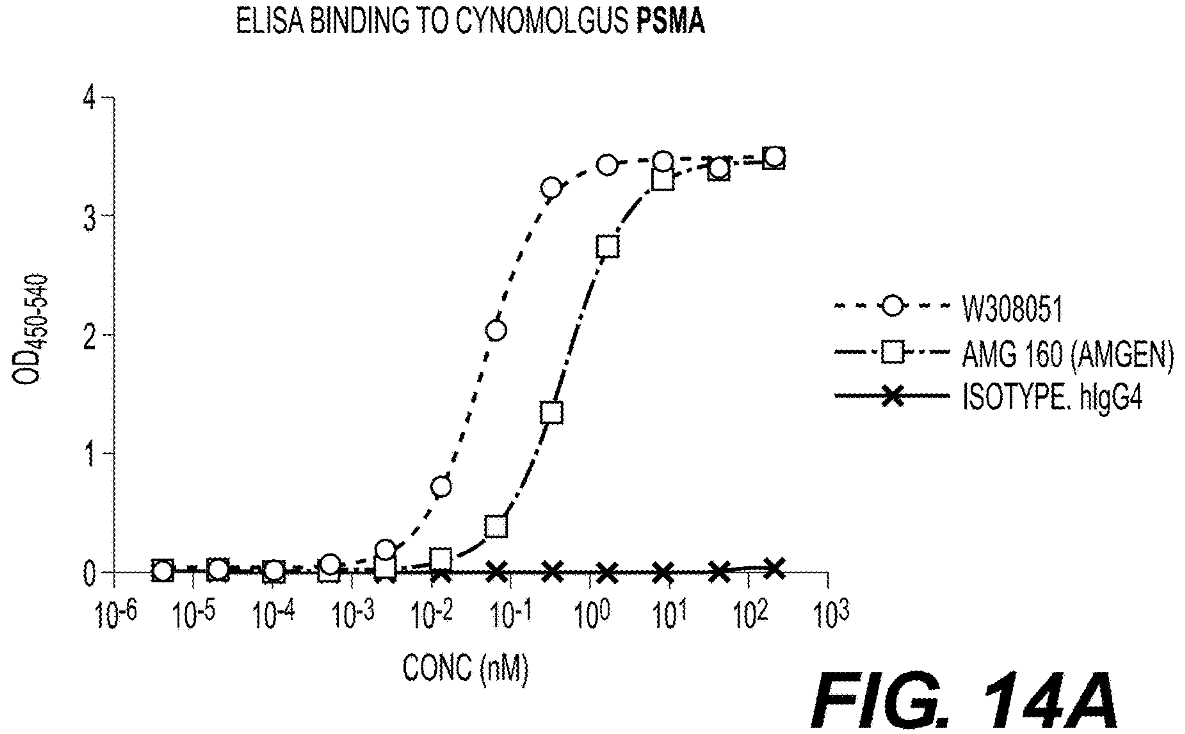
FIGS. 14A and 14B show the binding of the antibodies (W308051, AMG160, and isotype hIgG4 control) to Cynomolgus PSMA (FIG. 14A) and mouse PSMA (FIG. 14B) measured by ELISA.
Figure 14B:
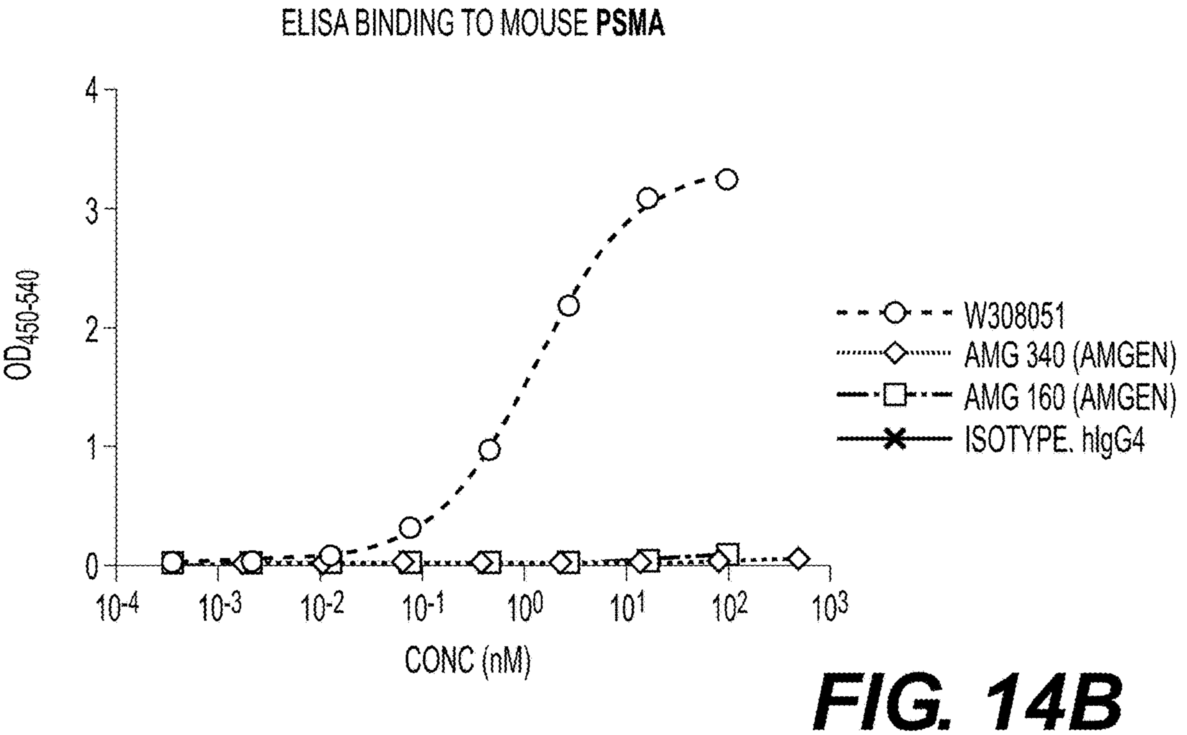

As shown in Tables 10-11 and FIGS. 14A and 14B, W308051 cross-reacted with cynomolgus and mouse PSMA. W308051 bounded to cyno PSMA ECD protein with an $EC_{50}$ of 0.045 nM, which was more potent than AMG 160. W308051 also bound to mouse ECD PSMA protein with an $EC_{50}$ of 1.34 nM, whereas AMG 160 and AMG 340 did not bind to mouse PSMA protein.

TABLE 10

Binding to Cynomolgus PSMA

| | Cynomolgus PSMA ECD Protein | |
|---|---|---|
| Antibody | $EC_{50}$ (nM) | Max $OD_{450-540}$ |
| W308051 | 0.05 | 3.50 |
| AMG 160 | 0.48 | 3.57 |
| Isotype. hIgG4 | NA | 0.04 |

NA: Not applicable.

TABLE 11

Binding to mouse PSMA

| | Mouse PSMA ECD Protein | |
|---|---|---|
| Antibody | $EC_{50}$ (nM) | Max $OD_{450-540}$ |
| W308051 | 1.34 | 3.25 |
| AMG 340 | NA | 0.05 |
| AMG 160 | NA | 0.09 |
| Isotype. hIgG4 | NA | 0.09 |

NA: Not applicable.

Binding to Cynomolgus PSMA Positive Cells Measured by FACS

WBP3xx042-FlpinCHO.cPro1.B7 ($5\times10^4$ cells) was incubated with various concentrations of antibodies 4° C. for one hour. After washing twice with 1×PBS/1% BSA/0.1 mM EDTA, secondary antibody, Alexa fluor 647-labeled goat anti-human IgG Fc, was added and the plate was incubated at 4° C. for half an hour in dark. After washing twice with 1×PBS/1% BSA/0.1 mM EDTA, cells were re-suspended in 1×PBS/1% BSA/0.1 mM EDTA. MFI and $EC_{50}$ were determined as described above.

Figure 15:
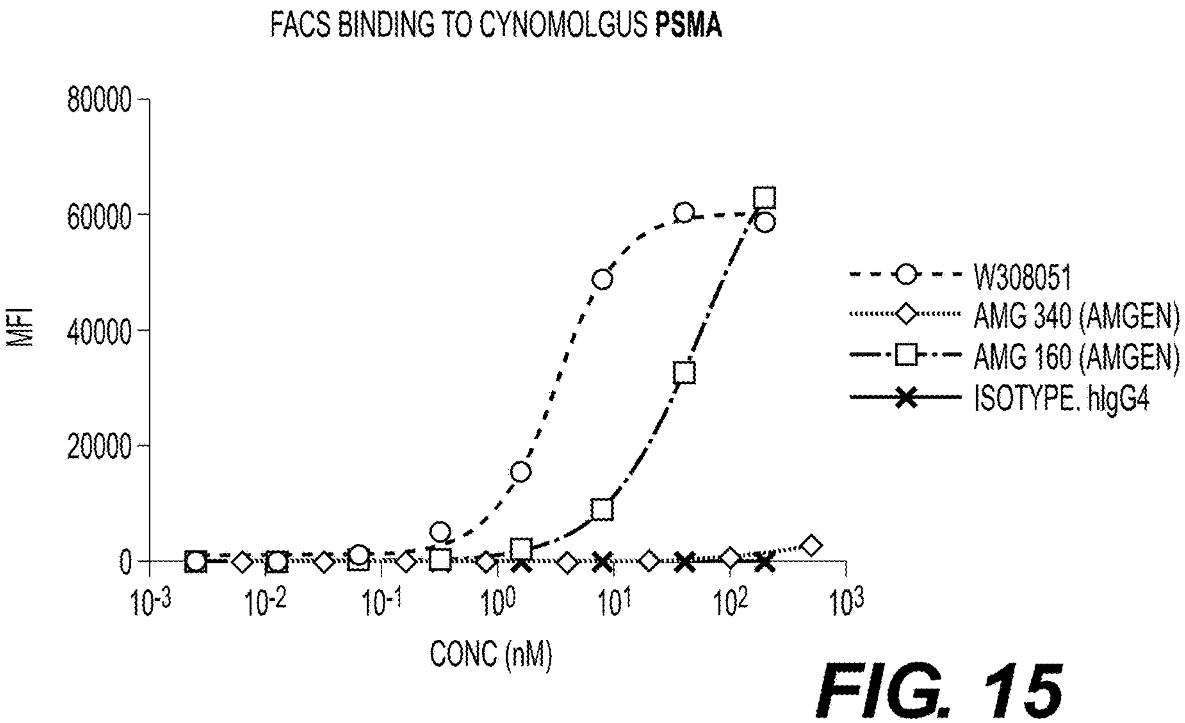
FIG. 15 shows the binding of the antibodies (W308051, AMG340, AMG160, and isotype hIgG4 control) to Cynomolgus PSMA positive cells measured by FACS.

As shown in FIG. 15 and Table 12, W308051 bound to Cynomolgus PSMA positive cells with an $EC_{50}$ of 3.20 nM, which was more potent than AMG 160 and AMG 340.

TABLE 12

Binding to Cynomolgus PSMA positive cells

| | FlpInCHO-cyno PSMA | |
|---|---|---|
| Antibody | $EC_{50}$ (nM) | Max MFI |
| W308051 | 3.20 | 58700 |
| AMG 340 | NA | 2866 |
| AMG 160 | ~55.8 | 62900 |
| Isotype. hIgG4 | NA | 19.90 |

NA: Not applicable.

7.3 Affinity Measured by SPR

The binding affinity of antibodies W308051, AMG 340, and AMG 160 to human PSMA was detected by SPR assay using BIACORE 8K. Biotinylated human PSMA was captured on a streptavidin-immobilized CM5 sensor chip (Cytiva). Antibodies at different concentrations were injected over the sensor chip in an injection type of single-cycle at a flow rate of 30 μL/min for an association phase of 180 s, followed by 600-3600 s dissociation. The chip was then regenerated by 10 mM glycine (pH1.5) at the last binding cycle.

The sensorgrams of the blank surface and buffer channel were subtracted from the test sensorgrams. The experimental data were fitted by 1:1 binding model. The molecular weight of 147, 111, and 106 KDa were used to calculate the molar concentration of W308051, AMG 340, and AMG 160, respectively.

The binding affinity of antibodies W308051, AMG 340, and AMG 160 to human CD3δ & CD3ε heterodimer was detected by SPR assay using BIACORE 8K. Each antibody was captured on an anti-human IgG Fc antibody immobilized CM5 sensor chip (Cytiva). human CD3δ & CD3ε heterodimer at different concentrations were injected over the sensor chip at a flow rate of 30 μL/min for an association phase of 120 s, followed by 240 s dissociation. The chip was regenerated by 10 mM glycine (pH 1.5) after each binding cycle.

The sensorgrams of blank surface and buffer channel were subtracted from the test sensorgrams. The experimental data was fitted by 1:1 binding model. Molecular weight of 31 kDa was used to calculate the molar concentration of human CD3δ & CD3ε heterodimer.

The full kinetic affinities of W308051 to human PSMA and CD3 were shown in Table 13. The affinity of W308051 to human PSMA and CD3 was $1.58\times10^{-11}$ M and $6.02\times10^{-8}$ M respectively.

TABLE 13

| Affinity to human PSMA and CD3 measured by SPR | | | | |
|---|---|---|---|---|
| Analyte | Ligand | $k_a$ (1/Ms) | $k_d$ (1/s) | $K_D$ (M) |
| Human PSMA Protein | W308051 | $8.80 \times 10^5$ | $1.39 \times 10^{-5}$ | $1.58 \times 10^{-11}$ |
| (His Tag & biotin | AMG 340 | $1.17 \times 10^5$ | $3.78 \times 10^{-3}$ | $3.23 \times 10^{-8}$ |
| label) | AMG 160 | $2.23 \times 10^4$ | $8.16 \times 10^{-4}$ | $3.67 \times 10^{-8}$ |
| Human CD3δ & CD3ε | W308051 | $5.50 \times 10^5$ | $3.31 \times 10^{-2}$ | $6.02 \times 10^{-8}$ |
| Heterodimer Protein | AMG 340 | | No or weak binding | |
| (Flag & His Tag) | AMG 160 | $1.23 \times 10^5$ | $2.22 \times 10^{-3}$ | $1.81 \times 10^{-8}$ |

7.4 T Cell Cytotoxicity and Cytokine Release

The efficacy of the bispecific antibody to mediate tumor cell lysis by human T cells was evaluated by CTG based cytotoxicity assay. Briefly, C4-2, LNCaP and PC-3 cells were used as target cells, and human T cells were isolated from fresh human PBMCs and used as effector cells. 150 μL/well antibodies were added into 96-well plates. Then, effector cells ($1\times10^5$ cells/50 μL/well) and target cells ($1\times10^4$ cells/50 μL/well) were added into corresponding wells (E/T ratio=10:1). After incubation for 72 hours, plates were washed once with DPBS and CTG solution (75 μL/well) was added and incubated at ambient temperature for 10 minutes. Relative light unit (RLU) signal was measured by Invasion reader. Cytotoxicity % was calculated as: $(1-(RLU_{sample}-RLU_{effector\ cell\ only})/(RLU_{Effector+target\ cell}-RLU_{effector\ cell\ only}))\times100\%$. The $IC_{50}$ was calculated by GraphPad Prism 7 software through plotting antibody concentration (x-axis) versus cytotoxicity % (y-axis) and analyzing as: Nonlinear regression (curve fit)-log (inhibitor) vs. response-Variable slope (four parameters).

Released cytokine levels in the supernatants were determined by ELISA based quantification assay. Briefly, after incubation for 20 hours, 125 μL supernatant was collected and stored at 4° C. Human IFN-γ release was measured by ELISA and recombinant human IFN-γ was used to make standard curve. The plates were pre-coated with 50 μL/well of capture antibody specific for human IFN-γ (1:250) at 4° C. overnight. After blocking with 2% BSA for one hour, 50 μL of standards or samples were added into each well and incubated at ambient temperature for two hours. After washing three times with 1×PBST, 50 μL of biotin-conjugated human IFN-γ detection antibody (1:250) and peroxidase conjugated streptavidin (1:250) were added into each well and incubated at ambient temperature for one hour. After washing six times with 1×PBST, the color was developed by dispensing 50 μL of TMB substrate and then stopped by 50 μL of 2M HCL. The relative light unit (RLU) were measured at $OD_{450}$ and $OD_{540}$ by SPECTRAMAX M5E. The concentration of human IFN-γ in supernatant was quantitated according to the standard curve.

Figure 16:
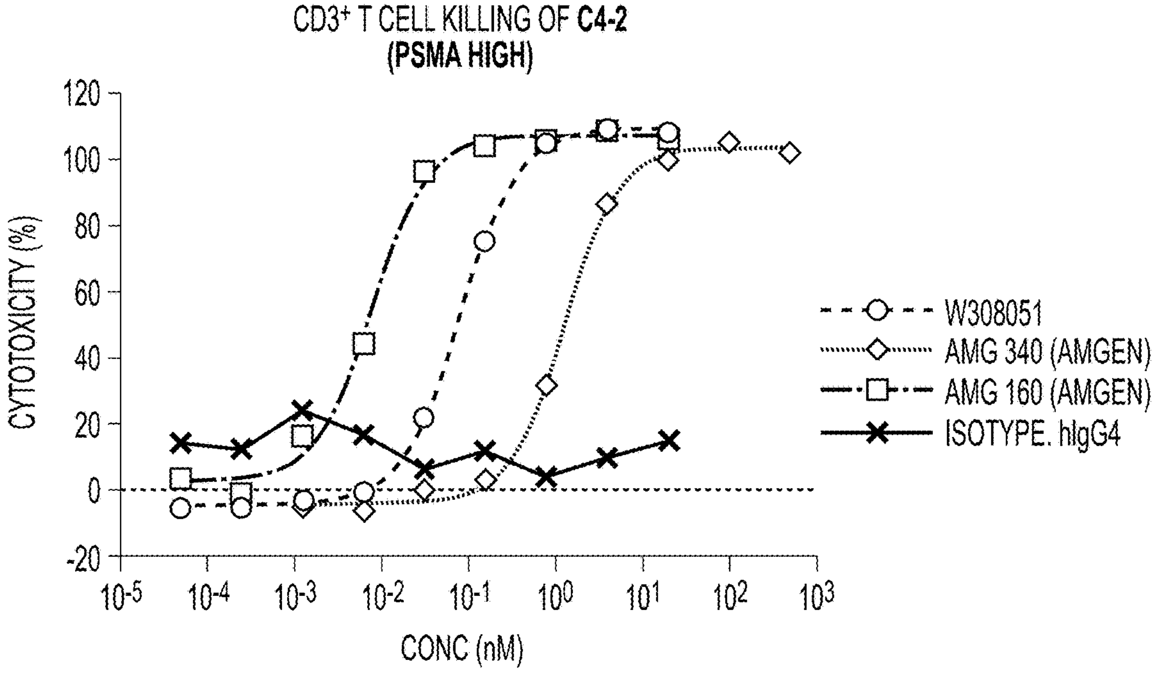
FIG. 16 shows T cell cytotoxicity of C4-2 cells, LNCaP cells, and PC-3 cells co-cultured with CD3+ T cells, incubated with the antibodies W308051, AMG340, AMG160, and isotype hIgG4 control.
Figure 16:
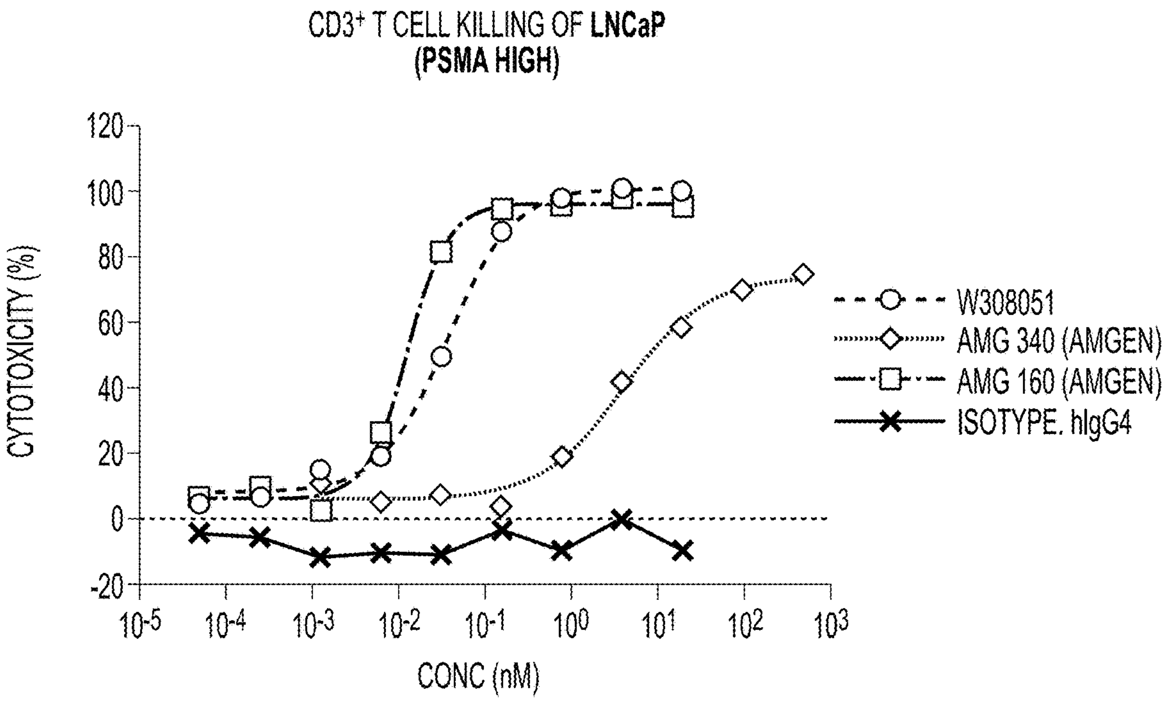
Figure 16:
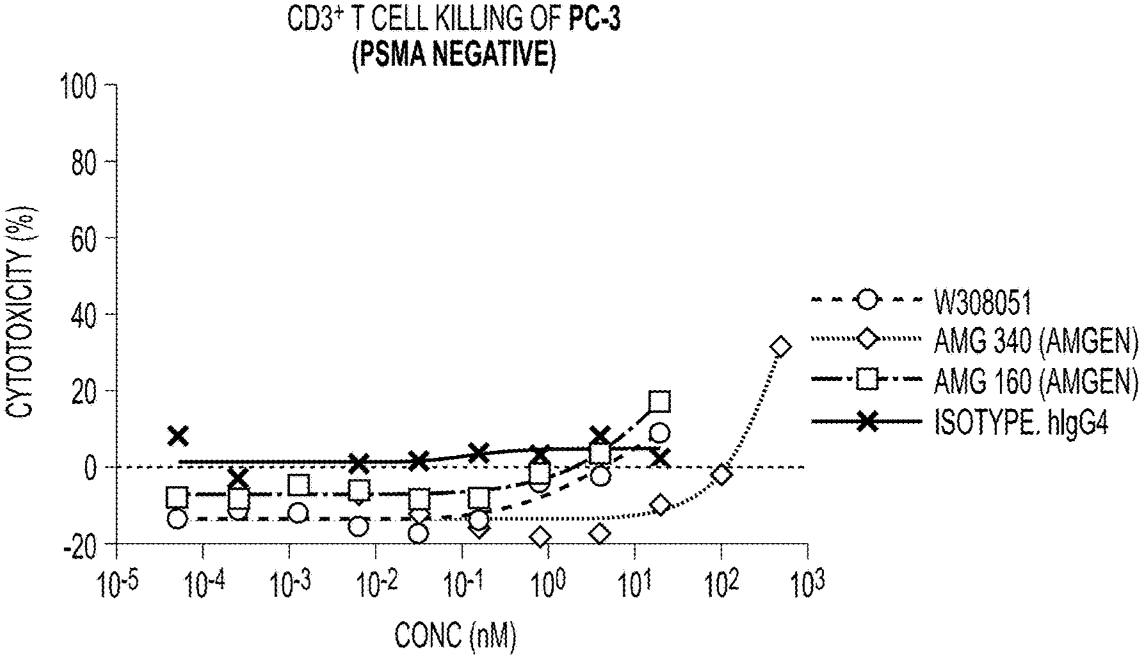
Figure 17:
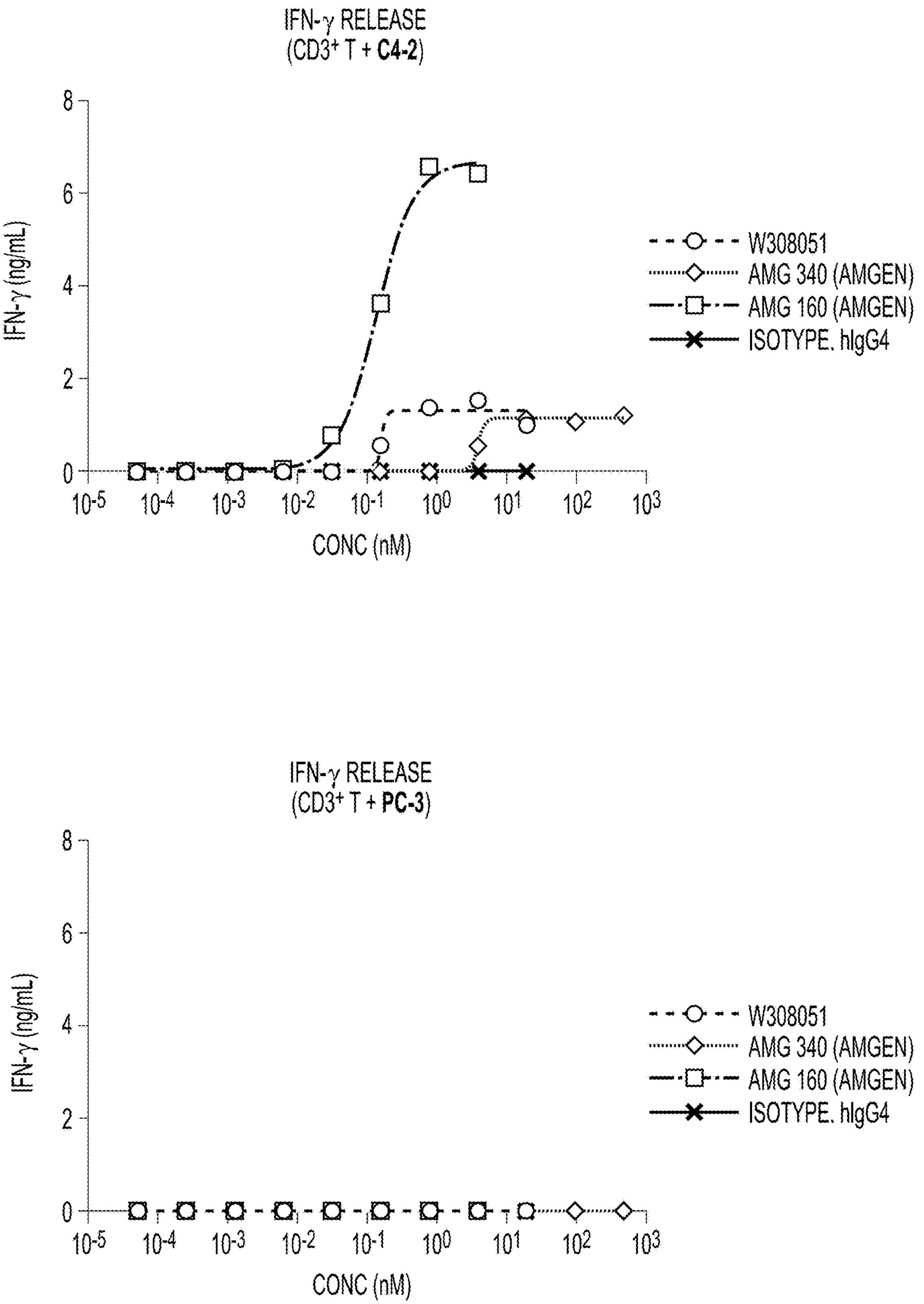
FIG. 17 shows cytokine release of C4-2 and PC-3 cells co-cultured with CD3+ T cells, incubated with the antibodies W308051, AMG340, AMG160, and isotype hIgG4 control.

As shown in FIGS. 16-17 and Tables 14-15, the results demonstrated that W308051 induced potent cytotoxicity and minimal IFN-γ release in the co-culture of PSMA+ tumor cells and CD3+ T cells, but no cytotoxicity and cytokine release in the co-culture of PSMA negative PC-3 cells and CD3+ T cells.

TABLE 14

T cell cytotoxicity of C4-2, LNCaP and PC-3 cells co-cultured with CD3+ T cells

| | $CD3^+$ T + C4-2 | | $CD3^+$ T + LNCaP | | $CD3^+$ T + PC-3 | |
|---|---|---|---|---|---|---|
| Antibody | $IC_{50}$ (nM) | Max Cytotoxicity (%) | $IC_{50}$ (nM) | Max Cytotoxicity (%) | $IC_{50}$ (nM) | Max Cytotoxicity (%) |
| W308051 | 0.082 | 109.38 | 0.037 | 100.94 | NA | 9.21 |
| AMG 340 | 1.29 | 105.61 | 4.15 | 75.01 | NA | 32.02 |
| AMG 160 | 0.008 | 108.71 | 0.013 | 98.22 | NA | 17.35 |
| Isotype. hIgG4 | NA | 24.08 | NA | 0.056 | NA | 8.48 |

NA: Not applicable.

TABLE 15

| Cytokine Release of C4-2 and PC-3 cells co-cultured with CD3+ T cells | | | | |
|---|---|---|---|---|
| | CD3⁺ T + C4-2 | | CD3⁺ T + PC-3 | |
| Antibody | $EC_{50}$ (nM) | Max IFN-γ (ng/mL) | $EC_{50}$ (nM) | Max IFN-γ (ng/mL) |
| W308051 | ~0.16 | 1.53 | NA | 0.00 |
| AMG 340 | ~4.03 | 1.22 | NA | 0.00 |
| AMG 160 | ~0.14 | 6.58 | NA | 0.00 |
| Isotype. hIgG4 | NA | 0.00 | NA | 0.00 |

NA: Not applicable.

7.5 Cytokine Release of C4-2 Cells Co-Cultured with PBMCs

Briefly, 100 μL/well antibodies (10-fold serially diluted from 20 nM to 0.2 pM for W308051, AMG160, and isotype control, 10-fold serially diluted from 500 nM to 5.0 pM for AMG 340) were added into 96-well plates. Then, effector cells (fresh human PBMCs, $2\times10^5$ cells/50 μL/well) and C4-2 target cells ($2\times10^4$ cells/50 μL/well) were added into corresponding wells (E:T ratio=10:1). After incubation for 20 hours, the supernatant was collected and stored at −80° C. Released human IFN-γ, IL-2, TNF-α, and IL-6 in the supernatants were measured by ELISA. The relative light unit (RLU) was measured at $OD_{450}$ and $OD_{540}$ by SPECTRAMAX M5E. The concentration of human cytokines in the supernatant was quantitated according to the standard curve. The $EC_{50}$ was calculated by GraphPad Prism 7 software plotting antibody concentration (x-axis) versus percentage (y-axis) and analyzing as: Nonlinear regression (curve fit)-log (agonist) vs. response-Variable slope (four parameters).

Figure 18:
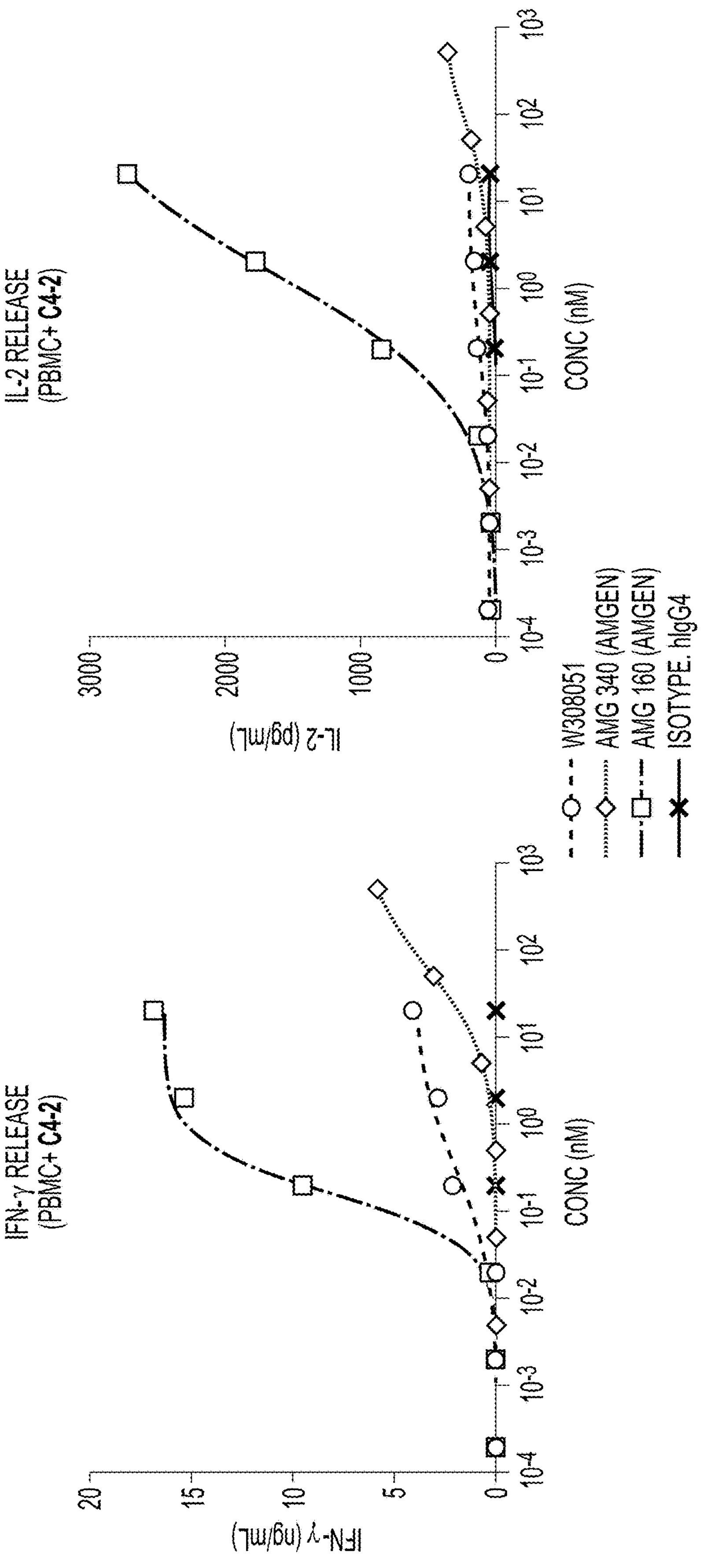
FIG. 18 shows cytokine release of C4-2 cells co-cultured with PBMCs, incubated with the antibodies W308051, AMG340, AMG160, and isotype hIgG4 control.
Figure 18:
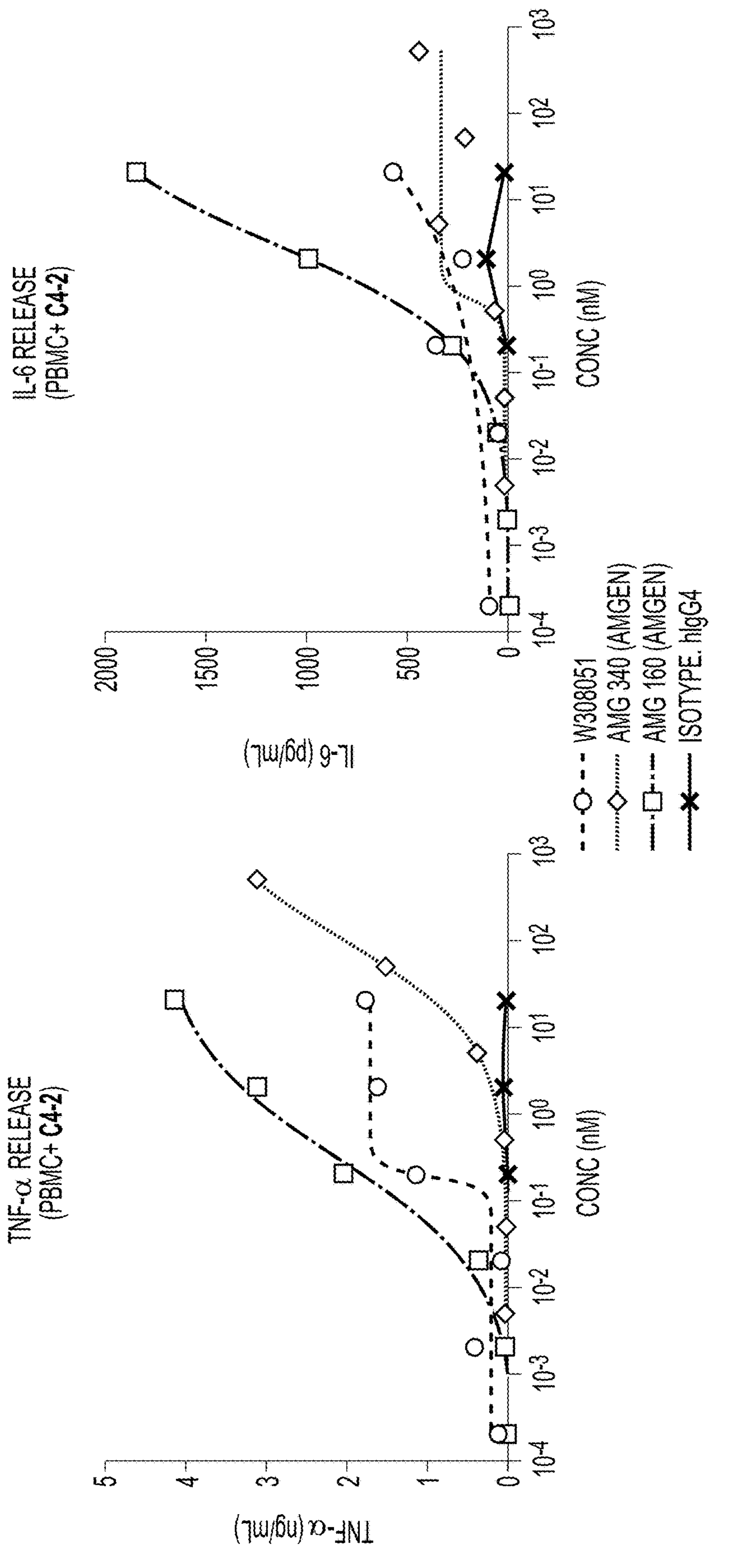

As shown in FIG. 18 and Table 16, W308051 induced low release of a panel of cytokine in PBMCs and C4-2 cells co-culture assay.

TABLE 16

| Cytokine release of C4-2 cells co-cultured with PBMCs | | | | | | | | |
|---|---|---|---|---|---|---|---|---|
| | PBMC + C4-2 | | PBMC + C4-2 | | PBMC + C4-2 | | PBMC + C4-2 | |
| Antibody | $EC_{50}$ (nM) | Max IFN-γ (ng/ml) | $EC_{50}$ (nM) | Max IL-2 (pg/mL) | $EC_{50}$ (nM) | Max TNF-α (ng/ml) | $EC_{50}$ (nM) | Max IL-6 (pg/mL) |
| W308051 | ~0.29 | 4.11 | ~0.18 | 206 | ~0.18 | 1.78 | NA | 575 |
| AMG 340 | ~63.0 | 5.86 | ~76.2 | 364 | 88.73 | 3.13 | ~0.68 | 446 |
| AMG 160 | 0.16 | 16.87 | ~1.35 | 2728 | ~0.30 | 4.14 | 2.86 | 1848 |

Figure 19:
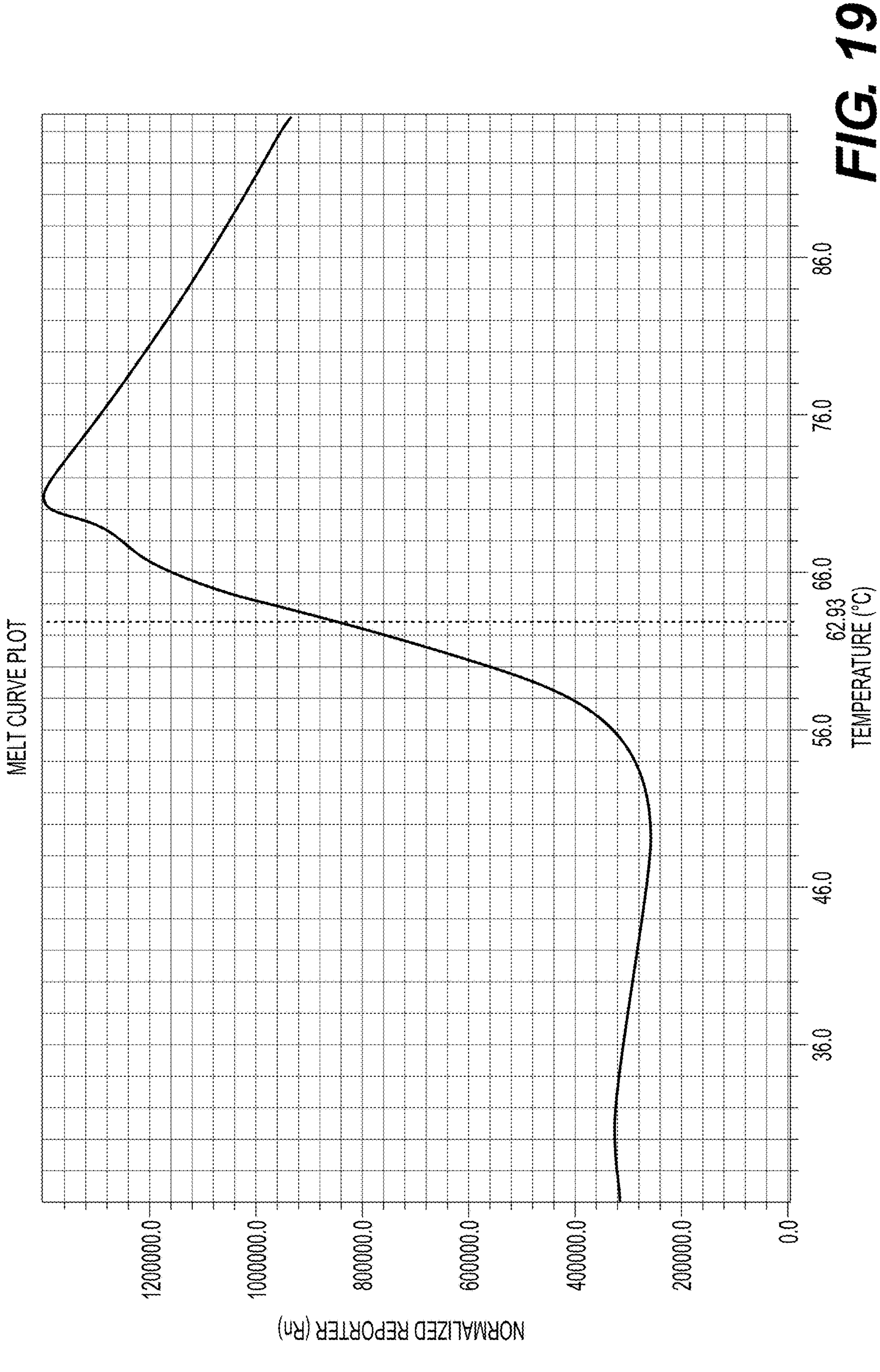
FIG. 19 shows the thermal stability of the antibody W308051 measured by DSF.

7.6 Thermal Stability Measured by DSF $T_m$ (melting temperature) of each antibody was investigated using QUANTSTUDIO 7 Flex Real-Time PCR system (Applied Biosystems). 19 μL of antibody solution was mixed with 1 μL of 80×SYPRO Orange Protein Gel Stain and transferred to the 96 well plate. The plate was sealed with the Optical Adhesive Film and centrifuged at 3,000 rpm for 5 min to remove any air bubbles. The plate was heated from 26° C. to 95° C. at a rate of 0.9° C./min, and the resulting fluorescence data was collected. The negative derivatives of the fluorescence changes with respect to different temperatures were calculated, and the maximal value was defined as melting temperature $T_m$. If a protein has multiple unfolding transitions, the first two $T_m$ were reported, named as Tm1 and $T_m2$. Data collection and $T_m$ calculation were conducted automatically by the QUANTSTUDIO Real-Time PCR software (v1.3). As shown in FIG. 19, W308051 showed good thermal stability with $T_m1$ of 62.9° C. and $T_m2$ of 69.3° C.

7.7 Hydrophobicity Interaction Chromatography HPLC (HIC-HPLC)

Figure 20:
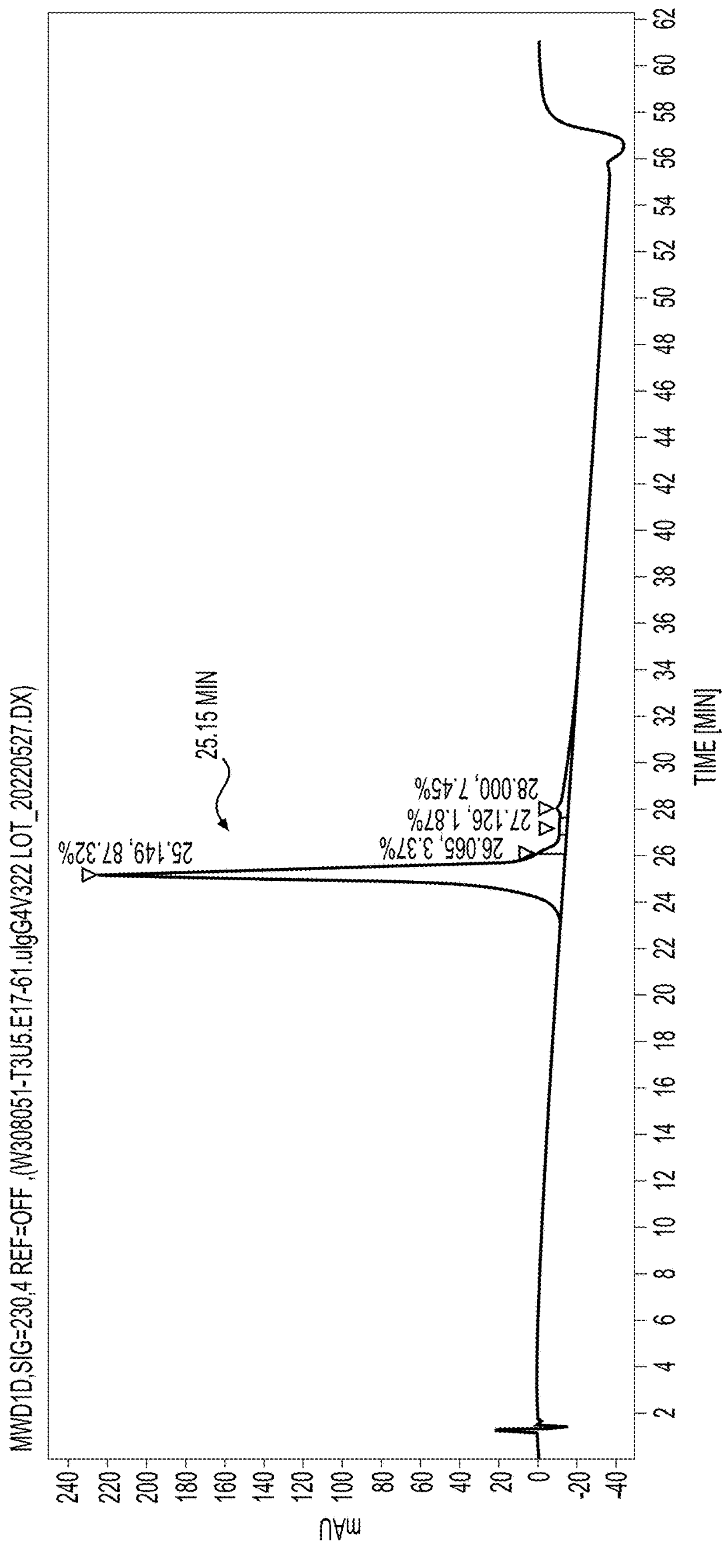
FIG. 20 shows the results of the antibody W308051 measured by hydrophobicity interaction chromatography HPLC (HIC-HPLC).

Hydrophobicity property of antibody was detected by HPLC 1260 Infinity II system (Agilent Technologics™) with TSKgel butyl-NPR column. The sample was diluted in PBS buffer and 20 μL diluted sample was injected into the column, and separated with a flow rate of 0.5 ml/min for 61 min. The peak retention was detected with UV light of the wavelength 280 nm and 230 nm. The retention time was analyzed with the HIC-HPLC analysis method to integrate all peak areas from 20 min to 40 min. The operation and analysis software are the OpenLab CDS Workstation (v2.6.0.691). As shown in FIG. 20, the retention time of W308051 by HIC-HPLC was 25.15 min, indicating that W308051 had low hydrophobicity.

3.8 Determination of Diffusion Interaction Parameter (kD) by DLS kD measurement was investigated using DYNAPRO Plate Reader III (Wyatt Technology). During the sample preparation process, the appearance of sample was recorded at thawing, filtration, and concentration. 7.5 μL sample solution was then added to a 1536 well microplate. Data collection was performed by the DYNAMICS operation software (v7.8.1.3). 5 acquisitions were collected for each protein sample while each acquisition time was 5 s. For each measurement, the diffusion coefficient was determined and plotted against protein concentration. kD values were calculated automatically by the software.

As shown in Table 17, W308051 showed high kD value and monodisperse size distribution, indicating that W308051 had good solubility properties.

TABLE 17

Diffusion interaction parameter (kD) by DLS

| Antibody | kD (mL/g) | $R^2$ | Size Distribution | pI | Buffer |
|---|---|---|---|---|---|
| W308051 | −8.0 | 0.9236 | mono-disperse size | 6.23 | 20 mM citrate, 8% sucrose, 0.02% PS80, pH 6.0 |

Example 8. In Vivo Characterization 8.1 Rat PK Study

The preliminary pharmacokinetic study of WBP308051 was tested in female CD (SD) IGS Rat by single intravenous bolus administrations. Briefly, female CD (SD) IGS Rat of 8-10-week-old (Beijing Charles River) were used in this study. Five animals, as one group, were administered with W308051 at 10 mg/kg by single intravenous bolus administration. PK serum samples were collected and the serum concentration of WBP308051 was determined by using 3 bioanalytical ELISA methods. In method 1 (Fc+Fc), 96-well ELISA plates were coated overnight at 4° C. with Goat anti-human IgG, then serially diluted plasma samples were added. Biotin-labeled goat anti-human IgG Fc was used as the detection antibody. In method 2 (PSMA+CD3), 96-well ELISA plates were coated overnight at 4° C. with human PSMA ECD protein, then serially diluted plasma samples were added. Biotin labeled Human CD3 epsilon was used as the detection protein. In method 3 (CD3+PSMA), 96-well ELISA plates were coated overnight at 4° C. with Recombinant human CD3 epsilon, then serially diluted plasma samples were added. Biotin-labeled human PSMA ECD protein was used as the detection protein. The absorbance was read at 450 nm and 540 nm using a microplate spectrophotometer (SPECTRAMAX M5E). The serum concentration of WBP308051 lead antibody in rats was subjected to a non-compartmental pharmacokinetic analysis by using the Phoenix WINNONLIN software (version 8.1, Pharsight, Mountain View, CA). The linear/log trapezoidal rule was applied in obtaining the PK parameters.

Figure 21:
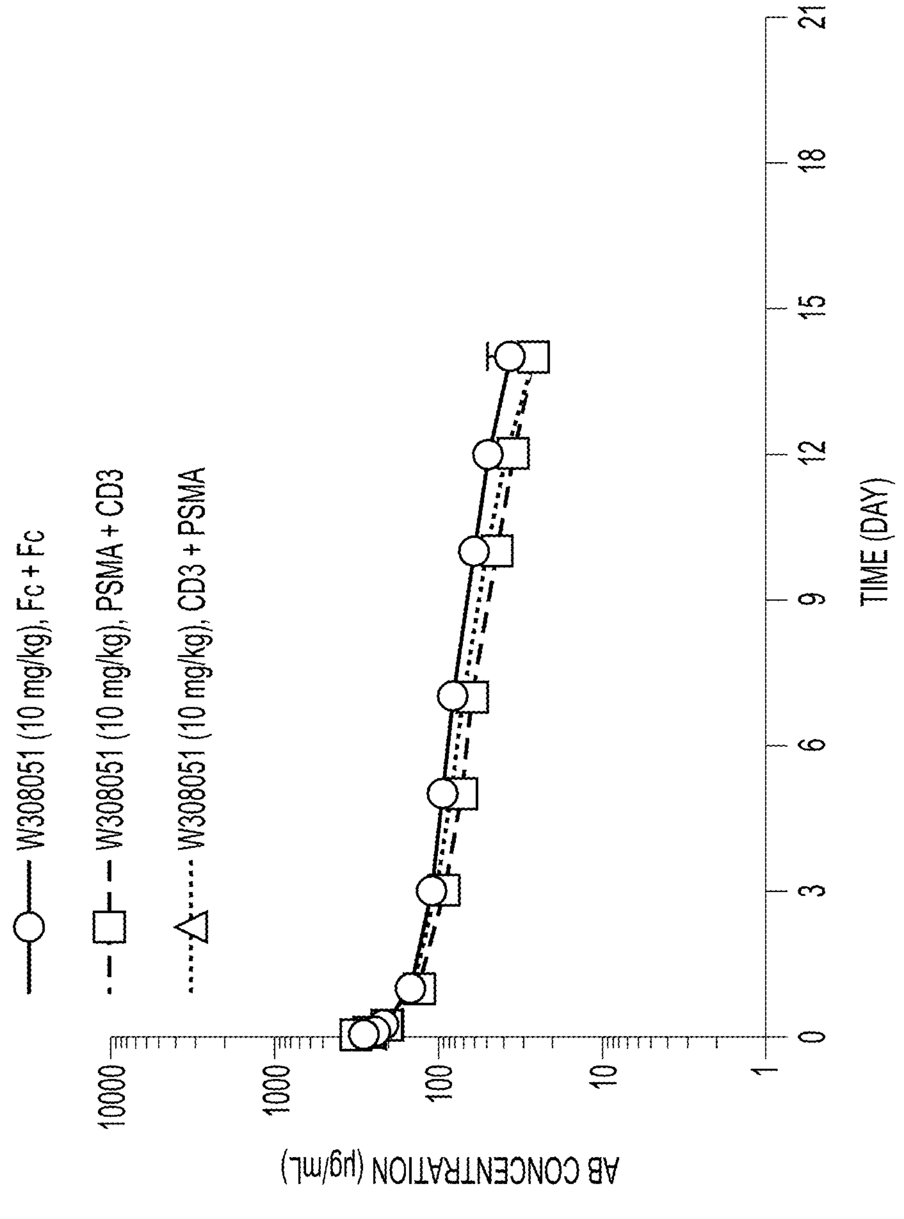
FIG. 21 shows average serum concentrations of the antibody W308051 in a pharmacokinetic study.

As shown in FIG. 21 and Table 18, for IV PK study at 10 mg/kg by using 3 ELISA settings (i.e., coating with Fc, PSMA, or CD3, and detection with Fc, CD3 or PSMA, respectively), WBP308051 showed average serum clearance at 6.05, 8.07 and 7.51 mL/day/kg, respectively; average half-life at 177, 142 and 132 h, respectively; Volume of distribution (Vss) at 59.1, 65.8 and 58.8 mL/kg, respectively; and AUCO-last at 30332, 24087 and 26745 h*μg/mL, respectively. The Similar results from 3 different ELISA settings suggested the good in vivo stability of W308051.

TABLE 18

Pharmacokinetic parameters summary

| Compound | G1_WBP308051 | G1_WBP308051 | G1_WBP308051 |
|---|---|---|---|
| Dose | | 10 mg/kg, iv | |
| Method | Fc + Fc | PSMA + CD3 | CD3 + PSMA |
| $t_{1/2}$ (h) | 177* | 142 | 132 |
| $C_{max}$ (μg/mL) | 293 | 322 | 287 |
| $AUC_{0-t}$ (h*μg/ml) | 30332 | 24087 | 26745 |
| Cl_obs (ml/day/kg) | 6.05 | 8.07 | 7.51 |
| MRTINF_obs (h) | 254 | 201 | 194 |
| Vss_obs (mL/kg) | 59.1 | 65.8 | 58.8 |

*The t½ may be inaccurate when the AUC_% Extrap_obs is greater than 20%.

8.2 In Vivo Efficacy in NPG-hPBMC Model

The in vivo efficacy of WBP308051 was tested in a LNCaP xenograft model on male NPG mice with human PBMC reconstitution. 2×10^6 LNCaP tumor cells were implanted (s.c.) into the right flanks of NPG mice. Each mouse also received 2×10^6 PBMC cells by i.p. injection. When tumors reached about 105 $mm^3$ in volume, tumor-bearing mice were randomly divided into 9 groups. The 9 groups of mice received following injections intraperitoneally twice a week for total 6 injections, respectively: vehicle-PBS; 0.30 mg/kg of AMG 340; 1.51 mg/kg of AMG 340; 0.057 mg/kg of AMG 160; 0.29 mg/kg of AMG 160; 1.44 mg/kg of AMG 160; 0.08 mg/kg of W308051; 0.4 mg/kg of W308051; 2 mg/kg of W308051. Mice body weight and tumor growth were measured twice a week. Tumor volume was calculated with the formula (½ (length×width$^2$). All the procedures related to animal handling, care, and treatment in the study were performed according to the guidelines approved by the Institutional Animal Care and Use Committee (IACUC) of LARC of WuXi Biologics following the guidance of the Association for Assessment and Accreditation of Laboratory Animal Care (AAALAC).

Figure 22A:
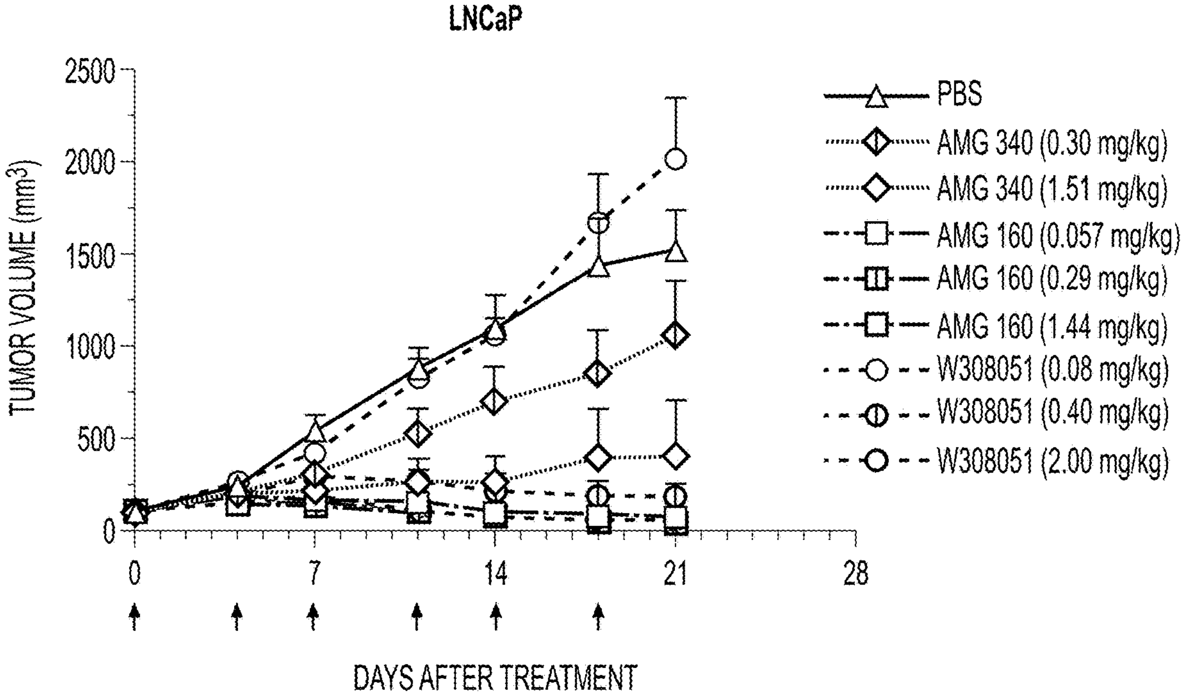
FIGS. 22A and 22B show in vivo efficacy of the antibodies (W308051, AMG340, and AMG160) in NPG-hPBMC Model.

The results of the tumor growth curve were shown in FIG. 22A. The mean tumor volume of the PBS group was 1527.3±216.73 $mm^3$ at day 21 post-treatment. Treatment of AMG160 at 0.057, 0.29. 1.44 mg/kg showed a strong anti-tumor effect compared to the treatment of PBS, with an average tumor volume of 86.63±10.42, 74.85±10.52, 50.36±4.54 $mm^3$ (TGI=101.39, 102.21, 103.93%). Treatment of AMG 340 at 0.30 and 1.51 mg/kg showed anti-tumor effect compared to the treatment of PBS, with an average tumor volume of 1061.97±296.65 and 441.45±297.15 (TGI=32.75, 78.53%). Treatment of W308051 at 0.4 and 2 mg/kg also showed a strong anti-tumor effect, with an average tumor volume of 193.46±264.26, 69.09±10.48 $mm^3$ (TGI=93.86, 102.63%). However, treatment of W308051 at 0.08 mg/kg showed no anti-tumor effect, with an average tumor volume of 2022.29±328.64 $mm^3$ (TGI=−34.84%).

Figure 22B:
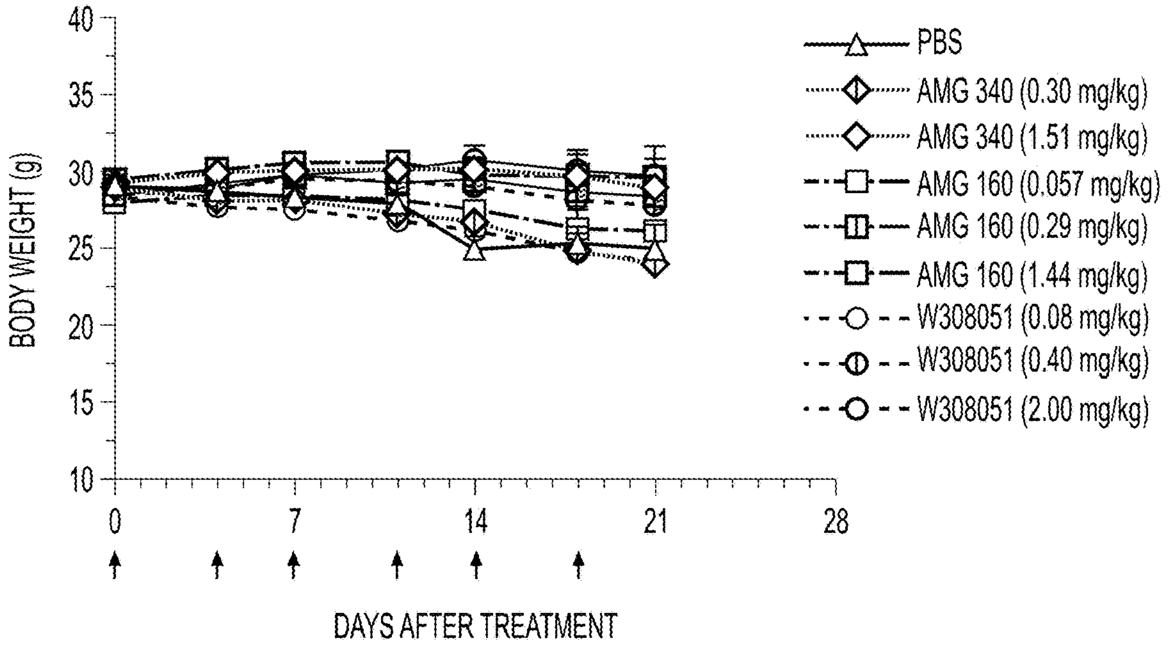

Body weights of mice were shown in FIG. 22B, slight body weight loss was observed during the study and that might be due to the GVHD (graft versus host disease) effect in the human PBMC reconstitution model.

In summary, W308051 inhibited the growth of LNCaP cells in vivo in a dose-dependent manner. W308051 induced comparable tumor growth inhibition to the equimolar of AMG 160 at high dose levels (0.40 and 2.00 mg/kg), and stronger tumor growth inhibition than the equimolar of AMG 340.

Those skilled in the art will further appreciate that the present disclosure may be embodied in other specific forms without departing from the spirit or central attributes thereof. In that the foregoing description of the present disclosure discloses only exemplary embodiments thereof, it is to be understood that other variations are contemplated as being within the scope of the present disclosure. Accordingly, the present disclosure is not limited to the particular embodiments that have been described in detail herein. Rather, reference should be made to the appended claims as indicative of the scope and content of the disclosure.

The invention claimed is:

1. A bispecific antibody or antigen-binding portion thereof, which comprises a prostate-specific membrane antigen (PSMA) binding moiety capable of binding to PSMA, wherein the PSMA binding moiety comprises a heavy chain CDR1 comprising the sequence of SEQ ID NO: 1, a heavy chain CDR2 comprising the sequence of SEQ ID NO: 2, a heavy chain CDR3 comprising the sequence of SEQ ID NO: 3, a light chain CDR1 comprising the sequence of SEQ ID NO: 4, a light chain CDR2 comprising the sequence of SEQ ID NO: 5, and a light chain CDR3 comprising the sequence of SEQ ID NO: 6; and a CD3 binding moiety that is capable of binding to CD3, wherein the CD3 binding moiety comprises a heavy chain CDR1 comprising the sequence of SEQ ID NO: 7, a heavy chain CDR2 comprising the sequence of SEQ ID NO: 8, a heavy chain CDR3 comprising the sequence of SEQ ID NO: 9, a light chain CDR1 comprising the sequence of SEQ ID NO: 10, a light chain CDR2 comprising the sequence of SEQ ID NO: 11, and a light chain CDR3 comprising the sequence of SEQ ID NO: 12.

2. The bispecific antibody or antigen-binding portion thereof of claim 1, wherein the PSMA binding moiety comprises a heavy chain comprising the sequence of SEQ ID NO: 19, and a light chain comprising the sequence of SEQ ID NO: 20.

3. The bispecific antibody or antigen-binding portion thereof of claim 1, wherein the CD3 binding moiety comprises a heavy chain comprising the sequence of SEQ ID NO: 17, and a light chain comprising the sequence of SEQ ID NO: 18.

4. The bispecific antibody or antigen-binding portion thereof of claim 1, wherein the PSMA binding moiety comprises a heavy chain comprising the sequence of SEQ ID NO: 19, and a light chain comprising the sequence of SEQ ID NO: 20; and wherein the CD3 binding moiety comprises a heavy chain comprising the sequence of SEQ ID NO: 17, and a light chain comprising the sequence of SEQ ID NO: 18.

5. A pharmaceutical composition comprising the isolated bispecific antibody or the antigen-binding portion thereof of claim 1, and a pharmaceutically acceptable carrier.

6. A conjugate comprising the isolated bispecific antibody or the antigen-binding portion thereof of claim 1.

7. An isolated nucleic acid molecule, comprising a nucleic acid sequence encoding the heavy chain and/or the light chain of the bispecific isolated antibody or the antigen-binding portion thereof of claim 1.

8. The isolated nucleic acid molecule of claim 7, wherein the nucleic acid sequence comprises one or more of any combination of the sequences of SEQ ID NOs: 35 to 38.

9. The isolated nucleic acid molecule of claim 7, wherein the nucleic acid sequence comprises one or more of the sequences of SEQ ID NOs: 37 to 38.

10. The isolated nucleic acid molecule of claim 7, wherein the nucleic acid sequences comprise all of the sequences of SEQ ID NOs: 35 to 38.

11. A vector comprising the nucleic acid molecule of claim 7.

12. A host cell comprising the vector of claim 11.

13. A method for preparing the bispecific antibody or antigen-binding portion thereof of claim 1, the method comprising:

a) expressing the bispecific antibody or antigen-binding portion thereof in a host cell; and b) isolating the bispecific antibody or antigen-binding portion thereof from the host cell.

14. A kit for treating or diagnosing a proliferative disorder, an immune disorder, or an infection, comprising a container comprising the isolated bispecific antibody or antigen-binding portion thereof of claim 1.

15. An isolated antibody or the antigen-binding portion thereof, comprising a prostate-specific membrane antigen (PSMA) binding moiety capable of binding to PSMA, wherein the PSMA binding moiety comprises:

a heavy chain CDR1 comprising the sequence of SEQ ID NO: 1, a heavy chain CDR2 comprising the sequence of SEQ ID NO: 2, a heavy chain CDR3 comprising the sequence of SEQ ID NO: 3, a light chain CDR1 comprising the sequence of SEQ ID NO: 4, a light chain CDR2 comprising the sequence of SEQ ID NO: 5, and a light chain CDR3 comprising the sequence of SEQ ID NO: 6.

16. The antibody or antigen-binding portion thereof of claim 15, wherein the PSMA binding moiety comprises a heavy chain comprising the sequence of SEQ ID NO: 19, and a light chain comprising the sequence of SEQ ID NO: 20.

17. An isolated nucleic acid molecule, comprising a nucleic acid sequence encoding a heavy chain and/or a light chain of the antibody or the antigen-binding portion thereof of claim 15.

18. A bispecific antigen-binding molecule comprising:

a) a CD3 binding moiety, wherein the CD3 binding moiety comprises:

a heavy chain CDR1 comprising the sequence of SEQ ID NO: 7, a heavy chain CDR2 comprising the sequence of SEQ ID NO: 8, a heavy chain CDR3 comprising the sequence of SEQ ID NO: 9, a light chain CDR1 comprising the sequence of SEQ ID NO: 10, a light chain CDR2 comprising the sequence of SEQ ID NO: 11, a light chain CDR3 comprising the sequence of SEQ ID NO:12; and b) a prostate-specific membrane antigen (PSMA) binding moiety, wherein the PSMA binding moiety comprises:

a heavy chain CDR1 comprising the sequence of SEQ ID NO: 1, a heavy chain CDR2 comprising the sequence of SEQ ID NO: 2, a heavy chain CDR3 comprising the sequence of SEQ ID NO: 3, a light chain CDR1 comprising the sequence of SEQ ID NO: 4, a light chain CDR2 comprising the sequence of SEQ ID NO: 5, a light chain CDR3 comprising the sequence of SEQ ID NO: 6; and c) a first human hinge region-CH2-CH3 domain comprising at least one mutation selected from the group consisting of (i) S228P, (ii) F234A, L235A, (iii) S354C, T366W, (iv) Y349C, T366S, L368A, Y407V; and (v) combinations thereof d) a second human hinge region-CH2-CH3 domain comprising at least one mutation selected from the group consisting of (i) S228P, (ii) F234A, L235A, (iii) S354C, T366W, (iv) Y349C, T366S, L368A, Y407V; and (v) combinations thereof, wherein the PSMA binding moiety is operably linked to (c), and wherein the CD3 binding moiety is operably linked to (d).

* * * * *